(12) United States Patent
Zach et al.

(10) Patent No.: US 10,970,594 B2
(45) Date of Patent: *Apr. 6, 2021

(54) MAGNETIC RESONANCE MAPS FOR ANALYZING TISSUE

(71) Applicants: Tel HaShomer Medical Research Infrastructure and Services Ltd., Ramat-Gan (IL); Ramot at Tel-Aviv University Ltd., Tel-Aviv (IL)

(72) Inventors: Leor Zach, Rehovot (IL); David Guez, Tel-Aviv (IL); David Last, Jerusalem (IL); Dianne Daniels Elmakias, Ramat-HaSharon (IL); Yael Mardor, Natania (IL); Shirley Sharabi, Ramat Gan (IL); Noam Nissan, Tel-Aviv (IL); Miriam Sklair-Levy, Mevasseret Zion (IL)

(73) Assignees: Tel HaShomer Medical Research Infrastructure and Services Ltd., Ramat-Gan (IL); Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,089

(22) Filed: Feb. 20, 2019

(65) Prior Publication Data
US 2019/0180139 A1 Jun. 13, 2019

Related U.S. Application Data

(63) Continuation of application No. 14/352,099, filed as application No. PCT/IB2012/055703 on Oct. 18, 2012, now Pat. No. 10,275,680.

(Continued)

(51) Int. Cl.
*G06K 9/62* (2006.01)
*A61B 5/055* (2006.01)
(Continued)

(52) U.S. Cl.
CPC .......... *G06K 9/6202* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS

| 4,439,451 A | 3/1984 | Coleman |
| 4,801,575 A | 1/1989 | Pardridge |

(Continued)

FOREIGN PATENT DOCUMENTS

| JP | 2010-526636 | 8/2010 |
| WO | WO 03/025606 | 3/2003 |

(Continued)

OTHER PUBLICATIONS

Hazle, John D., et al. "Dynamic imaging of intracranial lesions using fast spin-echo imaging: Differentiation of brain tumors and treatment effects." Journal of Magnetic Resonance Imaging 7.6 (1997): 1084-1093. (Year: 1997).*

(Continued)

*Primary Examiner* — Vu Le
*Assistant Examiner* — Tracy Mangialaschi

(57) ABSTRACT

Apparatus for analyzing brain MRI, is disclosed. The apparatus comprises an input for receiving a first and a second MRI scans at the beginning and end of a predetermined time interval post contrast administration; a subtraction map former for forming a subtraction map from said first and said second MRI scans by analyzing said scans to distinguish between two primary populations, a slow population, in which contrast clearance from the tissue is slower than contrast accumulation, and a fast population in which clearance is faster than accumulation; and an output to provide an (Continued)

indication of distribution of said two primary populations, wherein said predetermined time period is at least twenty minutes.

**20 Claims, 31 Drawing Sheets
(25 of 31 Drawing Sheet(s) Filed in Color)**

Related U.S. Application Data

(60) Provisional application No. 61/548,737, filed on Oct. 19, 2011.

(51) Int. Cl.
*A61B 5/00* (2006.01)
*G06T 7/00* (2017.01)
*G16H 50/50* (2018.01)

(52) U.S. Cl.
CPC .......... *G06T 7/0012* (2013.01); *A61B 5/0037* (2013.01); *A61B 2576/026* (2013.01); *G16H 50/50* (2018.01)

(56) References Cited

U.S. PATENT DOCUMENTS

| | | | |
|---|---|---|---|
| 5,004,697 A | 4/1991 | Pardridge | |
| 5,004,949 A | 4/1991 | Latassa et al. | |
| 5,059,415 A | 10/1991 | Neuwelt | |
| 5,186,924 A | 2/1993 | Fishman | |
| 5,260,050 A | 11/1993 | Ranney | |
| 5,266,480 A | 11/1993 | Naughton et al. | |
| 5,434,137 A | 7/1995 | Black | |
| 5,506,206 A | 4/1996 | Kozarich et al. | |
| 5,550,933 A | 8/1996 | Stetten | |
| 5,591,715 A | 1/1997 | Coon et al. | |
| 5,670,477 A | 9/1997 | Poduslo et al. | |
| 5,752,515 A | 5/1998 | Jolesz et al. | |
| 6,294,520 B1 | 9/2001 | Naito | |
| 6,419,949 B1 | 7/2002 | Gasco | |
| 6,574,501 B2 | 6/2003 | Lambert et al. | |
| 6,703,381 B1 | 3/2004 | Ekwuribe et al. | |
| 2002/0026116 A1 | 2/2002 | Schmainda | |
| 2003/0050552 A1 | 3/2003 | Vu | |
| 2004/0096395 A1 | 5/2004 | Xiong et al. | |
| 2004/0220644 A1 | 11/2004 | Shalev et al. | |
| 2005/0171423 A1 | 8/2005 | Ho et al. | |
| 2006/0052690 A1 | 3/2006 | Sirohey et al. | |
| 2006/0058624 A1 | 3/2006 | Kimura | |
| 2006/0183998 A1 | 8/2006 | Biglieri et al. | |
| 2006/0204443 A1 | 9/2006 | Kobayashi et al. | |
| 2006/0226836 A1 | 10/2006 | Shu et al. | |
| 2006/0245629 A1* | 11/2006 | Huo .................... | G06T 7/0012 382/131 |
| 2007/0263769 A1 | 11/2007 | Roell | |
| 2008/0100612 A1 | 5/2008 | Dastmalchi et al. | |
| 2009/0264734 A1 | 10/2009 | Degani et al. | |
| 2010/0106007 A1 | 4/2010 | Wacker et al. | |
| 2010/0142786 A1 | 6/2010 | Degani et al. | |
| 2010/0172842 A1* | 7/2010 | Israeli .................... | A61B 5/055 424/9.3 |
| 2010/0259263 A1* | 10/2010 | Holland ................ | A61B 5/055 324/310 |
| 2011/0152692 A1 | 6/2011 | Nie et al. | |
| 2012/0101365 A1 | 4/2012 | Israeli et al. | |
| 2013/0119985 A1* | 5/2013 | Lin .................... | G01R 33/4818 324/309 |
| 2013/0274281 A1 | 10/2013 | Bradley | |
| 2014/0270451 A1 | 9/2014 | Zach et al. | |
| 2015/0265210 A1 | 9/2015 | Israeli et al. | |
| 2016/0008619 A1 | 1/2016 | Pell et al. | |
| 2016/0109539 A1 | 4/2016 | Mardor et al. | |

FOREIGN PATENT DOCUMENTS

| | | |
|---|---|---|
| WO | WO 2006/035443 | 4/2006 |
| WO | WO 2007/035721 | 3/2007 |
| WO | WO 2008/139480 | 11/2008 |
| WO | WO 2012/011069 | 1/2012 |
| WO | WO 2013/057697 | 4/2013 |
| WO | WO 2014/174480 | 10/2014 |

OTHER PUBLICATIONS

Furman-Haran, Edna, et al. "Response of MCF7 human breast cancer to tamoxifen: evaluation by the three-time-point, contrast-enhanced magnetic resonance imaging method." Clinical cancer research 4.10 (1998): 2299-2304. (Year: 1998).*
Furman-Haran, Edna, et al. "Critical role of spatial resolution in dynamic contrast-enhanced breast MRI." Journal of Magnetic Resonance Imaging: An Official Journal of the International Society for Magnetic Resonance in Medicine 13.6 (2001): 862-867. (Year: 2001).*
Pandit, Prachi. "Non-Cartesian MR microscopy for cancer imaging in small animals." Dissertation Abstracts International 71.04 (2010). (Year: 2010).*
Official Action dated Jun. 28, 2019 From the US Patent and Trademark Office Re. U.S. Appl. No. 14/787,040. (9 pages).
Advisory Action Before the Filing of an Appeal Brief dated Jun. 18, 2013 From the US Patent and Trademark Office Re. U.S. Appl. No. 13/342,222.
Applicant-Initiated Interview Summary dated Aug. 2, 2018 From the US Patent and Trademark Office Re. U.S. Appl. 14/352,099. (3 pages).
Communication Pursuant to Article 94(3) EPC dated Apr. 13, 2015 From the European Patent Office Re. Application No. 08751361.0.
Communication Pursuant to Article 94(3) EPC dated Jul. 20, 2018 From the European Patent Office Re. Application No. 14789048.7. (7 Pages).
Communication Pursuant to Article 94(3) EPC dated May 22, 2014 From the European Patent Office Re. Application No. 08751361.0.
Examination Report Under Sections 12 & 13 of the Patents Act, 1970 and the Patents Rules, 2003 dated Jul. 20, 2017 From the Government of India, Patent Office, Intellectual Property Building Re. Application No. 7341/CHENP/2009. (4 Pages).
International Preliminary Report on Patentability dated May 1, 2014 From the International Bureau of WIPO Re. Application No. PCT/IB2012/055703.
International Preliminary Report on Patentability dated Nov. 5, 2015 From the International Bureau of WIPO Re. Application No. PCT/IB2014/060981.
International Preliminary Report on Patentability dated Nov. 26, 2009 From the International Bureau of WIPO Re. Application No. PCT/IL2008/000673.
International Search Report and the Written Opinion dated Sep. 10, 2014 From the International Searching Authority Re. Application No. PCT/IB2014/060981.
International Search Report and the Written Opinion dated Mar. 19, 2013 From the International Searching Authority Re. Application No. PCT/IB2012/055703.
International Search Report dated Jun. 3, 2009 From the International Searching Authority Re. Application No. PCT/IL2008/000673.
Invitation Pursuant to Rule 63(1) EPC dated May 22, 2014 From the European Patent Office Re. Application No. 12151382.4.
Notification of Reasons for Rejection dated Jan. 30, 2018 From the Japan Patent Office Re. Application No. 2016-509589 and Its Translation Into English. (10 Pages).
Notification of Reasons for Rejection dated Oct. 30, 2018 From the Japan Patent Office Re. Application No. 2016-509589 and Its Translation Into English. (4 Pages).
Office Action dated Mar. 3, 2013 From the Israel Patent Office Re. Application No. 223743 and Its Translation Into English.
Office Action dated Feb. 13, 2013 From the Israel Patent Office Re. Application No. 217360 and Its Translation Into English.

(56) References Cited

OTHER PUBLICATIONS

Office Action dated May 13, 2018 From the Israel Patent Office Re. Application No. 232176 and Its Translation Into English. (4 Pages).
Office Action dated Feb. 19, 2012 From the Israel Patent Office Re. Application No. 202118 and Its Translation Into English.
Office Action dated Feb. 20, 2012 From the Israel Patent Office Re. Application No. 217360 and Its Translation Into English.
Official Action dated Jul. 1, 2016 From the US Patent and Trademark Office Re. U.S. Appl. No. 12/451,477.
Official Action dated Oct. 2, 2015 From the US Patent and Trademark Office Re. U.S. Appl. No. 12/451,477.
Official Action dated Jun. 5, 2014 From the US Patent and Trademark Office Re. U.S. Appl. No. 13/342,222.
Official Action dated Apr. 6, 2018 From the US Patent and Trademark Office Re. U.S. Appl. No. 14/787,040. (43 pages).
Official Action dated Jan. 7, 2019 From the US Patent and Trademark Office Re. U.S. Appl. No. 14/787,040. (14 pages).
Official Action dated Aug. 8, 2017 From the US Patent and Trademark Office Re. U.S. Appl. No. 14/726,629. (52 pages).
Official Action dated Feb. 11, 2013 From the US Patent and Trademark Office Re. U.S. Appl. No. 12/451,477.
Official Action dated Jan. 14, 2016 From the US Patent and Trademark Office Re. U.S. Appl. No. 14/352,099.
Official Action dated Jun. 15, 2017 From the US Patent and Trademark Office Re. U.S. Appl. No. 14/352,099. (34 Pages).
Official Action dated Dec. 18, 2012 From the US Patent and Trademark Office Re. U.S. Appl. No. 13/342,222.
Official Action dated Dec. 18, 2014 From the US Patent and Trademark Office Re. U.S. Appl. No. 12/451,477.
Official Action dated Apr. 19, 2018 From the US Patent and Trademark Office Re. U.S. Appl. No. 14/352,099. (40 pages).
Official Action dated Dec. 20, 2013 From the US Patent and Trademark Office Re. U.S. Appl. No. 13/342,222.
Official Action dated Oct. 20, 2016 From the US Patent and Trademark Office Re. U.S. Appl. No. 14/352,099.
Official Action dated Apr. 23, 2012 From the US Patent and Trademark Office Re. U.S. Appl. No. 12/451,477.
Official Action dated Mar. 23, 2017 From the US Patent and Trademark Office Re. U.S. Appl. No. 12/451,477. (25 pages).
Official Action dated Jul. 25, 2012 From the US Patent and Trademark Office Re. U.S. Appl. No. 13/342,222.
Official Action dated Dec. 30, 2014 From the US Patent and Trademark Office Re. U.S. Appl. No. 13/342,222.
Partial European Search Report and the European Search Opinion dated Oct. 7, 2014 From the European Patent Office Re. Application No. 12151382.4.
Restriction Official Action dated Apr. 13, 2012 From the US Patent and Trademark Office Re. U.S. Appl. No. 13/342,222.
Summons to Attend Oral Proceedings Pursuant to Rule 115(1) EPC dated Jul. 12, 2016 From the European Patent Office Re. Application No. 12151382.4.
Supplementary European Search Report and the European Search Opinion dated Dec. 19, 2016 From the European Patent Office Re. Application No. 14789048.7. (7 Pages).
Supplementary European Search Report and the European Search Opinion dated Apr. 23, 2015 From the European Patent Office Re. Application No. 12841602.1.
Translation of Notice of Reason for Rejection dated Apr. 19, 2013 From the Japanese Patent Office Re. Application No. 2010-508031.
Written Opinion dated Jun. 3, 2009 From the International Searching Authority Re. Application No. PCT/IL2008/000673.
Abbott et al. "Astrocyte-Endothelial Interactions at the Blood-Brain Barrier", Nature Reviews Neuroscience, 7: 41-53, 2006.
Aicher et al. "Contrast-Enhanced Magnetic Resonance Imaging of Tumor-Bearing Mice Treated With Human Recombinant Tumor Necrosis Factor Alpha", Cancer Research, 50: 7376-7381, Nov. 15, 1990.
Ballabh et al. "The Blood-Brain Barrier: An Overview Structure, Regulation, and Clinical Implications", Neurobiology of Disease, 16: 1-13, 2004.

Bennett et al. "Detection of Blood-Brain Barrier Disruption in Rat Brain After Osmotic Shock Using Manganese-Enhanced Magnetic Resonance Imaging (MEMRI)", Proceedings of the International Society for Magnetic Resonance in Medicine, 14: 2324, May 6, 2006.
Blanchette et al. "Real Time Monitoring of Hyperosmolar Blood Brain Barrier Disruption Using MRI", Proceedings of the International Society for Magnetic Resonance in Medicine, 14: 998, May 6, 2006.
Choi et al. "New subtraction Algorithms for Evaluation of Lesions on Dynamic Contrast-Enhanced MR Mammography", European Radiologyl,12: 3018-3022, Dec. 18, 2002.
Choi et al. "Three-Phase Dynamic Breast Magnetic Resonance Imaging With Two-Way Subtraction", Journal of Computer Assisted Tomography, 29(6): 834-841, Nov./Dec. 2005.
Ding et al. "Contrast-Enhanced Subtraction Harmonic Sonography for Evaluating Treatment Response in Patients With Hepatocellular Carcinoma", American Journal of Roentgenology, AJR, 176: 661-666, Mar. 2001.
Ewing et al. "Patlak Plots of Gd-DTPA MRI Data Yield Blood-Brain Transfer Constants Concordant With Those of 14C-Sucrose in Areas of Blood-Brain Opening", Magnetic Resonance in Medicine, 50: 283-292, 2003.
Fiscus "Molecular Mechanisms of Endothelium-Mediated Vasodilation", Seminars in Thrombosis and Hemostasis, 14(Suppl.): 12-22, 1988.
Furman-Haran et al. "Response of MCF7 Human Breast Cancer to Tamoxifen: Evaluation by the Three-Time-Point, Contrast-Enhanced Magnetic Resonance Imaging Method1", Clinical Cancer Research,4: 2299-2304, Oct. 1998.
Gabata et al. "Delayed MR Imaging of the Liver: Correlation of Delayed Enhancement of Hepatic Tumors and Pathologic Appearance", Abdominal Imaging, 23:309-313, 1998.
Gahramanov et al. "Potential for Differentiation of Pseudoprogression From True Tumor Progression With Dynamic Susceptibility-Weighted Contrast-Enahnced Magnetic Resonance Imaging Using Ferumoxytol Vs. Gadoteridol: A Pilot Study", International Journal of Radiation: Oncology Biology Physics, XP027581301, 79(2): 514-523, Feb. 1, 2011.
Harris et al. "MRI Measurement of Blood-Brain Barrier Permeability Following Spontaneous Reperfusion in the Starch Microsphere Model of Ischemia", Magnetic Resonance Imaging, 20: 221-230, 2002.
Hazle et al. "Dynamic Imaging of Intracranial Lesions Using Fast Spin-Echo Imaging: Differentiation of Brain Tumors and Treatment Effects", Journal of Magnetic Resonance Imaging, 7(6): 1084-1093, Nov.-Dec. 1997.
Hu et al. "Support Vector Machine Multiparametric MRI Identification of Pseudoprogression From Tumor Recurrence in Patients With Resected Glioblastoma", Journal of Magnetic Resonance Imaging, XP055156185, 33(2): 296-305, Feb. 27, 2011.
Hynynen et al. "Local and Reversible Blood-Brain Barrier Disruption by Noninvasive Focused Ultrasound at Frequencies Suitable for Transl-Skull Sonications", NeuroImage, 24: 12-20, 2005.
Israeli et al. "The Application of MRI for Depiction of Subtle Blood Brain Barrier Disruption in Stroke", International Journal of Biological Sciences, XP003031151, 7(1): 1-8, Dec. 26, 2010. Abstract, Fig.1, p. 2-3, p. 2, col. 1, Para 1, 3, p. 2, col. 2, Para 3—p. 6, col. 1, Para 1, p. 7, col. 1, Para 1—col. 2, Para 2, Figs.
Kilmer et al. "Brainsway Reports Positive Preliminary Results of Study Using Deep TMS to Open the Blood-Brain Barrier in Patients With Brain Tumors", Brainsway, Marketwire L.P., 2 P., Sep. 1, 2011.
Kinoshita et al. "Targeted Delivery of Antibodies Through the Blood-Brain Barrier by MRI-Guided Focused Ultrasound", Biochemical and Biophysical Research Communications, BBRC, 340: 1085-1090, 2006.
Knight et al. "Quantitation and Localization of Blood-to-Brain Influx by Magnetic Resonance Imaging and Quantitative Autoradiography in A Model of Transient Focal Ischemia", Magnetic Resonance in Medicine, 54: 813-821, 2005.

(56) References Cited

OTHER PUBLICATIONS

Kratz et al. "Seizure in A Nonpredisposed Individual Induced by Single-Pulse Transcranial Magentic Stimulation", The Journal of ECT, 27(1): 48-50, Mar. 2011. Abstract.

Latour et al. "Early Blood-Brain Barrier Disruption in Human Focal Brain Ischemia", Annals of Neurology, 56: 468-477, 2004.

Lewin et al. "Dual-Energy Constrast-Enhanced Digital Subtraction Mammography: Feasibility", Radiology, 229: 261-268, Mar. 2003.

Li et al. "Prefrontal Cortex Transcranial Magnetic Stimulation Does Not Change Local Diffusion: A Magnetic Resonance Imaging Study in Patients With Depression", Cognitive Behavioral Neurology, XP008169430, 16(2): 128-135, Jun. 2003. Abstract.

Liess et al. "Assessing the Extent of Blood Brain Barrier Breakdown Using Signal Vs. Time Curves and rCBV Maps in Patients With High-Grade Brain Tumours", Proceedings of the International Society for Magnetic Resonance in Medicine, 10: 2085, May 18, 2002.

Macdonald et al. "Response Criteria for Phase II Studies of Supratentorial Malignant Glioma", Journal of Clinical Oncology, 8(7): 1277-1280, Jul. 1990.

Mannelli et al. "Evaluation of Nonenhancing Tumor Fraction Assessed by Dynamic Contrast-Enhanced MRI Subtraction as A Predictor of Decrease in Tumor Volume in Response to Chemoradiotherapy in Advanced Cervical Cancer", American Journal of Roentgenology, AJR, XP003031152, 195(2): 524-527. Aug. 2010. Abstract, p. 525, 2nd Col. "Voxel-by-Voxel Subtraction Was Performed on a Dedicated Workstation".

Marchi et al. "The Etiological Role of Blood-Brain Barrier Dysfunction in Seizure Disorders", Cardiovascular Psychiatry and Neurology, 2011(Article ID): 382415-1-482415-9, 2011.

Miyati "The 1st Multi-Modality Symposium—'Versus' Brain Perfusion—3. From MRI's Perspective", Innervision, 18(2): 17-22, Dec. 2003.

Newatia et al. "Subtraction Imaging: Applications for Nonvascular Abdominal MRI", American Journal of Roentgenology, AJR, 188(4): 1018-1025, Apr. 2007.

Nitsche et al. "MRI Study of Human Brain Exposed to Weak Direct Current Stimulation of the Frontal Cortex", Clinical Neurophysiology, XP004559987, 115(10): 2419-2423, Available Online Jun. 8, 2004. Abstract.

Oberman et al. "Safety of Theta Burst Transcranial Magnetic Stimulation: A Systematic Review of the Literature", Journal of Clinical Neurophysiology, 28(1): 67-74, Feb. 2011.

Plewnia et al. "Transient Suppression of Tinnitus by Transcranial Magnetic Stimulation", Annals in Neurology, 53: 263-266, 2003.

Powers et al. "The High-Resolution, Three-Dimensional Solution Structure of Human Interleukin-4 Determined by Multidimensional Heteronuclear Magnetic Resonance Spectroscopy", Biochemistry, 32: 6744-6762, 1993. p. 6746, Lines 16-24.

Ravnborg et al. "No Effect of Pulsed Magnetic Stimulation on the Blood-Brain Barrier in Rats", Neuroscience, 38(1): 277-280, 1990. Abstract.

Sheikov et al. "Cellular Mechanisms of the Blood-Brain Barrier Opening Induced by Ultrasound in Presence of Microbubbles", Ultrasound in Medicine & Biology, 30(7): 979-989, 2004.

Shindo et al. "Blood-Brain Barrier Dysfunction in White Matter Lesions of Elderly Patients With Dementia", The Journal of Tokyo Medical University, Japan, 63(5): 395-400, Sep. 2005. Abstract in English.

Taheri et al. "Kalman Filtering for Reliable Estimation of BBB Permeability", Magnetic Resonance Imaging, 24: 1039-1049, 2006.

Tofts "Optimal Detection of Blood-Brain Barrier Defects With Gd-DTPA MRI—The Influences of Delayed Imaging and Optimised Repetition Time", Magnetic Resonance Imaging, 14(4): 373-380, 1996.

Tomkins et al. "Blood-Brain Barrier Disruption in Post-Traumatic Epilepsy", Journal of Neurology, Neurosurgery, and Psychiatry, 79(7): 774-777, Published Online Nov. 8, 2007.

Van den Bent et al. "End Point Assessment in Gliomas: Novel Treatments Limit Usefulness of Classical Macdonald's Criteria", Journal of Clinical Oncology, 27(18): 2905-2908, Jun. 20, 2009.

Vovk et al. "A Review of Methods for Correction of Intensity Inhomogeneity in MRI", IEEE Transactionson Medical Imaging, 26(3): 405-421, Mar. 2007.

Wang et al. "Vascular Volume and Blood-Brain Barrier Permeability Measured by Dynamic Contrast Enhanced MRI in Hippocampus and Cerebellum of Patients With MCI and Normal Controls", Journal of Magnetic Resonance Imaging, 24: 695-700, 2006.

Wen et al. "Malignant Gliomas in Adults", The New England Journal of Medicine, 359(5): 492-507, Jul. 31, 2008.

Wong et al. "Outcomes and Prognostic Factors in Recurrent Glioma Patients Enrolled Onto Phase II Clinical Trials", Journal of Clinical Oncology, 17(8): 2572-2578, Aug. 1999.

Yahaghi et al. "Estimation of Contrast Agent Concentration in Intra- and Extra-Vascular Spaces of Brain Tissue", Mathematical Biosciences, 204: 102-118, 2006.

Zach et al. "Delayed Contrast Extravasation MRI for Depicting Tumor and Non-Tumoral Tissues in Primary and Metastatic Brain Tumors", POS ONE, XP055320974, 7(12): e52008-1-e52008-17, Dec. 14, 2012. p. 4-6, 9.

Official Action dated Dec. 4, 2019 From the US Patent and Trademark Office Re. U.S. Appl. No. 141787,040. (10pages).

* cited by examiner

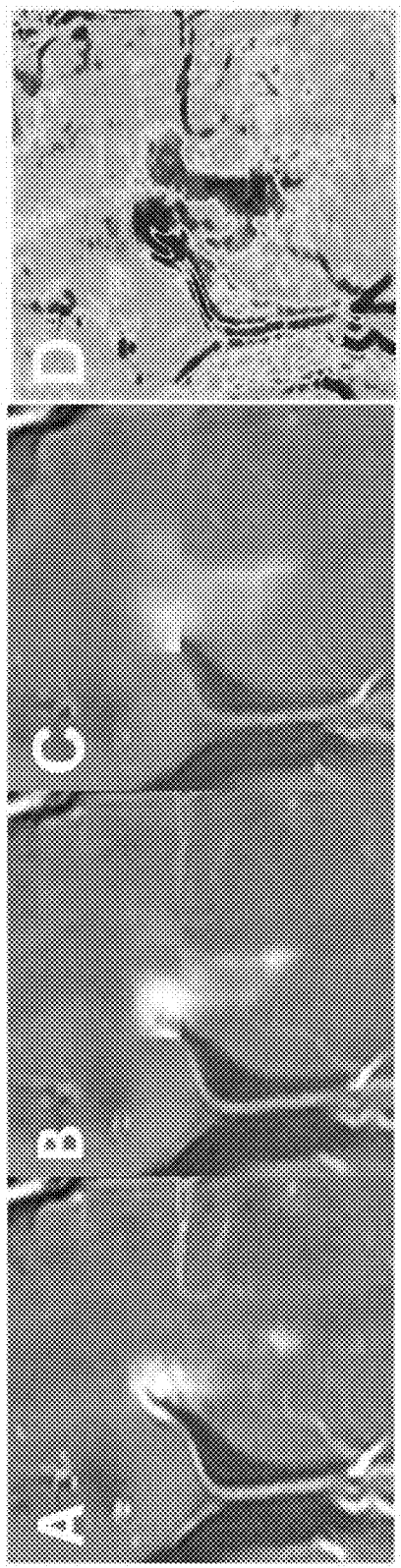
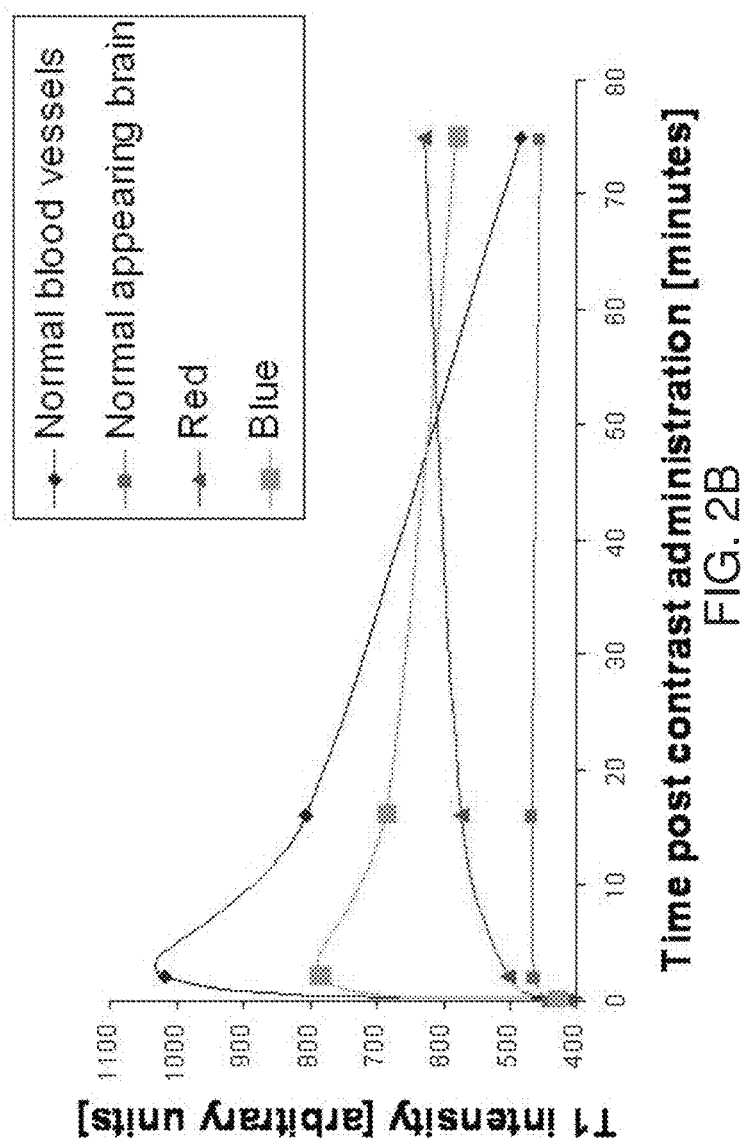
FIG. 2B

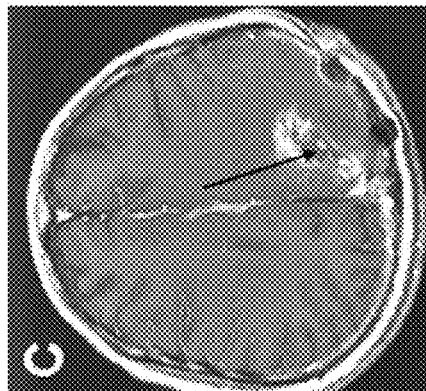
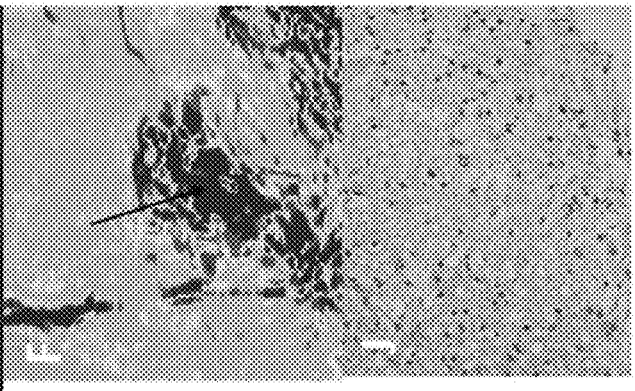
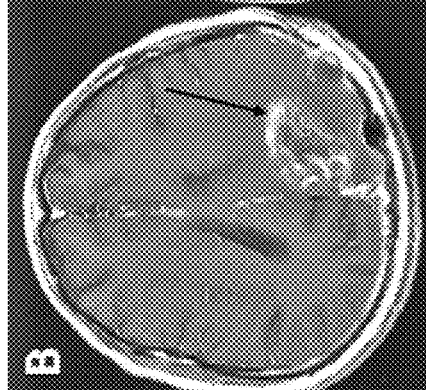
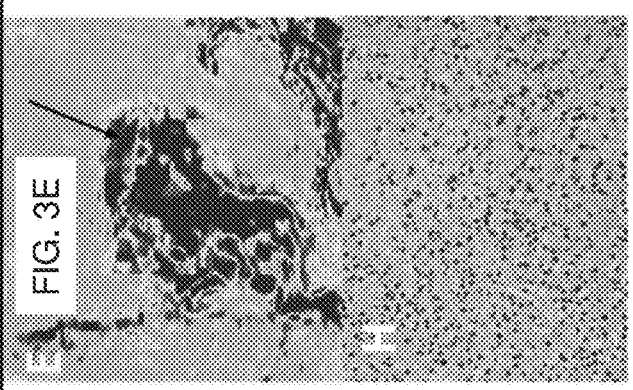
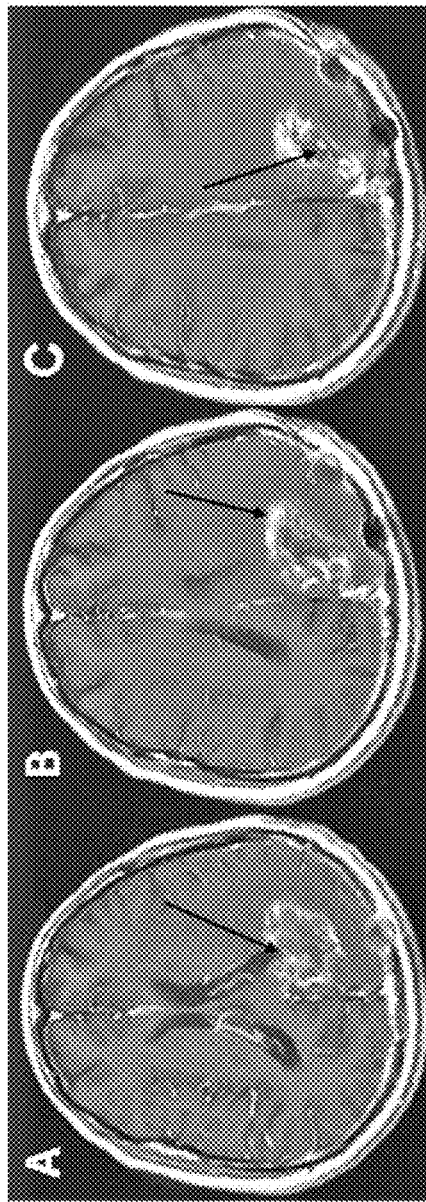
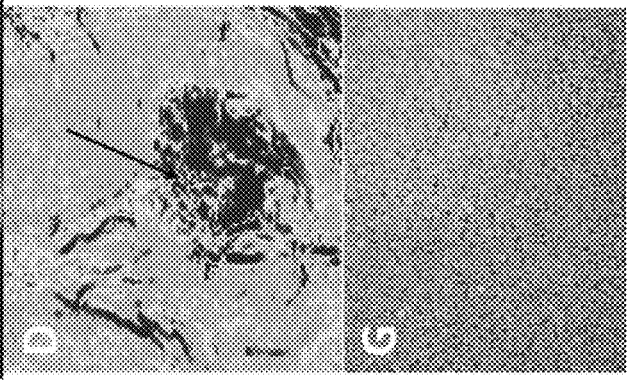
FIG. 3A  FIG. 3B  FIG. 3C
FIG. 3D  FIG. 3E  FIG. 3F
FIG. 3G  FIG. 3H  FIG. 3I

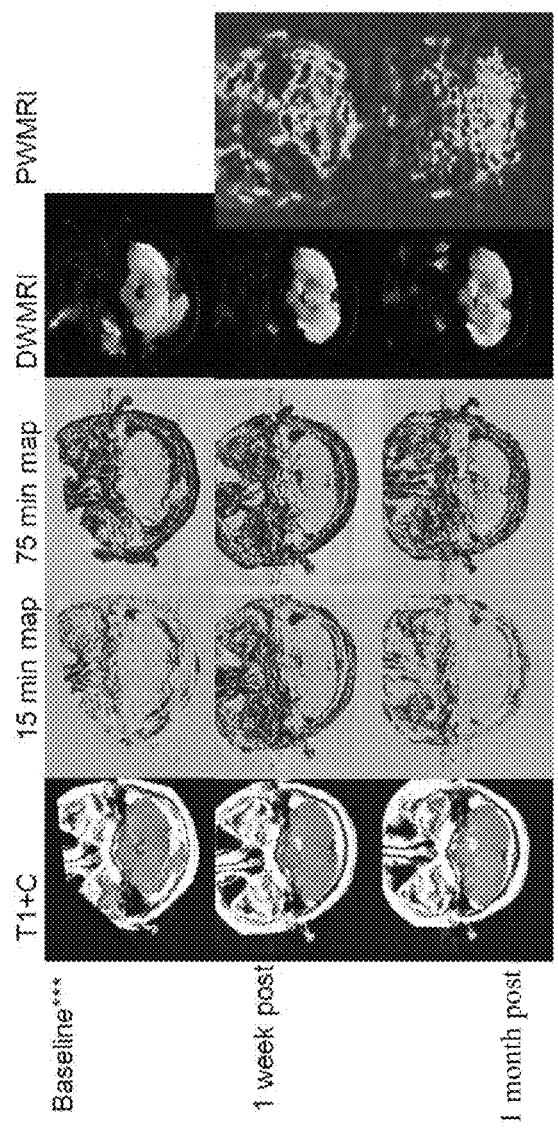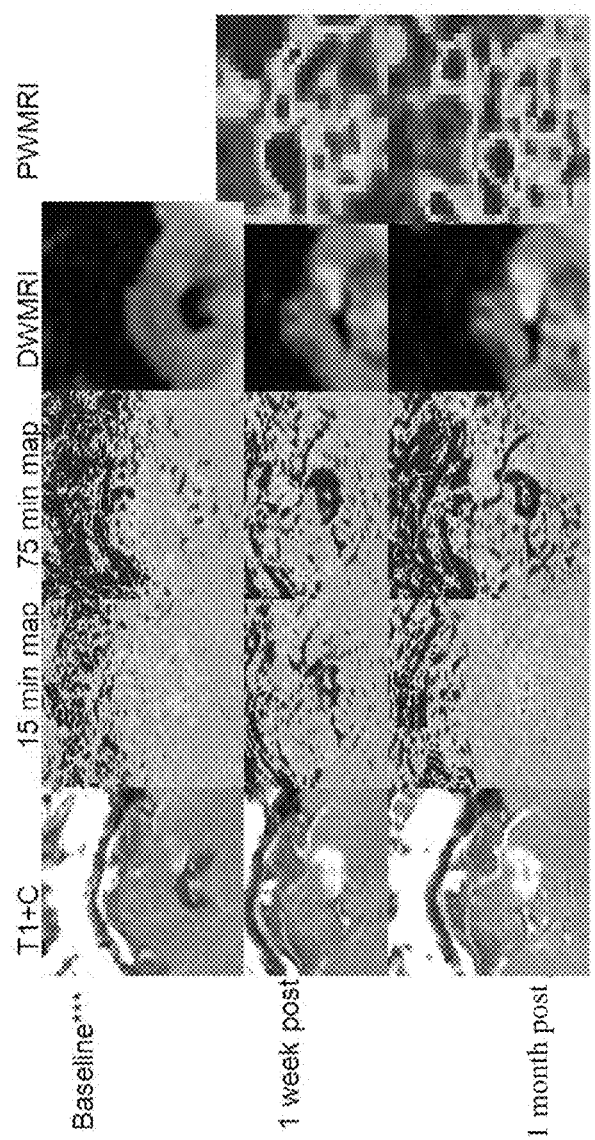

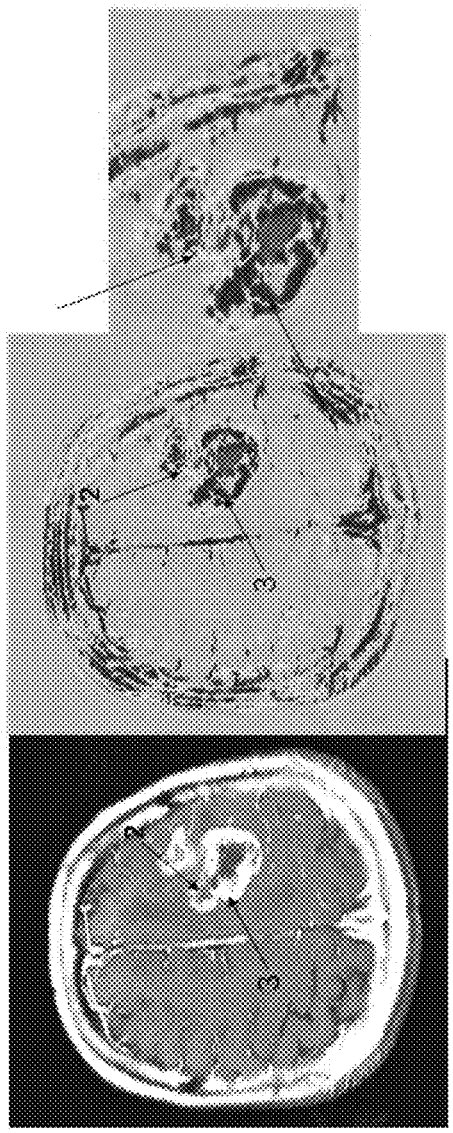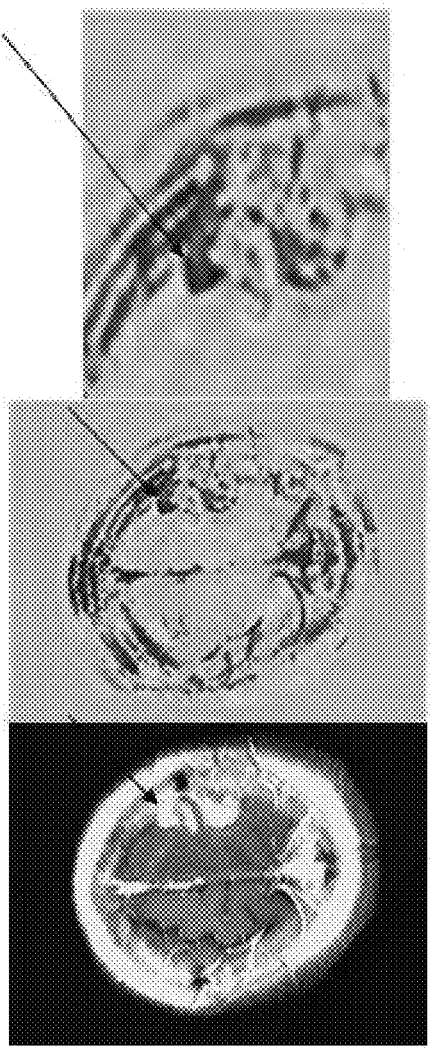

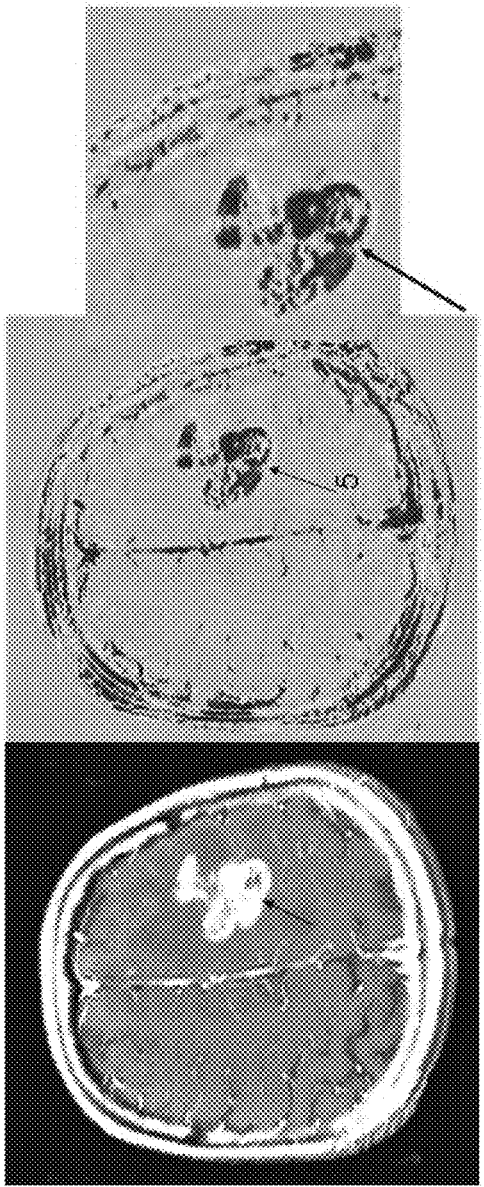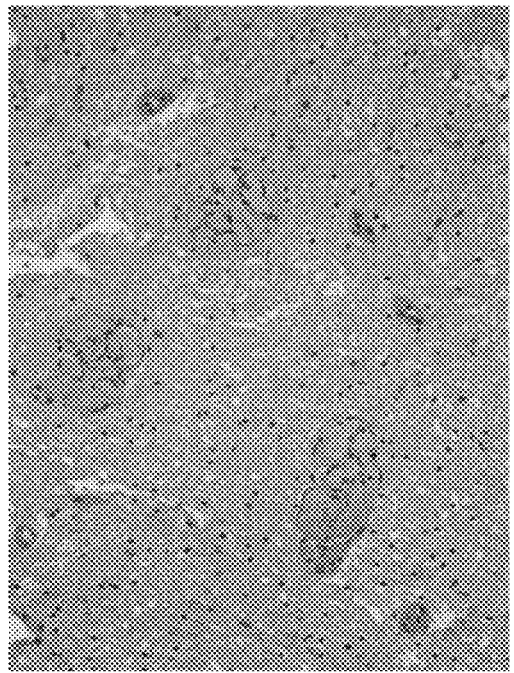
FIG. 21A  FIG. 21B  FIG. 21C
FIG. 22

FIG. 23A  FIG. 23B  FIG. 23C
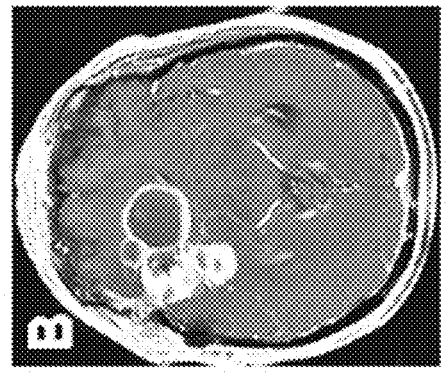
FIG. 23D
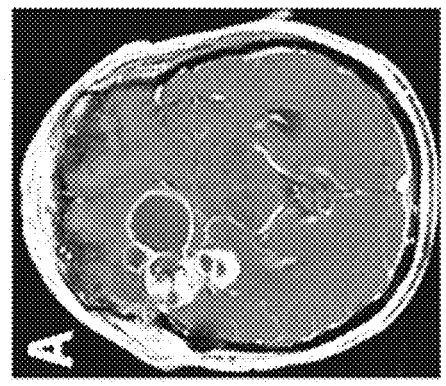
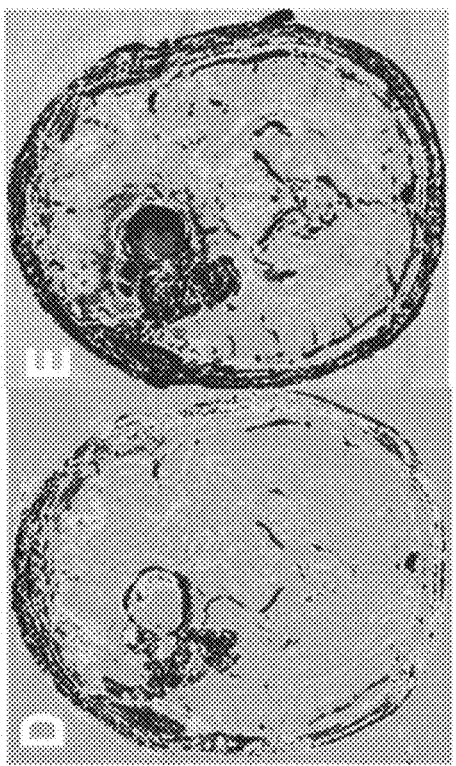
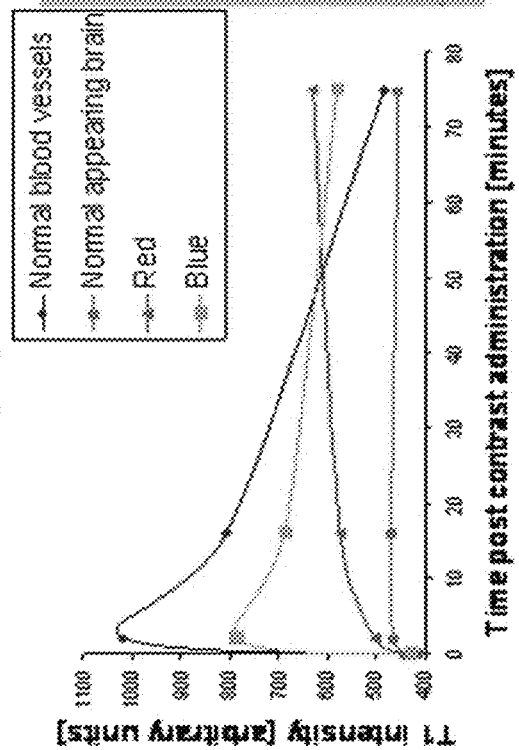
FIG. 23E  FIG. 23F

FIG. 24B
FIG. 24A
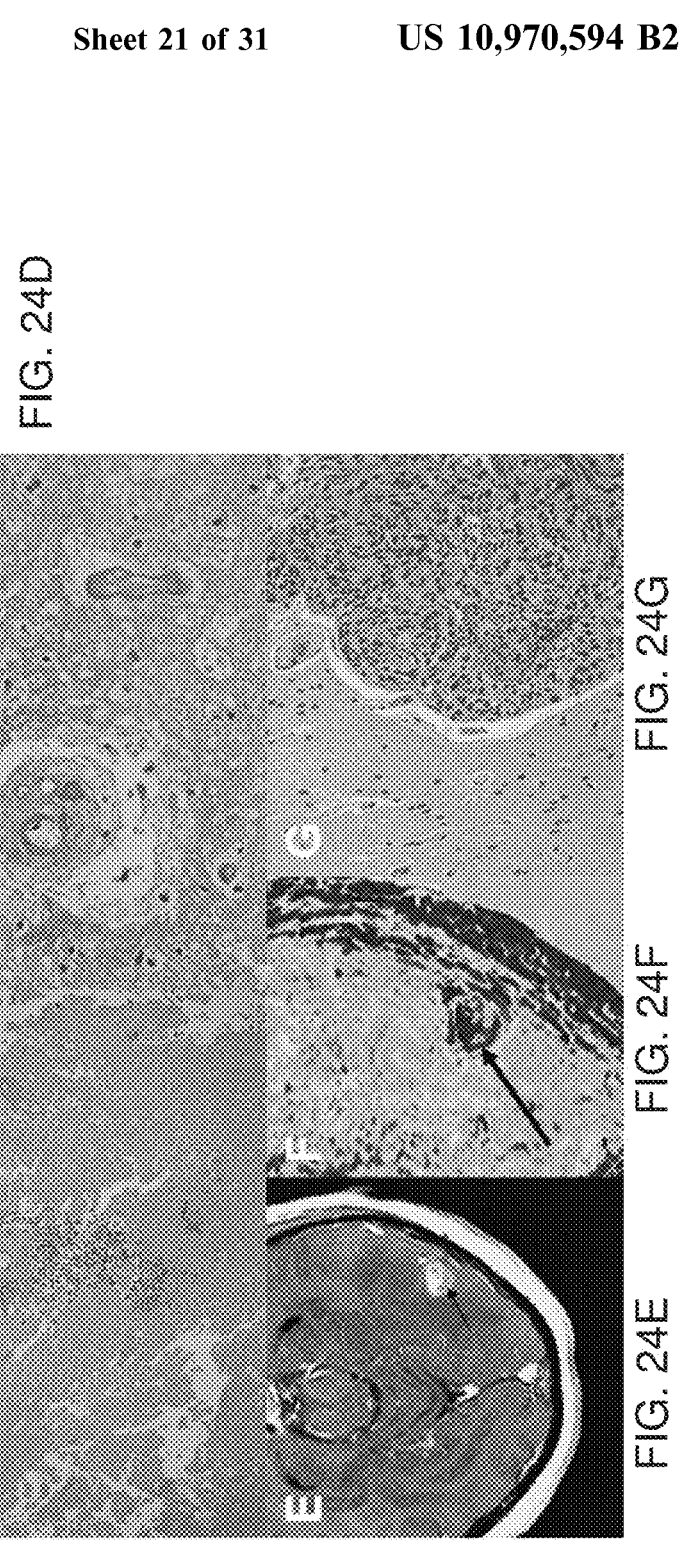
FIG. 24D
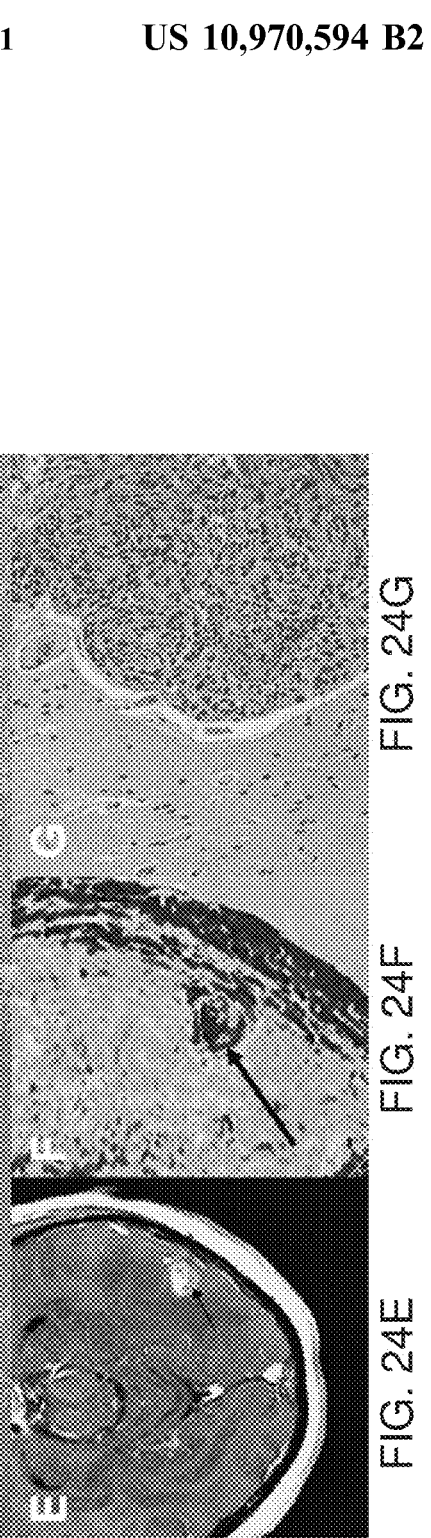
FIG. 24G
FIG. 24F
FIG. 24E
FIG. 24C

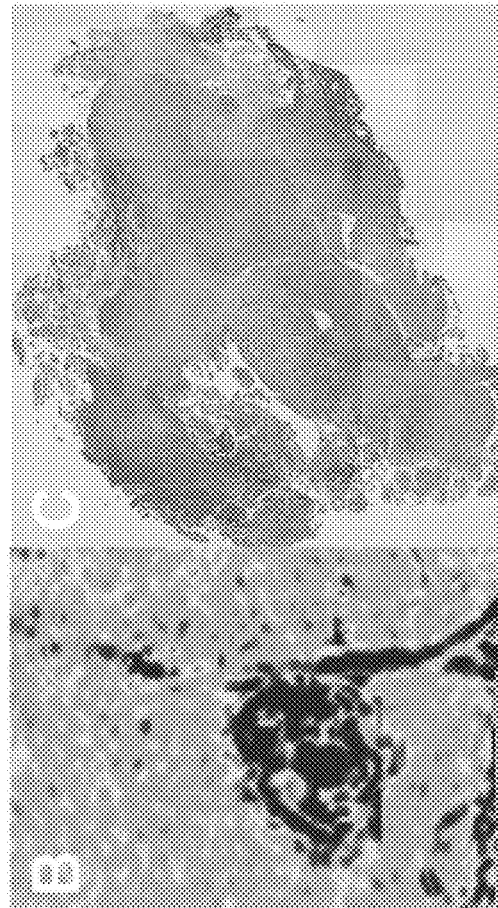
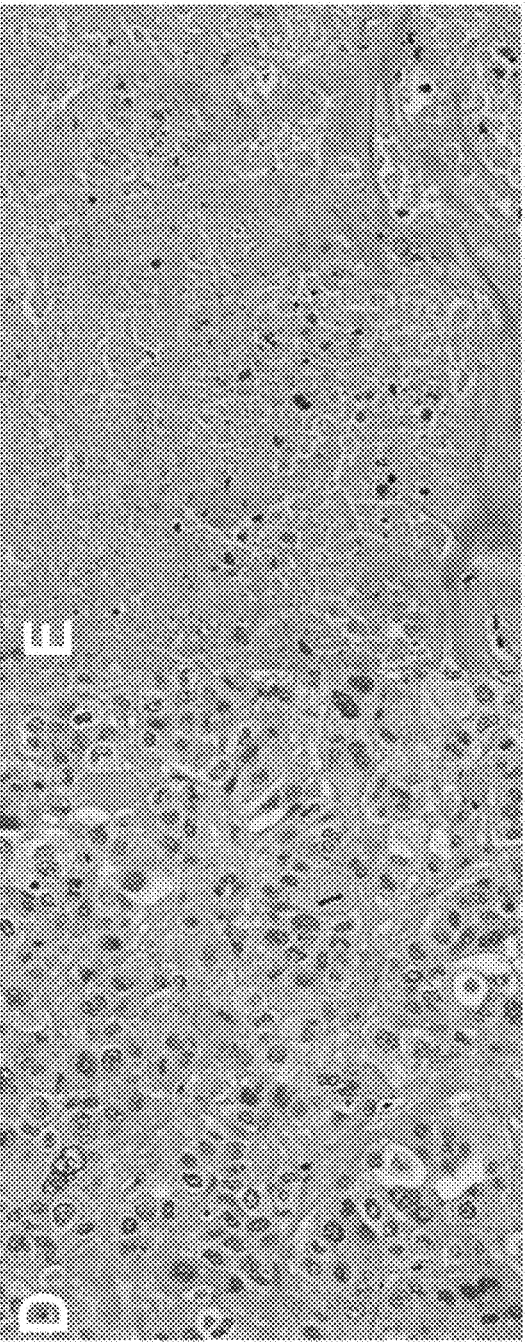
FIG. 25A  FIG. 25B  FIG. 25C  FIG. 25D  FIG. 25E

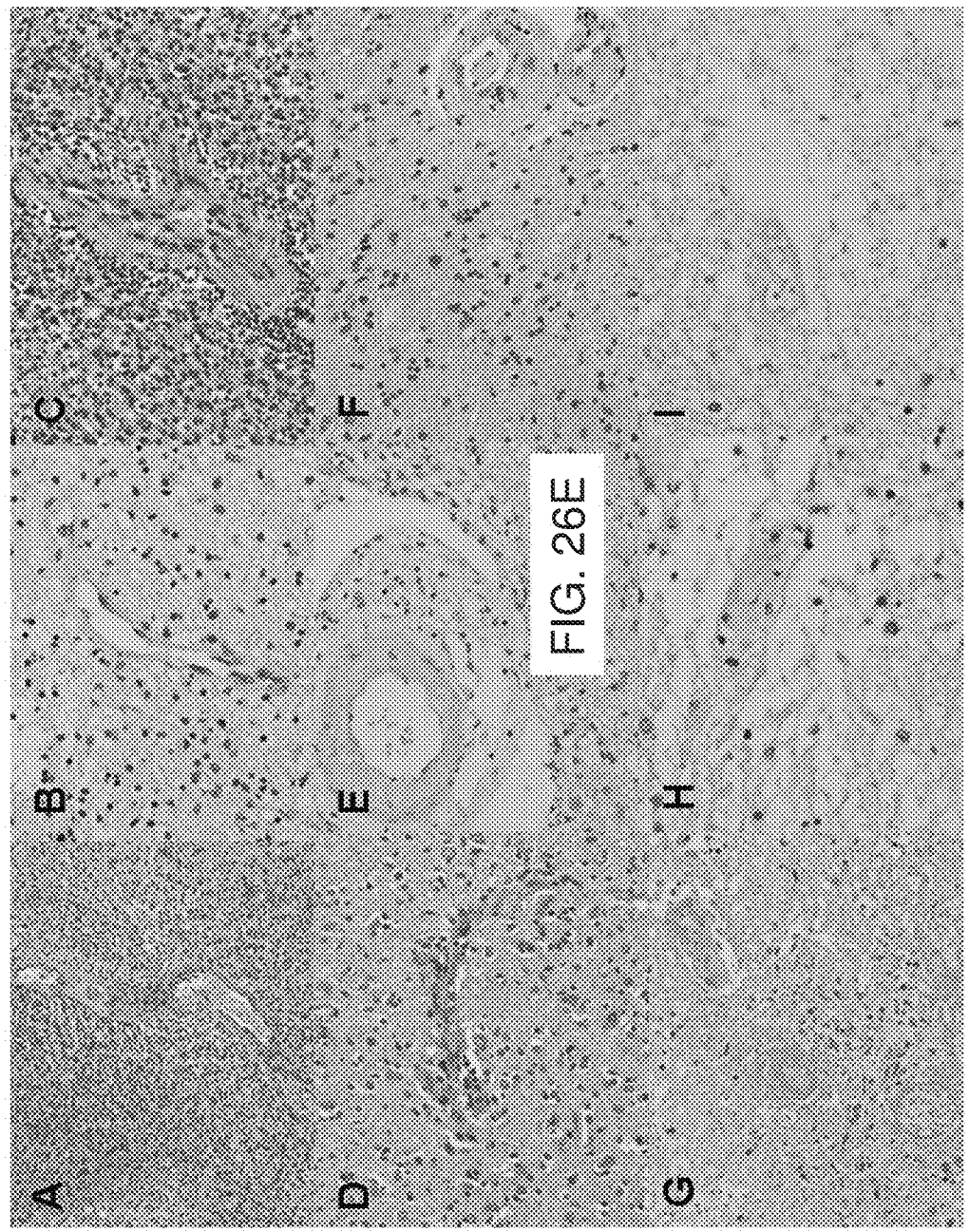

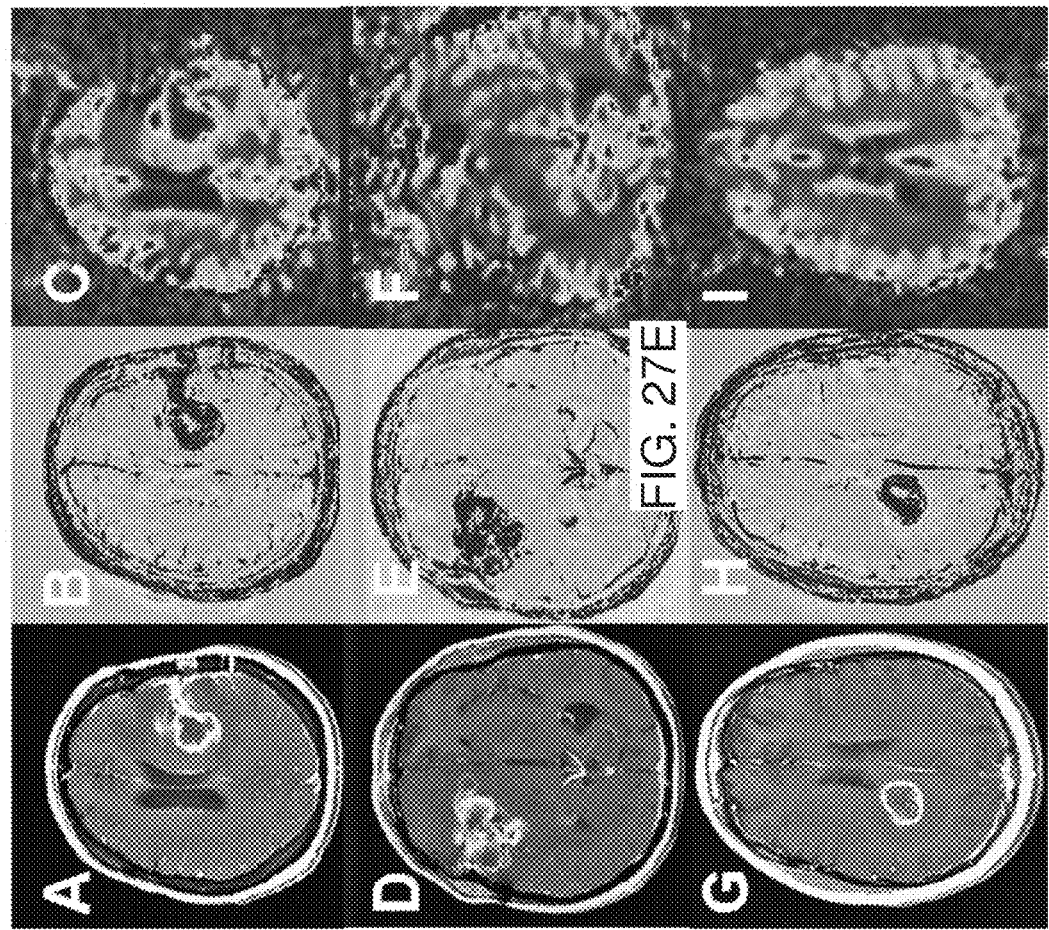

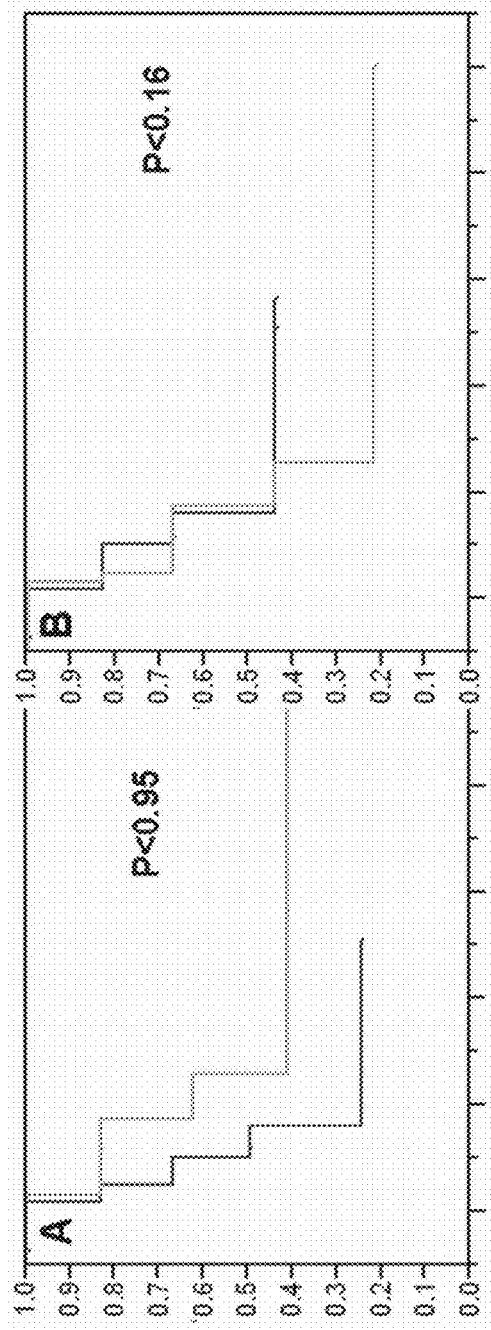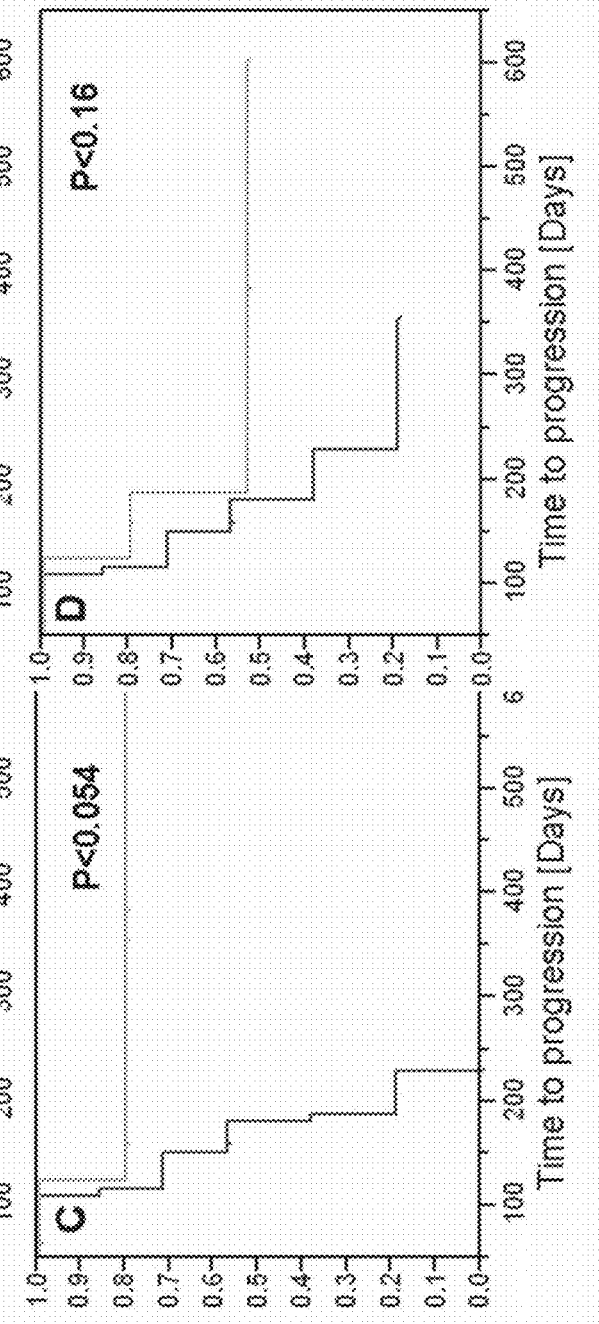
FIG. 28A  FIG. 28B  FIG. 28C  FIG. 28D

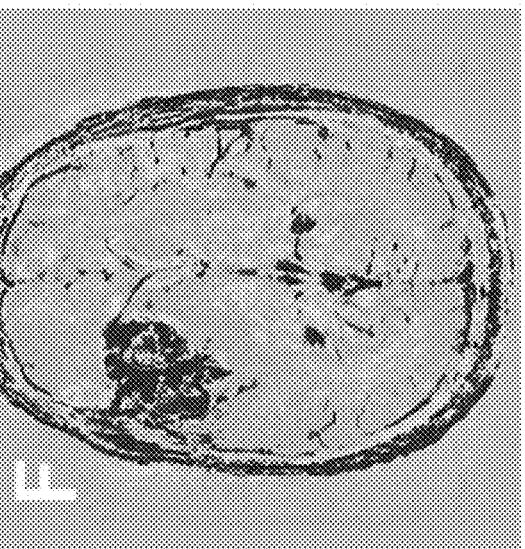
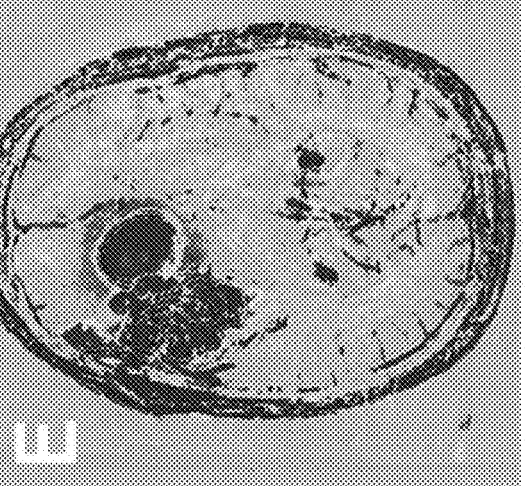
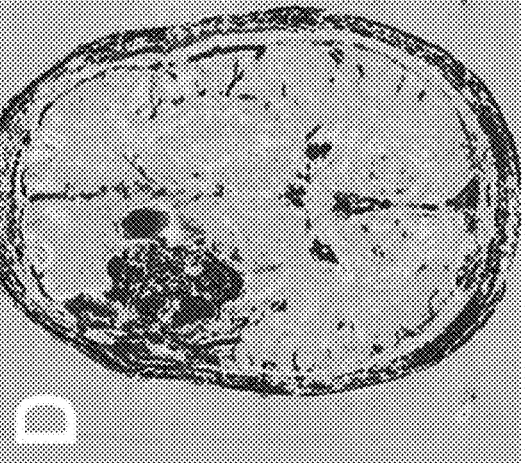

MAGNETIC RESONANCE MAPS FOR ANALYZING TISSUE

RELATED APPLICATIONS

This application is a continuation of U.S. patent application Ser. No. 14/352,099 filed on Apr. 16, 2014, which is a national phase of PCT Patent Application No. PCT/IB2012/055703 having International Filing Date of Oct. 18, 2012, which claims the benefit of priority under 35 USC § 119(e) of U.S. Provisional Patent Application No. 61/548,737 filed on Oct. 19, 2011, the contents of which are incorporated herein by reference in their entirety

FIELD AND BACKGROUND OF THE INVENTION

The present invention relates to method and apparatus for producing magnetic resonance (MR) maps and, more particularly, but not exclusively to using such maps to identify and study tumors, particularly but not necessarily brain tumors.

Gliomas are the most common malignant primary brain tumors in adults, with an annual incidence of 4-5 per 100,000 people (Central Brain Tumor Registry; Wen and Kesari, 2008).

The standard of care for glioblastoma includes chemotherapy during and after radiotherapy. The use of temozolomide (TMZ) both during radiotherapy and for six months post radiotherapy results in a significant increase in median survival with minimal additional toxicity. This treatment regime is now standard for most cases of glioblastoma where the patient is not enrolled in a clinical trial.

Temozolomide seems to work by sensitizing the tumor cells to radiation. The U.S. Food and Drug Administration approved Avastin (bevacizumab) to treat patients with glioblastoma at progression after standard therapy based on the results of 2 studies that showed Avastin reduced tumor size in some glioblastoma patients.

Treatment response assessment of high-grade gliomas is currently based on overall survival or, more commonly in patients with recurrent disease, on progression-free survival (PFS) (Wong et al, 1999; Lamborn et al, 2008), determined from radiographic response. The Macdonald criteria (Macdonald et al, 1990), published in 1990, provided an objective radiologic assessment of tumor response, based on the product of the maximal cross-sectional enhancing diameters as the primary tumor measure. In the Macdonald Criteria, a significant increase (at least 25%) in the contrast-enhancing lesion is used as a reliable surrogate marker for tumor progression, and its presence mandates a change in therapy. However, increased enhancement can also be induced by a variety of non-tumoral processes such as treatment-related inflammation, seizure activity, postsurgical changes, ischemia, sub-acute radiation effects, and radiation necrosis (Van den Bent et al, 2009).

In this context, post-treatment radiographic changes observed within several months of temozolomide-based chemoradiation, have been recently referred to as pseudoprogression. This treatment related effect has implications for patient management and may result in premature discontinuation of effective adjuvant therapy. This limits the validity of a progression free survival end point unless tissue-based confirmation of tumor progression is obtained. It also has significant implications for selecting appropriate patients for participation in clinical trials for recurrent gliomas. Pseudoprogression was widely reported within the last 5 years in glioma patients undergoing standard chemoradiation. These papers demonstrate that 26-58% of the patients depict early disease progression at first post-concomitant chemoradiation imaging. Within those patients which continued treatment, 28-66% showed radiologic improvement or stabilization and were defined retrospectively as manifesting pseudoprogression.

Treatment decision, as whether to operate on a patient with radiographic deterioration, continue chemoradiation or change to another non-surgical treatment is a day to day struggle involving interdisciplinary teams of neurosurgeons, neuro-oncologists and neuro-radiologists who are often unable to reach a unanimous interpretation of the patient status.

For glioblastoma patients treated by radiation and TMZ, conventional MRI is unable to provide a reliable distinction between tumor progression and treatment effects (also referred to as pseudoprogression). For glioblastoma patients conventional MRI is unable to reliable depict the tumor or pseudoprogression after treatment with Avastin.

MRS can distinguish residual or recurrent tumors from pure treatment-related necrosis, but not from mixed necrosis and tumor tissue. Diffusion weighted MRI (DWMRI) has also been assessed for differentiating tumor/necrosis after RT, however, the specificity of DWMRI is less than MRS. It has been suggested that combining DWMRI with MRS may improve the differentiation. FDG-PET has been shown to be useful in differentiating necrosis from recurrence, but the reported sensitivity and specificity were again low. There is limited, but increasing evidence that PET with amino acid tracers can discriminate treatment-related necrosis from tumor recurrence. Whether these techniques will also allow a reliable distinction between pseudoprogression and real progression is yet to be determined.

A number of MRI techniques have been applied to study microvasculature parameters in this context. The two most commonly used methods are dynamic contrast-enhanced MRI (DCE MRI) and dynamic susceptibility-weighted contrast MRI. DCE MRI measures the changes in T1 relaxation associated with disrupted blood brain barrier following contrast administration using parameters such as fractional blood volume (fBV) and permeability (Kps or Ktrans). DSC MRI uses echo planar sequences with a rapid bolus of gadolinium-based contrast agents to assess changes in T2* within the vasculature and interstitial space. Typical calculated parameters are the relative peak height (rPH), relative cerebral blood volume (rCBV) and the percentage recovery (% REC) or recirculation factor (RF).

Parametric maps that are derived from DCE and DSC data have been proposed as noninvasive methods for assessing response to therapy. Radiation necrosis typically shows decreased rCBV, whereas recurrence shows high rCBV. Unfortunately, there was significant overlap between the two groups. More encouraging results were obtained using delayed T1-weighted MRI (T1-MRI) permeability methods, which image beyond the first pass circulation of contrast, sometimes as long as 10-15 min. Using such a delay, one group were able to reliably distinguish between recurrence, radiation necrosis, and a combination of both factors. They found that radiation necrosis and tumor enhance at different rates, enabling significant differentiation between recurrent tumor, radiation necrosis and mixed radiation necrosis and tumor (p<0.001). One group showed that using intra-tumoral and peri-tumoral MRI information it was possible to predict activation of hypoxia and proliferation gene-expression programs, respectively. Furthermore, the intratumoral distribution of gene-expression patterns was found to predict patient outcome.

DSC was recently applied, demonstrating the feasibility for differentiating pseudoprogression from real tumor progression using ferumoxytol. One group applied DCE to a cohort of 29 patients with gliomas and brain metastasis suspected of treatment-induced necrosis or recurrent/progressive tumor and demonstrated the feasibility of predicting real progression. Another group applied DSC MRI for differentiating tumor progression from radiation necrosis in glioblastoma multiforme (GBM) patients undergoing external beam radiation therapy. Their analysis showed that rPH and rCBV were significantly higher in patients with recurrent GBM than in patients with radiation necrosis while the % REC values were significantly lower.

Brain metastases are the most common intracranial tumor in adults, occurring in approximately 10% to 30% of adult cancer patients. It is believed that the annual incidence is rising (due to better treatment of systemic disease and improved imaging modalities). The prognosis of patients diagnosed with brain metastases is generally poor.

Stereotactic radiosurgery (SRS) is a radiotherapy technique which permits the delivery of a single large dose of radiation to the tumor while minimizing irradiation of adjacent normal tissue. It is applied to treat both benign and malignant tumors as well as for vascular lesions and functional disorders. Among the reported complications of SRS is radiation-induced necrosis which, similarly to pseudoprogression, can be difficult to differentiate both clinically and radiologically from recurrent tumor at the treatment site. The incidence of radiation induced necrosis may vary between 5% to 11% according to the volume of the treated lesion and the applied dose (19).

SUMMARY OF THE INVENTION

The background art fail to provide modality to differentiate between brain tumor progression and treatment effects after treating brain pathologies with treatments such as stereotactic radio surgical therapy and chemotherapy and whole brain radiation or the combination of the above. The present inventors devised a technique which, in some embodiments, can help differentiating patients with brain SOL (e.g., brain metastases, primary brain tumors or Arteriovenous malformation) who show radiological progression using conventional imaging methodologies and who have undergone such treatments as listed above and indeed suffer from SOL progression, from patients with treatment effects mimicking SOL progression on conventional imaging. This differentiation is based according to some embodiments of the present invention MR subtraction maps, acquired at the beginning and end of a predetermined time interval post contrast injection.

As used herein "treatment effect" refers to any change attributed to the treatment per se, but not to a progression or retraction of a disease or condition, which mimics progression when using conventional imaging methodologies. For example, for a GBM patient, "treatment effect" refers to pseudoprogression, and for a patient with brain metastases "treatment effect" refers to radiation necrosis.

Without wishing to be bound to any particular theory, the present inventors hypothesize that these maps present a unique pattern for treatment effects and can be useful for the differentiation between treatment effects and SOL progression. The ability to differentiate between these pathological patterns is of major significance as the treatment given is different: for treatment effects a course of steroids treatment is usually enough while patients with tumor or AVM progression might need a surgical intervention or another change of treatment.

The current standard of care for treatment effects post radio surgical treatment is follow up with steroids with imaging and clinical follow up while suspected tumor progression may require tumor resection. Similarly the current standard of care for treatment effects of GBM patients with pseudoprogression post chemoradiation is to maintain the TMZ treatment with or without steroids treatment with imaging and clinical follow up while tumor progression may require tumor resection or switching to another line of therapy such as Avastin.

Tumor progression has been defined radiologically and clinically, while treatment effects is more difficult to define and is a result of complex, dynamic interplay between tissue, endothelial and glial cells within the irradiated volume. Injury to the vasculature, caused by clonogenic death of endothelial cells that is mainly membrane-damage dependent and less DNA-damage dependent, is thought to be crucial for the development of acute and sub acute RT injury. It is also more likely that the incidence of treatment effects mimicking tumor progression increases with higher RT dose and with the addition of chemotherapy.

Conventional MR imaging is currently unable to provide reliable distinction between suspected tumor progression and treatment effects such as treatment-related necrosis. Another population of patients undergoing radio surgery are patients with Arteriovenous malformation (AVM) which might be more susceptible to radiation necrosis after embolization.

Blood brain barrier disruption is an early pathophysiological event occurring after RT injury, is detectable in vivo/in vitro by MRI and other imaging modalities, and appears to precede white matter necrosis. It has been shown in patients with low grade tumors undergoing RT that blood brain barrier permeability increased up to 40-50% in the regions exposed to high doses of RT. An in vivo model in mice correlated histological vascular permeability and quantitative MR assessment.

The present inventors realized that although first-pass perfusion MRI is more accurate than T1-MRI for differentiating between tumor progression and treatment effects, it is not without certain limitations that would best be avoided. Treatment effects such as pseudoprogression and radiation necrosis typically show decreased relative cerebral blood volume (rCBV), whereas tumor recurrence results in high rCBV.

In various exemplary embodiments of the invention a subtraction map is a map that is calculated by subtracting an early image, which is optionally and preferably acquired early post contrast administration, from a later image which is acquired a predetermined time period after the earlier image, wherein said predetermined time period is at least twenty minutes.

According to one aspect of the present invention there is provided apparatus for analyzing brain MRI, comprising an input for receiving a first and a second MRI series at the beginning and end of a predetermined time interval post contrast administration, a subtraction map former for forming a subtraction map from the first and the second MRI series by analyzing the series to distinguish between two primary populations, a slow population, in which contrast clearance from the tissue is slower than contrast accumulation, and a fast population in which clearance is faster than accumulation; and an output to provide an indication of distribution of the two primary populations, wherein the predetermined time period is at least twenty minutes.

In some embodiments of the present invention the primary populations are vessel function populations.

In some embodiments of the present invention the maps are vessel function maps.

The apparatus can also comprise an intensity map constructor for constructing, for each magnetic resonance image, an intensity map. In these embodiments the subtraction map describes variations in concentration of the contrast agent in the brain by detecting dissimilarities among a pair of intensity maps.

In an embodiment, the predetermined time period is any one of the group consisting of: more than twenty minutes, more than thirty minutes, more than forty minutes, more than fifty minutes, more than sixty minutes, more than seventy minutes, more than eighty minutes, more than ninety minutes, more than a hundred minutes, seventy minutes, seventy five minutes and ninety minutes.

In an embodiment, the map former is configured for assigning a representative intensity value for each magnetic resonance image and determining a time-dependence of the representative intensity value.

In an embodiment, the map former is configured for generating a graph describing the time-dependence.

In an embodiment, the input is configured to receive high resolution spin-echo T1-weighted MR images (T1-MRIs).

In an embodiment, the map former is configured for assessing, from the subtraction map, whether tumor tissue is present, by comparing drainage of the contrast agent from blood vessels with contrast agent take up in the tissue.

In an embodiment, the subtraction map former is configured for differentiating between morphologically active tumor represented by the fast population, and a non-tumoral tissue represented by the slow population.

An embodiment may carry out image pre-processing, the preprocessing comprising a) correction for intensity variations and b) whole body image registration.

In an embodiment, the correction for intensity variations comprises calculating, for each MRI image separately, an intensity variation map consisting of large scale intensity variations therein and then subtracting the intensity variation map from the respective image.

An embodiment may comprise a registration unit for carrying out registration between corresponding MRI images, the registration comprising at least one of a rigid registration to allow for head movements between respective series and an elastic registration to correct for image distortion related to the head movements.

In an embodiment, the elastic registration comprises dividing each slice of a respective series into to a grid of volumes, and allowing each volume to move freely in three dimensions until a sum of the absolute values of the intensity difference between the two time points reaches a minimum.

An embodiment may comprise a smoothing and interpolation unit for smoothing a 3 dimensional translation matrix resulting from the elastic registration using circular smearing, and interpolating to obtain translation values per pixel.

An embodiment may be used for depiction of brain tumors after treatment with anti-angiogenic treatments and studying the mechanism of action and response patterns of brain tumors to anti-angiogenic drugs.

An embodiment may be used for depiction of brain disorders after treatment with radiation-based treatments, for differentiation between tumor progression and radiation necrosis.

Delayed extravasation MRI may be used for differentiation between progression of brain space occupying lesion (SOL) and treatment effects following radio-surgical treatment.

In an embodiment of the present invention, the MRI is of a subject diagnosed with GBM, wherein the subtraction map former is configured to identify increment in a volume of the fast population volume, and wherein the output is configured to indicate progression when the increment is above a predetermined threshold.

According to a second aspect of the present invention there is provided a method for analyzing brain MRI, comprising:

receiving a first and a second MRI series at the beginning and end of a predetermined time interval post contrast administration;

forming a subtraction map from the first and the second MRI series by analyzing the series to distinguish between two primary populations, a slow population, in which contrast clearance from the tissue is slower than contrast accumulation, and a fast population in which clearance is faster than accumulation; and providing an indication of distribution of the two primary populations, wherein the predetermined time period is at least twenty minutes.

In the maps of some embodiments of the present invention, progression is reflected by a significant increase in the fast component of the enhancing lesion while pseudoprogression is reflected by an increase in the slow component with no significant increase in the fast component. Thus, using the maps of the present embodiments in routine MRI follow-up may aid the physician in determining progression versus pseudoprogression in patients presenting an increase in the enhancing lesion on T1-MRI. An increase in the fast component volume, suggesting progression, implies that a change in the current therapy should be employed. No significant increase in the fast volume component, suggesting pseudoprogression, implies that the patient is responding to the current therapy and thus continuation is preferred, if possible.

The maps of the present embodiments may be applied in a similar manner to patients following SRS. For example, patients with growing volumes of the slow component can be recommended for follow-up, if possible, while patients with growing volumes of the fast component can be recommended for treatment such as surgery or repeated SRS.

The ability of the maps of the present embodiments to depict morphologically active tumor regions with high resolution can be applied for optimizing radiation treatment planning by localizing the treatment to the fast/blue regions in the maps. This methodology can optionally and preferably be applied in post surgery scenario to allow differentiation between post surgical changes and tumor remnants thus allowing depicting and treating residual tumor post surgery.

High resolution depiction of tumoral tissues can also be beneficial in the planning of surgical resections, especially in the case of close proximity to functionally eloquent brain regions. In these cases, determination of the exact extent of the tumor can be advantageous for the decision whether microsurgical tumor removal might be warranted.

The maps of the present embodiments may also be applied for guiding stereotactic biopsies for molecular classification of the tumor. In this case the maps may aid in preventing the acquisition of biopsies with a high amount of necrosis or out of the infiltration zone with 'contamination' of the specimen by normal brain tissue, both potentially leading to false-negative results.

Novel approaches for local drug delivery including injections, infusions, trans-nasal delivery, convection enhanced delivery, local BBB disruption and various types of polymeric implants may also benefit from the application of the maps of the present embodiments, for example, for the purpose of planning and monitoring the treatments.

Increased tumor vascularity has been shown to correlate with both shortened survival and higher grade of malignancy in gliomas. Consequently, anti-angiogenic agents such as Bevacizumab, a monoclonal antibody targeting vascular endothelial growth factor, are now commonly employed to treat progressive malignant gliomas. The wide-spread use of these agents has added a layer of complexity to the evaluation and characterization of malignant gliomas as these agents have been shown to rapidly and markedly decrease contrast enhancement on contrast-enhanced T1-MRI. Example 5 below describes a study in which the subtraction maps of the present embodiments are applied for to recurrent GBM patients treated by Bevacizumab.

The high sensitivity of the maps of the present embodiments can provide additional information for delineation of the tumor borders as well as for targeting stereotactic biopsies. The results presented herein demonstrate the applicability of the technique of the present embodiments in the daily clinical scenario. The ability to clearly differentiate tumor from non-tumoral tissues provides the physician with a clear understanding of the patient current situation thus enabling improved patient management.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Implementation of the method and/or system of embodiments of the invention can involve performing or completing selected tasks manually, automatically, or a combination thereof. This refers in particular to tasks involving the control of the spectral equipment.

Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a simplified block diagram showing imaging apparatus for producing subtraction maps according to an embodiment of the present invention;

FIG. 1B is a simplified block diagram showing the subtraction map former of FIG. 1A in greater detail;

FIG. 1C is a simplified block diagram showing the preprocessor and registration unit in greater detail;

FIGS. 1D and 1E are flowchart diagram describing a procedure for constructing subtraction maps, according to some embodiments of the present invention.

Figure 2A:
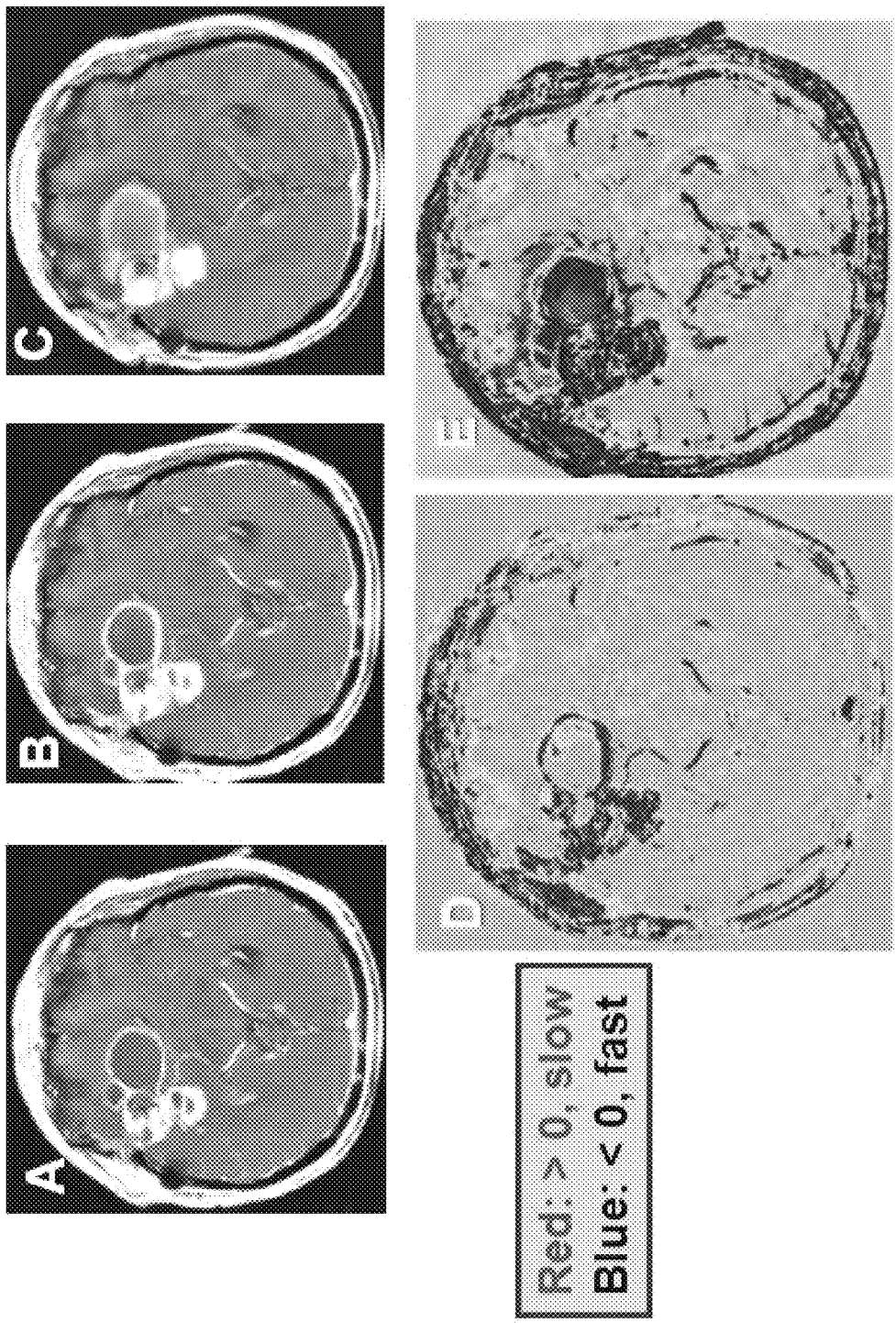
Figures 4A, 4B, 4C, 4D:
Figure 5:
Figure 6:
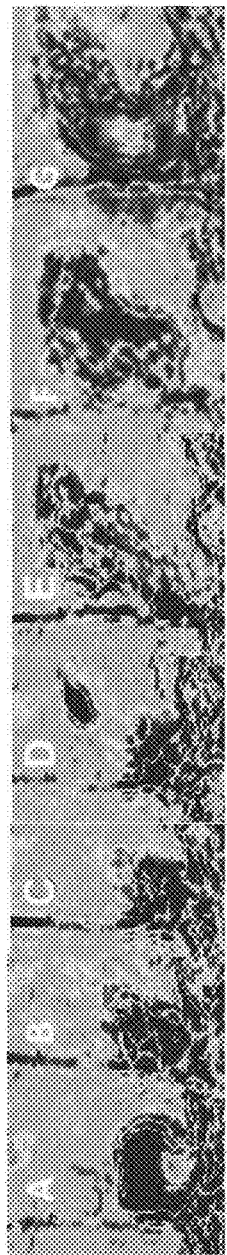
Figure 7:
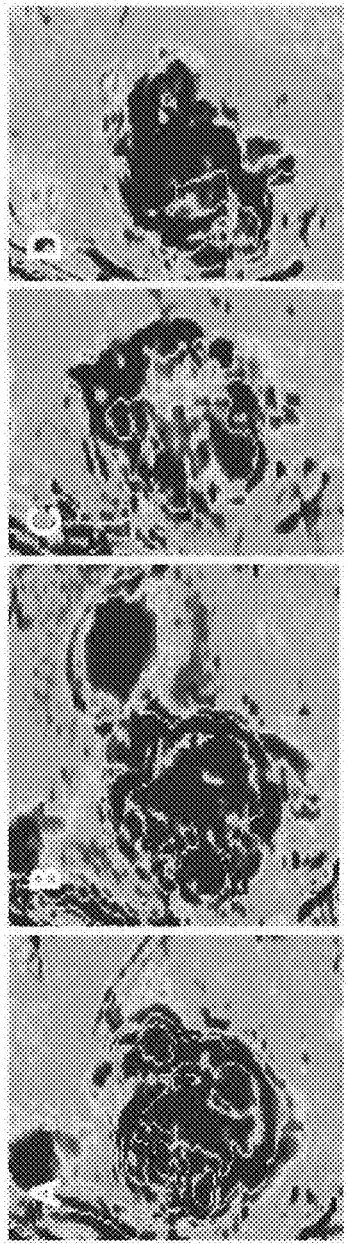
Figure 10:
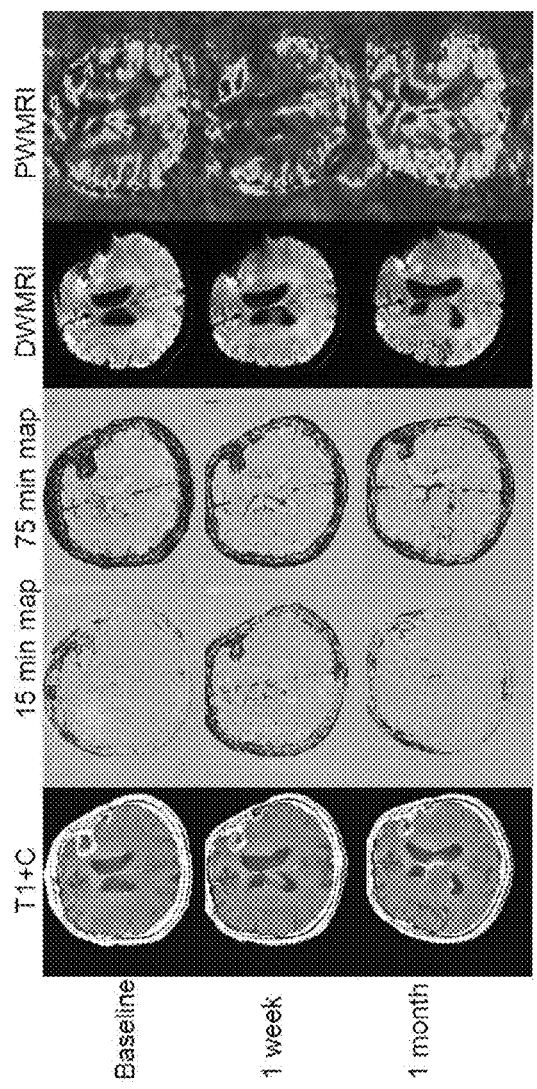

FIG. 2A shows axial high resolution T1-weighted MRI acquired 2 min (A), 15 min (B) and 75 min (C) after contrast administration in a patient with newly diagnosed GBM undergoing standard chemoradiation. Subtraction maps were calculated from the data acquired at 2 and 15 min (D) and 2 and 75 min (E) post contrast administration. It can be seen that abnormal vessel function in the 75 min map is depicted more clearly and in larger regions than in the 15 min map;

FIG. 2B shows axial high resolution T1-weighted MRI acquired 2 min (A), 15 min (B) and 75 min (C) after contrast administration in a patient with newly diagnosed GBM undergoing standard chemoradiation. The calculated map (D) depicts the blue and red components of the tumor. The signal intensity of the different vessels function components as a function of time post contrast administration is shown in the plot below. It can be seen that the blue and red components of the tumor enhance and decay at different rates;

FIGS. 3A-3I show contrast-enhanced T1-weighted MRI (A-C), subtraction maps calculated from the 2 and 75 min data (D-F) and H&E stained histological samples (G, H, I) of a rapidly growing lesion in a patient with newly diagnosed GBM undergoing standard chemoradiation. Data was acquired 3 days prior to surgery, 6 months after initiation of treatment. Samples were taken from a mixed blue and red region (A, D, arrows), a blue region (B, E, arrows) and a red region (C, F, arrows). Histological analysis reveals mixed regions of tumor and necrosis (G, magnification ×200), hypercellular tumor (H, magnification ×400) and radiation necrosis (J, magnification×400), respectively;

FIGS. 4A-4D show the enhancing of a portion of the lesion: Contrast-enhanced T1-weighted MRI without (A) and with (B) a mask selecting the enhancing portion of the lesion on conventional MRI. The enhancing portion of the lesion was calculated from the pixels marked pink in (B). Subtraction maps calculated at 15 min (C) and 75 min (D) demonstrate the contributions of the red/non-tumor and blue/tumor contributions to the enhancing portion of the tumor;

FIG. 5 shows subtraction maps of five patients three weeks after chemoradiation. The lesions of these patients are characterized by a blue intense rim surrounding a cystic region;

FIG. 6 shows subtraction maps of a patient, calculated 0.7, 2.5, 3.5, 6.1, 7.6 and 8.1 (A-F) months after chemoradiation and after a second resection (G). The maps show significant increase in the blue component of the tumor in the last two follow-ups prior to surgery. Map G was calculated from MR images acquired one month after resection;

FIG. 7 shows subtraction maps of a patient calculated 0.7, 2.5, 4.4 and 6.1 months after chemoradiation, showing significant increase in the blue component of the tumor with no significant increase in the enhancing portion of the lesion on conventional MRI;

FIG. 8 shows a GBM lesion of a patient in example 2 at baseline (top), 1 week after Avastin treatment (middle) and 1 month after treatment (bottom). It can be seen that the lesion became more prominently blue after the first week of treatment with minor changes in the 1 month follow-up;

FIG. 9 is a zoomed view of FIG. 8;

FIG. 10 shows recurrent GBM lesion (post surgery and standard chemoradiation) of a patient in example 2 at baseline (top), 1 week after Avastin treatment (middle) and 1 month after treatment (bottom). It can be seen that in this lesion there was a decrease in the blue component in the first week post treatment and then an increase 1 month later.

Figure 11:
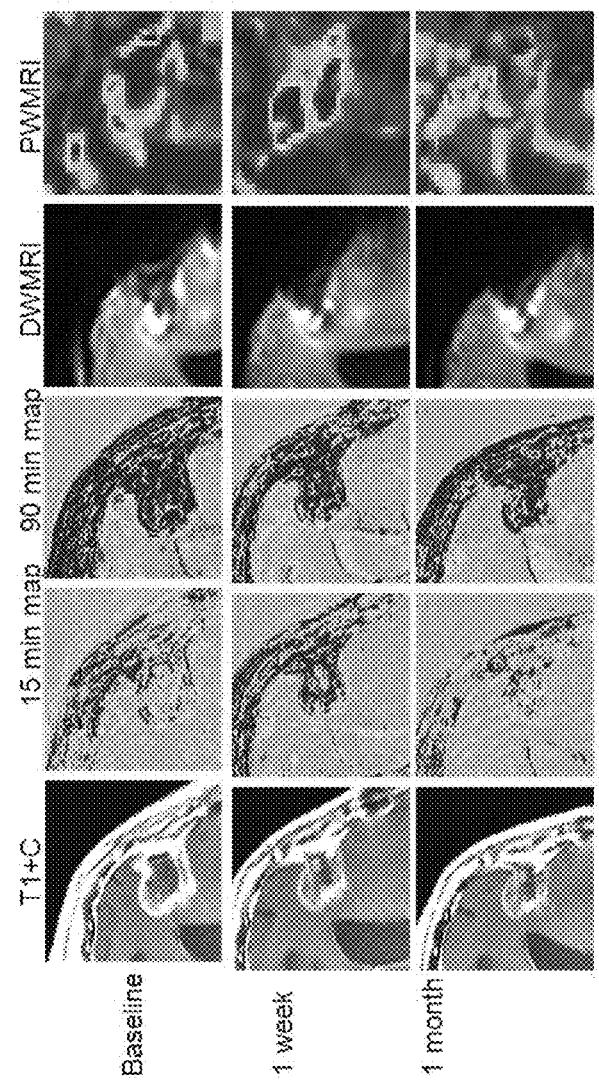
Figure 12:
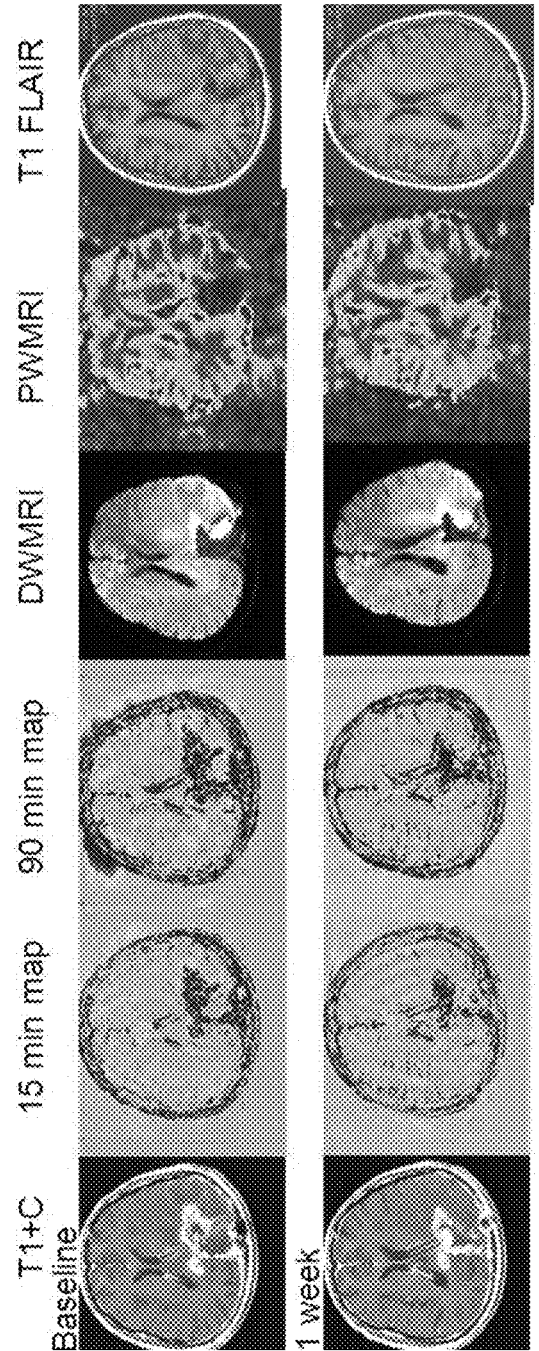

FIG. 11 is a zoomed view of FIG. 10;

FIG. 12 relates to a patient in example 2, who was recruited after failing standard chemoradiation and 1 month after undergoing a second resection. His tumor induced significant edema and pressure on adjacent brain as shown in the baseline MRI (top). 1 week after the first treatment with Avastin, it can be seen that the pressure on the brain is relieved, the edema is somewhat relieved as well, the red component of the lesion has significantly decreased but the blue component seems more concentrated, and has not decreased. The blue component of this tumor continued to increase in his 3-months follow-up in parallel to clinical deterioration with no sign of progression on conventional MRI.

Figure 13:
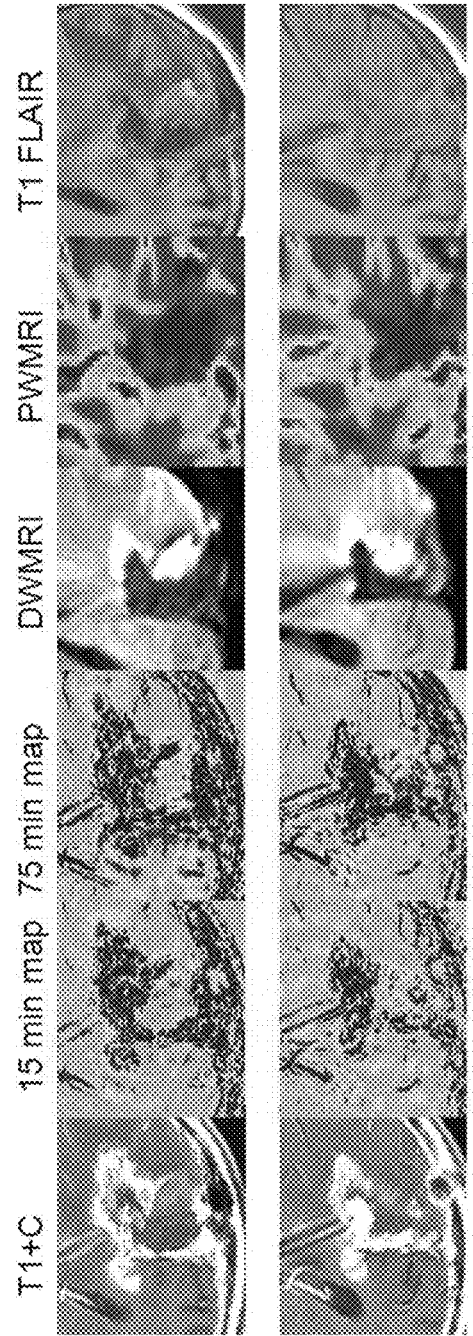

FIG. 13 is a zoomed view of FIG. 12.

Figure 14:
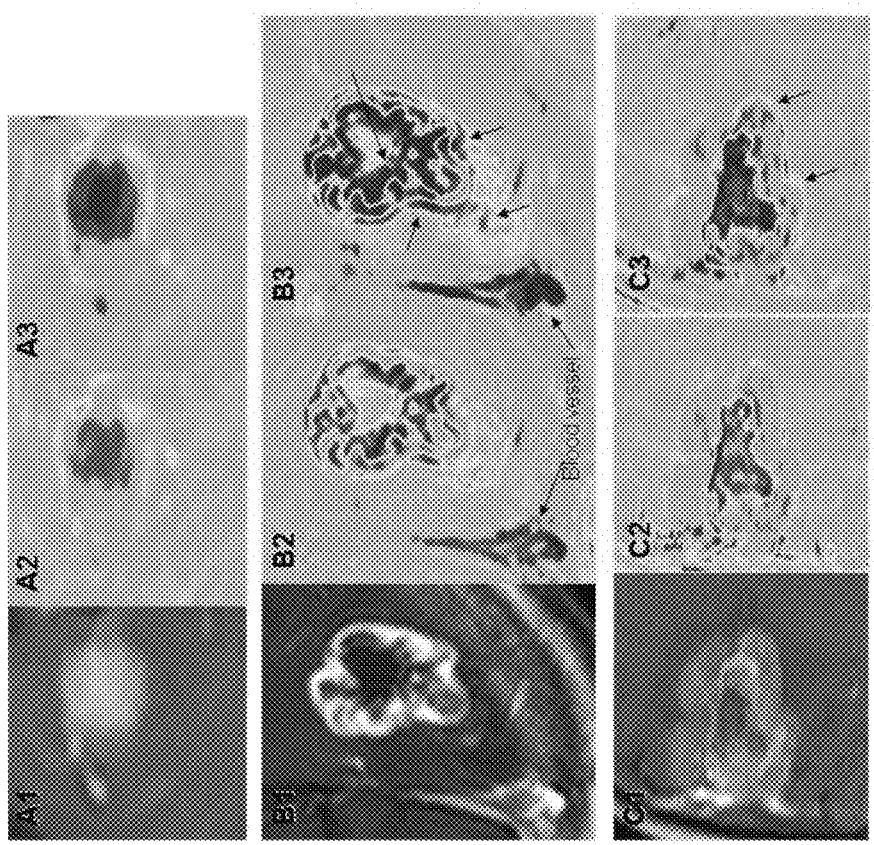

FIG. 14 shows 3 brain metastases and maps calculated from short delays: A1, B1 and C1 are the contrast-enhanced MRIs of the 3 metastases; A2, B2 and C2 are maps calculated using the 2 min and 7 min MRIs and A3, B3 and C3 are maps calculated using the 2 min and 14 min MRIs.

Figure 15:
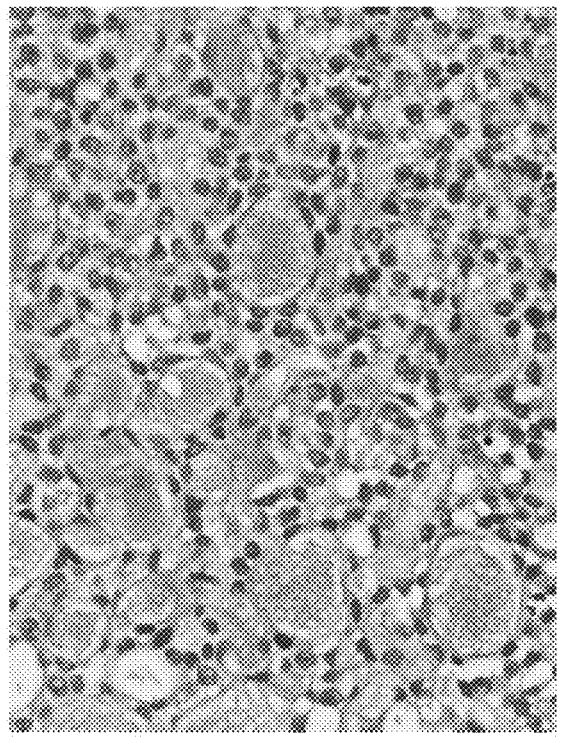

FIG. 15 shows histology corresponding to the blue regions of the map shown in FIG. 17 below.

Figure 16:
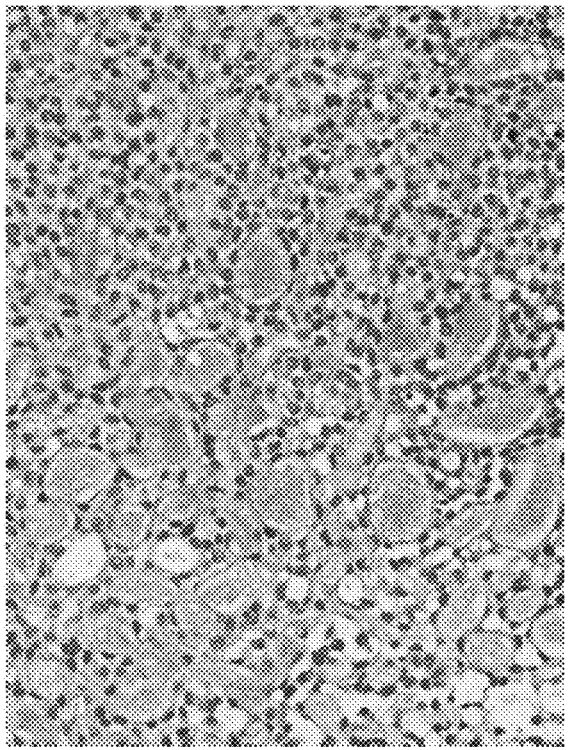

FIG. 16 shows histology corresponding to the map shown in FIG. 18C.

FIG. 17A shows contrast-enhanced MRI of a Adenoid cystic carcinoma brain metastases (pointed by arrows 2 and 3).

FIG. 17B is the corresponding subtraction map calculated from the 2 min and the 75 min MR images showing part of the metastases in which approximately 60% is determined by the maps to consist of morphologically active tumor (blue), and approximately 40% is non-tumoral tissues consisting of tumor necrosis and treatment effects (red). The arrows correspond to the arrows shown in FIG. 17A.

FIG. 17C shows a zoomed presentation of FIG. 17B. The arrows point to the same locations as in FIG. 17B.

Figure 19:
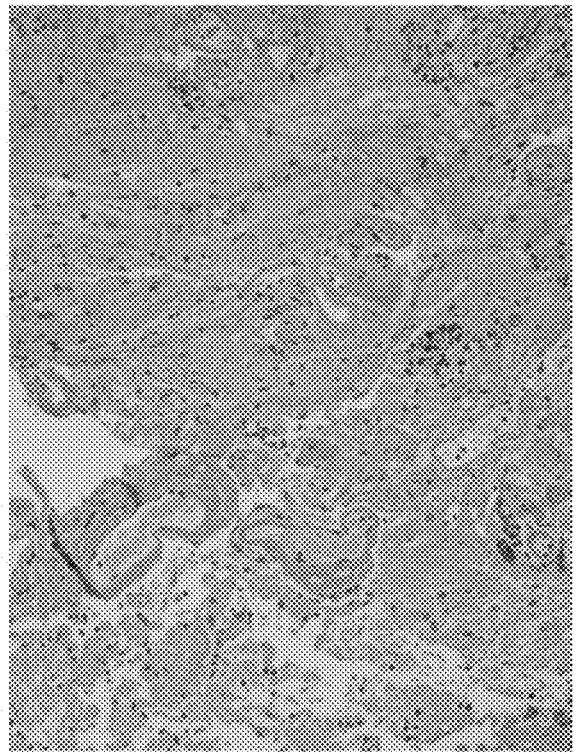

FIGS. 18A to 18C are similar to FIGS. 17A to 17C but instead show the base or posterior part of the tumor (pointed by an arrow);

FIG. 19 shows histology corresponding to the red region in map shown in FIGS. 17B and 17C.

Figure 20:
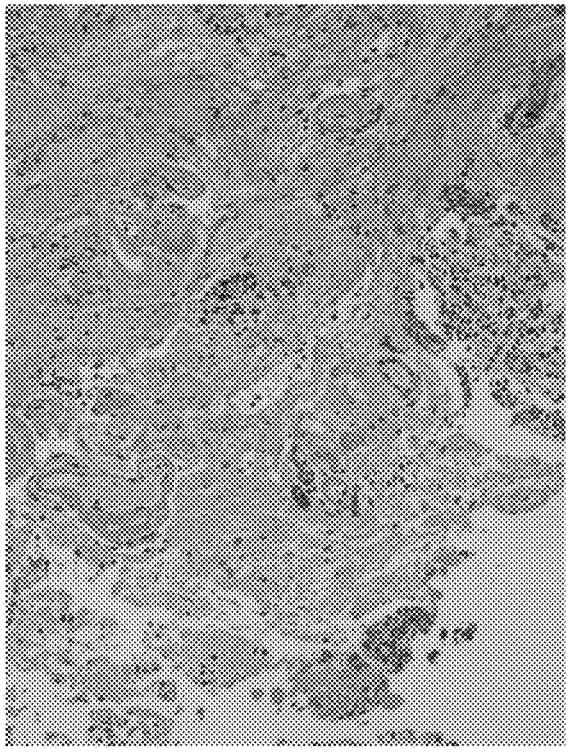
Figure 30A:
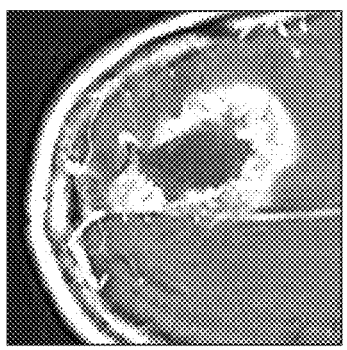
Figure 30B:
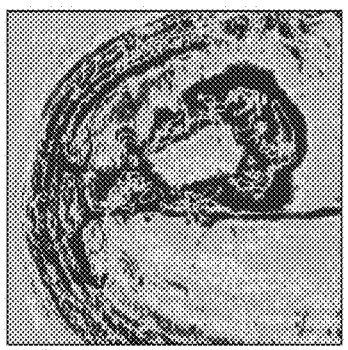
Figure 30C:
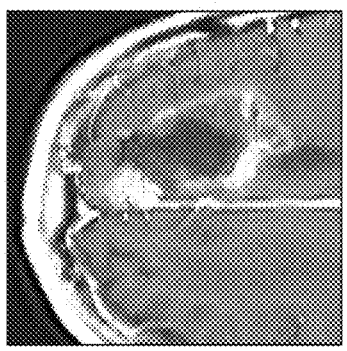
Figure 30D:
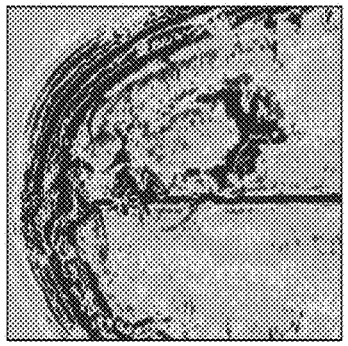
Figure 30E:
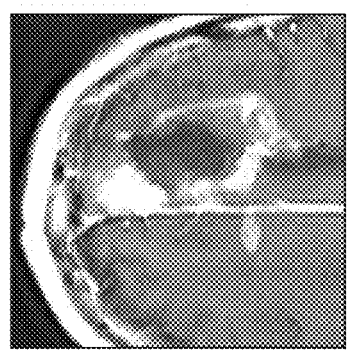
Figure 30F:
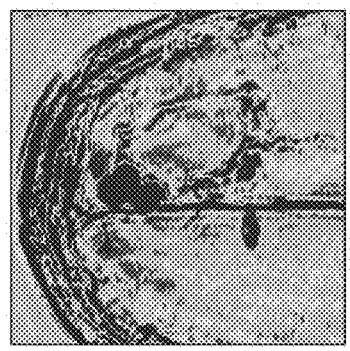

FIG. 20 shows additional histology corresponding to the red region in the map shown in FIGS. 17B and 17C.

FIGS. 21A-21C show another slice of the same tumor (pointed by arrow 5 on FIG. 21B, and by unnumbered arrows on FIGS. 21A and 21C).

FIG. 22 shows histology corresponding to a blue region in FIGS. 21B-21C.

FIGS. 23A-23F show examples of 15 and 75 min subtraction maps.

FIGS. 24A-24G show histological determination of tumor and non-tumoral components—brain metastases. Examples of contrast-enhanced T1-weighted MRI (A, E), enhancement subtraction maps calculated from the 2 and 75 min data (B, F) and H&E stained histological samples (C, D, G) of a cortical breast cancer brain metastasis. 24C and 24D show a necrotic region taken from the red region of the map shown in 24B (arrow). 24D shows tumoral tissue on the border of normal cortex, taken from a region of blue on the border of normal brain, pointed to by an arrow in image 24F.

FIGS. 25A-25E show histological determination of tumor and non-tumoral components—brain metastases. Examples of contrast-enhanced T1-weighted MRI (A), enhancement subtraction map calculated from the 2 and 75 min data (B), macro H&E stained histological sample (C, magnification ×20), tumor region from a peripheral region of the sample (D, magnification ×400) and radiation necrosis from the central region of the sample (E, magnification ×400) of a medial NSCLC brain metastasis.

FIGS. 26A-26I show examples of vessel morphology sampled from regions appearing blue in the maps of patients with primary brain tumors are shown in images A-F. Vessels from regions appearing red in the maps are shown in G-I.

FIGS. 27A-27I show comparison with rCBV. Contrast-enhanced T1-weighted MRI (A, D, G), enhancement subtraction maps (B, E, H) and rCBV maps (C, F, I) are shown. As shown there is agreement between the blue rim surrounding the surgery site in B and the high rCBV values in C. There is disagreement between the large blue volume in our maps (E) and the low rCBV in F.

FIGS. 28A-28D show Kaplan-Meier curves of time to progression in patients above and below the median of four predictors: Initial fast volume (A), initial enhanced volume (B), initial fast growth rate (C) and initial enhanced growth rate (D). These results suggest that the initial fast (blue) growth rate may serve as a prediction of time-to-progression.

FIGS. 29A-29F show examples of progression and pseudoprogression in GBM patients post chemoradiation. Shown are late enhancement subtraction maps with significant increase in the enhancing lesion due to increase in the red volume (A-C), representing pseudoprogression, and with significant increase in the blue component (D-F) with minor changes in the enhancing volume, representing progression.

FIGS. 30A-30F show an example of progression under Bevacizumab. Shown are contrast-enhanced T1-weighted MRI (FIGS. 30A, 30C and 30E) and respective subtraction maps (FIGS. 30B, 30D, 30F) of a patient prior to (FIGS. 30A and 30B) and 1 month (FIGS. 30C and 30D) and 3 months (FIGS. 30E and 30F) after initiation of treatment. A significant decrease of the red component and increase of the blue component with time can be seen.

FIGS. 31A-31F show an example of response to Bevacizumab and re-irradiation. Shown are contrast-enhanced T1-weighted MRI (FIGS. 31A, 31C and 31E) and respective subtraction maps (FIGS. 31B, 31D and 31F) of a patient prior to (FIGS. 31A and 31B) and 3 month (FIGS. 31C and 31D) and 5 months after initiation of treatment. 3 months after initiation of treatment the conventional MRI shows radiological improvement while our maps show significant increase in the blue volume, in accordance with clinical deterioration. Due to progression, the patient was treated with re-irradiation immediately after the 3 months. The 5 months follow-up shows a significant response (red in the maps).

FIGS. 32A-32H show another example of progression under Bevacizumab. Shown are T1-weighted MR images with Gd agent (FIGS. 32E-H) and respective subtraction maps (FIGS. 32A-D), of a patient prior to (FIGS. 32A and 32E), and 1 week (FIGS. 32B and 32F), 1 month (FIGS. 32C and 32G) and 3 months (FIGS. 32D and 32H) after initiation of treatment, showing continuous increase in the blue component accompanied by clinical deterioration.

Figure 33B:
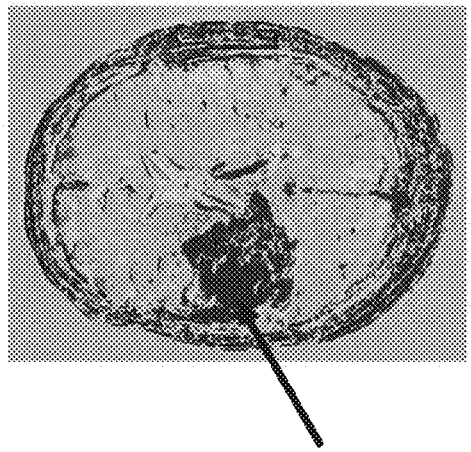
Figure 33A:
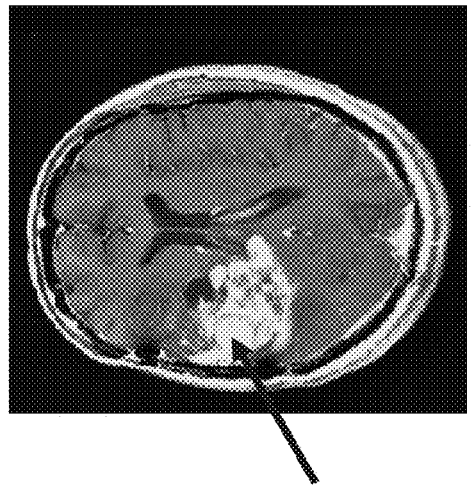
Figure 33C:
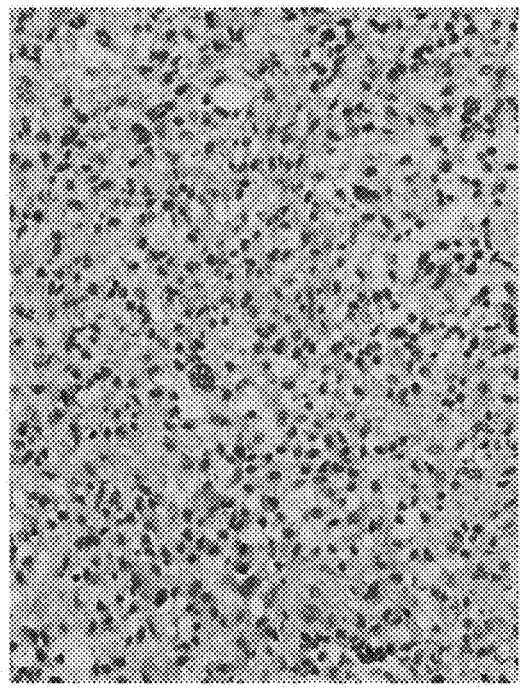
Figure 33E:
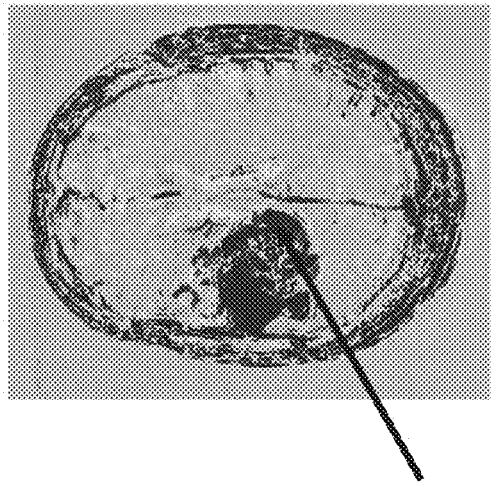
Figure 33G:
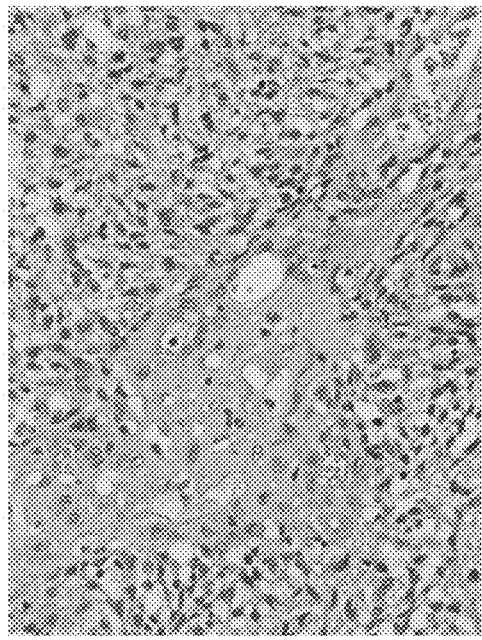
Figure 33D:
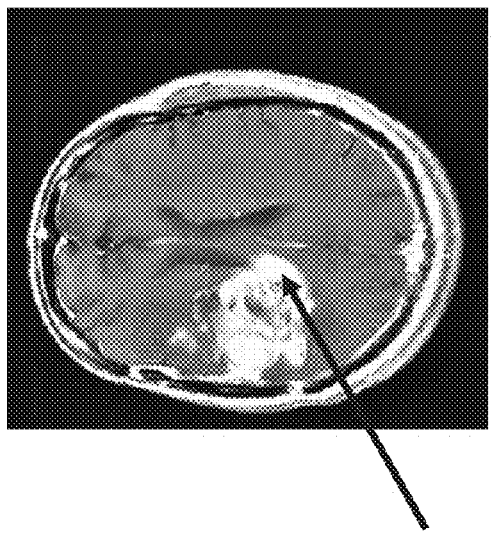
Figure 33F:

FIGS. 33A-33G show MR images (FIGS. 33A and 33D), respective subtraction maps (FIGS. 33B and 33E) and histology (FIGS. 33C, 33F and 33G) of a Bevacizumab-treated tumor. FIG. 33C is histology sample of the blue volume in FIG. 33B, FIG. 33F and FIG. 33G are histology sample of the blue volume in FIG. 33E.

DESCRIPTION OF THE PREFERRED EMBODIMENTS

The present invention relates to method and apparatus for producing magnetic resonance (MR)-based maps and, more particularly, but not exclusively to using such maps to identify and study tumors, particularly but not necessarily brain tumors.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It was found by the Inventors of the present invention that by acquiring MRI data up to twenty or more minutes, or up to 75 min post contrast administration, or even up to 90 minutes or more, can add unique information regarding the late contrast clearance component. Calculated maps of these unique enhancement and clearance characteristics were found to provide a clear distinction between tumor and non-tumoral tissues with high resolution and high sensitivity to subtle blood brain barrier disruption.

The current standard of care for newly diagnosed glioblastoma multiforme (GBM) is resection, when possible, followed by radiotherapy with concomitant and adjuvant temozolomide. Pseudoprogression is a radiographic term referring to early increase in enhancement seen post treatment with improvement/stability after a couple of months. Conventional MRI is currently unable to differentiate between tumor progression and pseudoprogression. Since the treatment depends greatly on this question, reliable distinction between the two conditions is crucial.

The methodology is based on delayed contrast extravasation MRI for calculating subtraction maps depicting unique characteristics with high resolution and high sensitivity to subtle blood brain barrier disruption. These maps provide clear depiction of tumor and non-tumoral components of enhancing GBM lesions.

In some embodiments of the present invention the subtraction maps are blood vessel function maps.

Twelve GBM patients undergoing standard chemoradiation were recruited and scanned by MRI three weeks after chemoradiation and every two months thereafter. Subtraction maps were calculated from high resolution MR images acquired up to 75 min after contrast administration. Two primary populations were determined: A slow population, in which contrast accumulation in the tissue was slower than contrast clearance, and a fast population in which clearance was faster than accumulation. Stereotactic biopsy samples confirmed the fast population to consist of morphological active tumor and the slow population to consist of non-tumoral tissues.

The volumes/intensities of the fast population were doubled when increasing the delay from 15 to 75 min suggesting increased sensitivity to tumor tissues at longer delays.

Significant correlation found between the maps and conventional contrast-enhanced MRI suggest that on average 40% of the enhancing lesion on conventional MRI does not represent morphological active tumor. The application for prediction of response to therapy was demonstrated by significant correlations between initial vessel function values and later tumor volumes on conventional MRI. Only one patient within this cohort showed no blue component in any of his images. This patient is currently progression free for one year after chemoradiation.

Subtraction maps based on the above-mentioned delays enable high resolution differentiation between tumor and non tumoral tissues. The information provided allows for appropriate patient management, both in deciding whether to operate on a patient with radiologic deterioration, continue chemoradiation or change to a second line non-surgical treatment. The present maps may also be applied for planning resection in the most efficient and safe manner and for early prediction of response to therapy, thus enabling selection of patients susceptible to benefit from the treatment.

The principles and operation of an apparatus and method according to the present invention may be better understood with reference to the drawings and accompanying description.

Figure 1A:
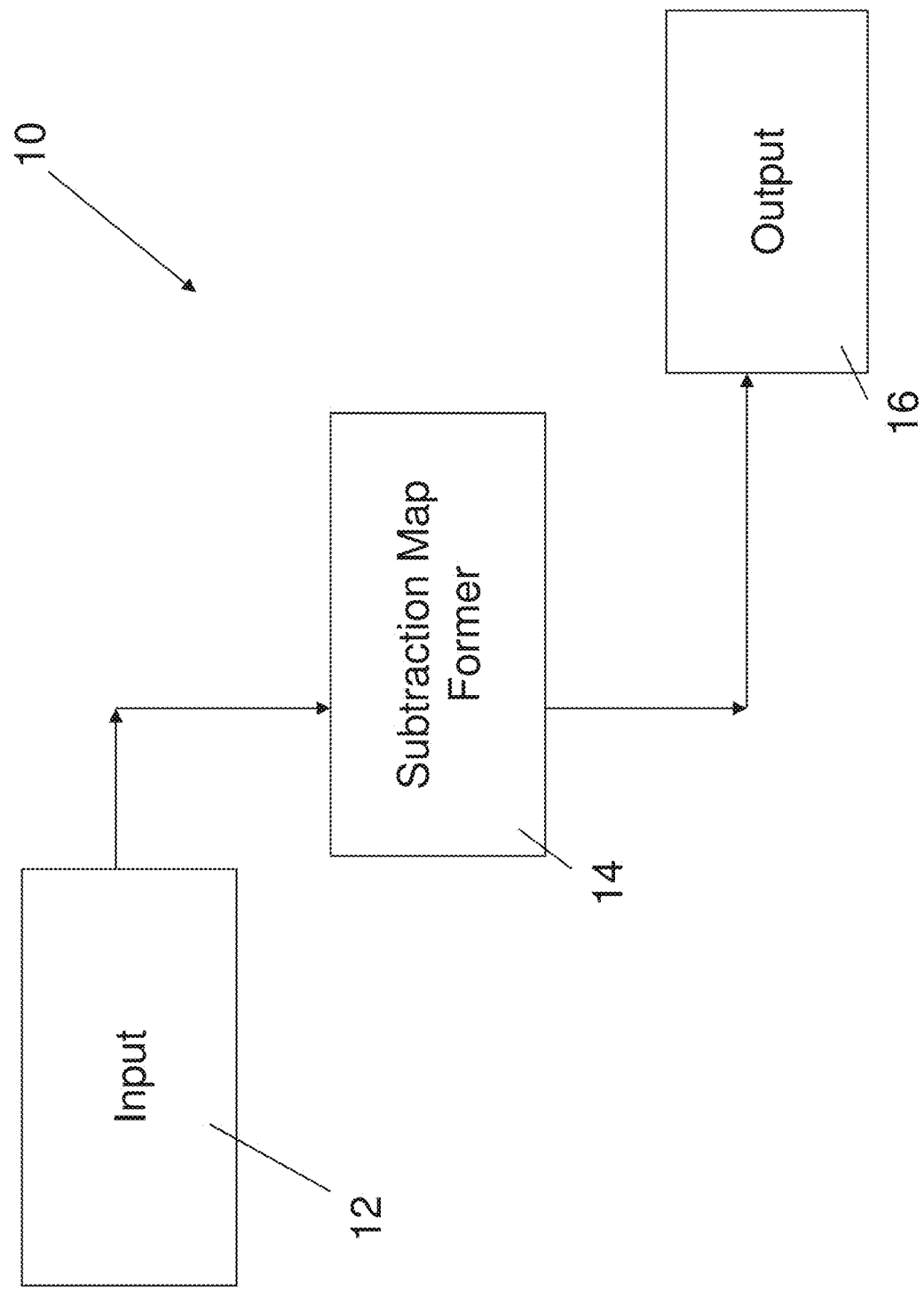

Reference is now made to FIG. 1A which illustrates apparatus 10 for analyzing brain tissue, comprising an input 12 for receiving a first and a second MRI series at the beginning and end of a predetermined time interval, and a subtraction map former 14. The subtraction map former forms a subtraction map from the two MRI series by analyzing the series to distinguish between two primary populations, a slow population, in which contrast clearance from the tissue is slower than contrast accumulation, and a fast population in which clearance is faster than accumulation. An output 16 provides an indication of distribution of the two primary populations. In the present embodiments, the time period between the two series is at least twenty minutes. The time period may additionally exceed thirty minutes, or even forty minutes, or fifty minutes, or sixty minutes, or seventy minutes, or eighty minutes, or ninety minutes, or a hundred minutes. Specifically, time periods used may be seventy minutes, or seventy five minutes or ninety minutes.

Figure 1B:
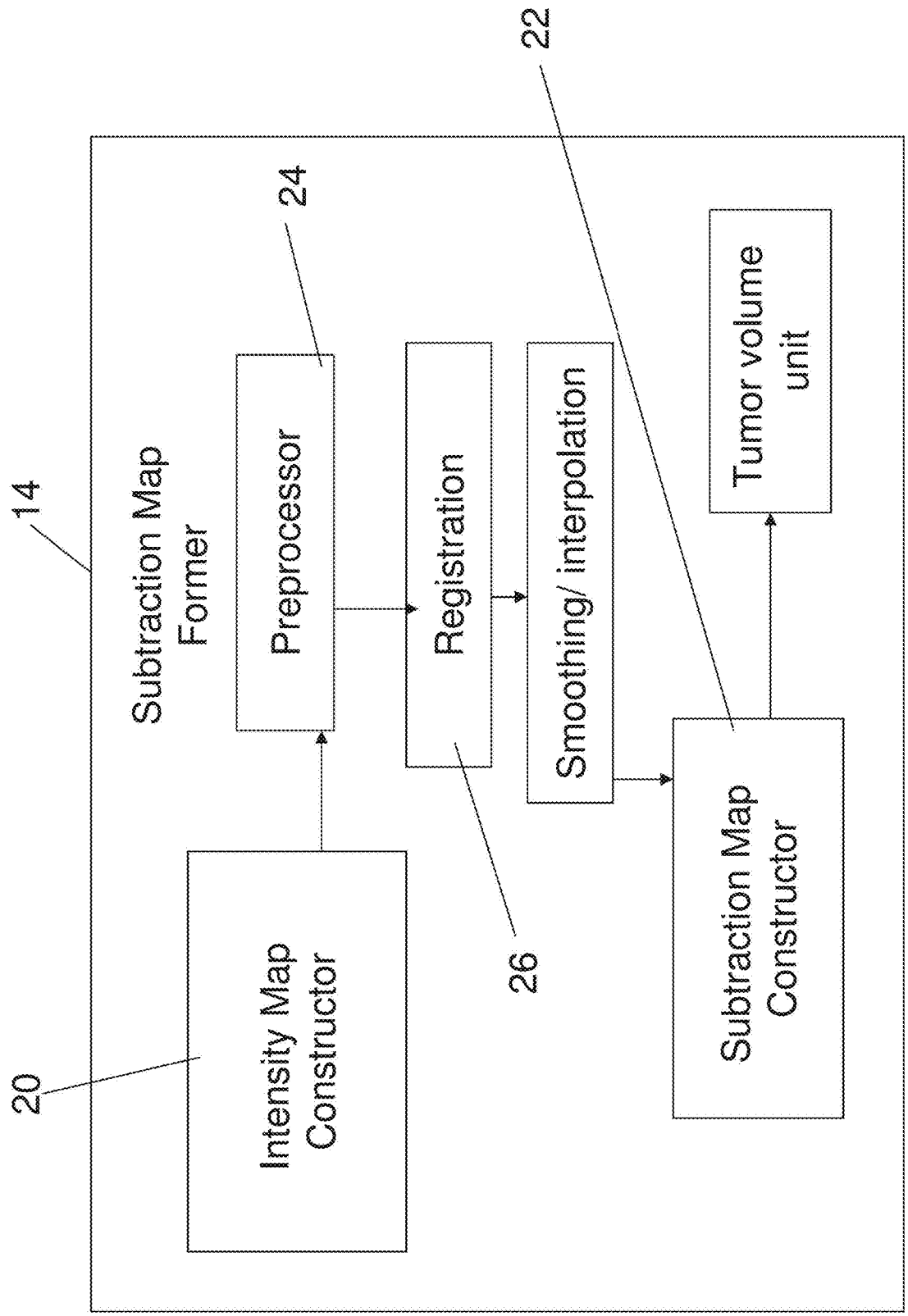

Reference is now made to FIG. 1B which shows the subtraction map former of FIG. 1A in greater detail. The subtraction map former includes an intensity map constructor 20 for constructing, for each magnetic resonance image, an intensity map. A subtraction map constructor 22 constructs a subtraction map describing variations in concentration of the contrast agent in said brain by detecting dissimilarities among a pair of intensity maps.

The subtraction map former 14 may assign a representative intensity value for each magnetic resonance image and determining a time-dependence of the representative intensity value.

The subtraction map former may generate a graph describing the time-dependence.

The input 12 may typically use high resolution spin-echo T1-weighted MR images (T1-MRIs).

The subtraction map former may use the subtraction map to assess whether tumor tissue is present or whether what appears to be tumor tissue is mere treatment effect, by comparing drainage of the contrast agent from blood vessels with contrast agent take up in the tissue.

The image may be pre-processed at preprocessor 24, prior to subtraction. The preprocessing may involve:
a) correction for intensity variations; and
b) whole body image registration.

Correction for intensity variations may comprise calculating, for each MRI image separately, an intensity variation map consisting of large scale intensity variations therein and then subtracting the intensity variation map from the respective image.

A registration unit 26 carries out registration between corresponding MRI images. Registration unit 26, can be, for example, a dedicated circuitry. Registration may comprise a local registration or alternatively an elastic registration, to allow for head movements between the two series.

Elastic registration comprises dividing each slice of a respective series into to a grid of volumes, and allowing each volume to move freely in three dimensions until a sum of the absolute values of the intensity difference between the two time points reaches a minimum. A three-dimensional translation matrix is generated to match between the two images.

Figure 1C:
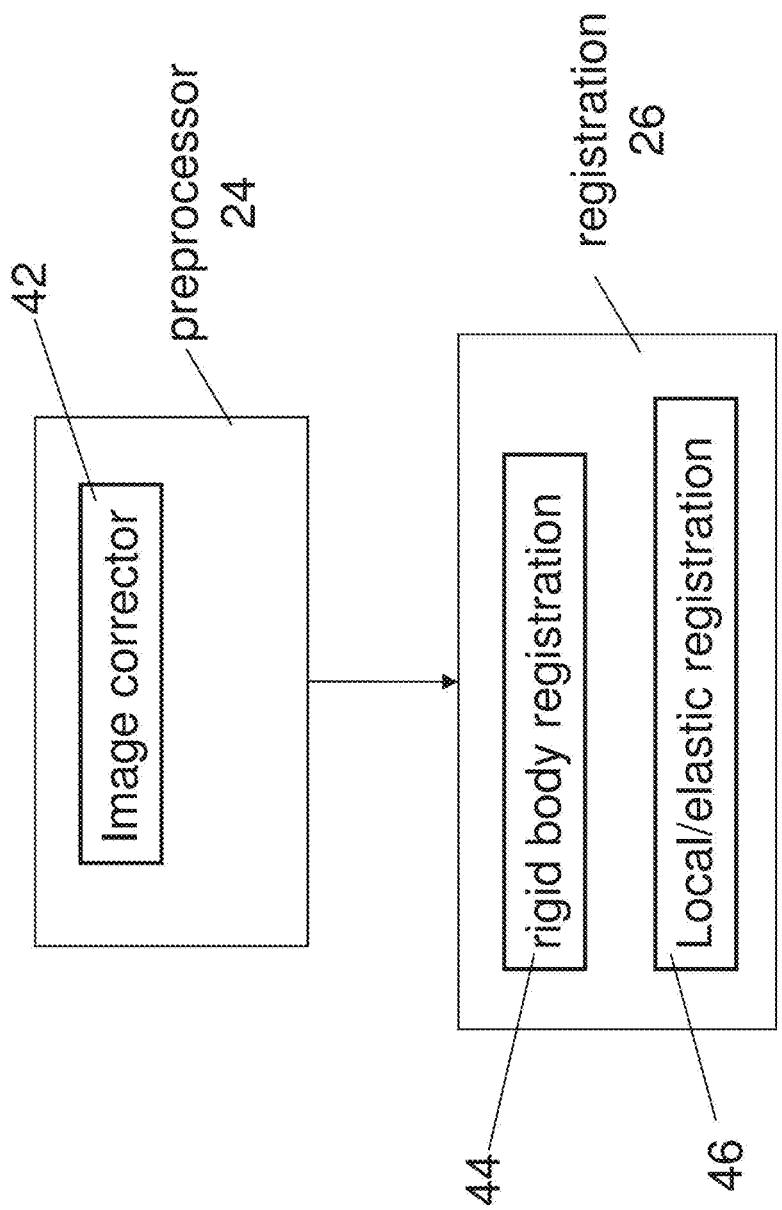

FIG. 1C is a simplified block diagram showing the preprocessor 24 and registration unit 26 in greater detail. Preprocessor 24 optionally and preferably comprises an image corrector 42 which performs intensity correction on each image of the MR images. This can be done by calculating an intensity variation map consisting of the large scale intensity variations. In various exemplary embodiments of the invention the map is then subtracted from the original image resulting in a flattened image. The flattened image is transmitted from image corrector 42 to registration unit 26. Registration unit optionally and preferably comprises a rigid body registration unit or circuitry 44 and a local or elastic registration unit or circuitry 46.

Rigid body registration unit or circuitry 44 is preferably configured to apply a rigid body registration to the second MRI series in order to register it to the first MRI series. The rigid body registration can include, for example, a 6 parameter (rigid body) spatial transformation. Local or elastic registration unit or circuitry 46 is preferably configured to apply elastic registration in order to register the second MRI series to the first MRI series to correct for distortions induced in the MRIs by the head movements.

A smoothing and interpolation unit 28 may be located after the registration unit. Smoothing and interpolation unit 28 can be, for example, a dedicated circuitry. The three-dimensional translation matrix resulting from the elastic registration may be smoothed using circular smearing, and then interpolated to obtain translation values per pixel.

In use, an initial tumor portion may be determined from the first series, which would typically be made two minutes after contrast injection. A threshold is determined from intensity distribution histograms of the tumor and surrounding regions and is applied to define ROIs that include only enhancing portions of the tumor. Regions of interest (ROIs) are thus defined over an entire enhancing region in each slice.

A tumour volume unit 30 may count a number of pixels in the enhancing portions of the ROIs and to multiply by a volume represented by a single pixel to provide a resulting volume as a parameter for assessment of tumor response. Tumour volume unit 30 can be, for example, a dedicated circuitry.

Figure 1D:
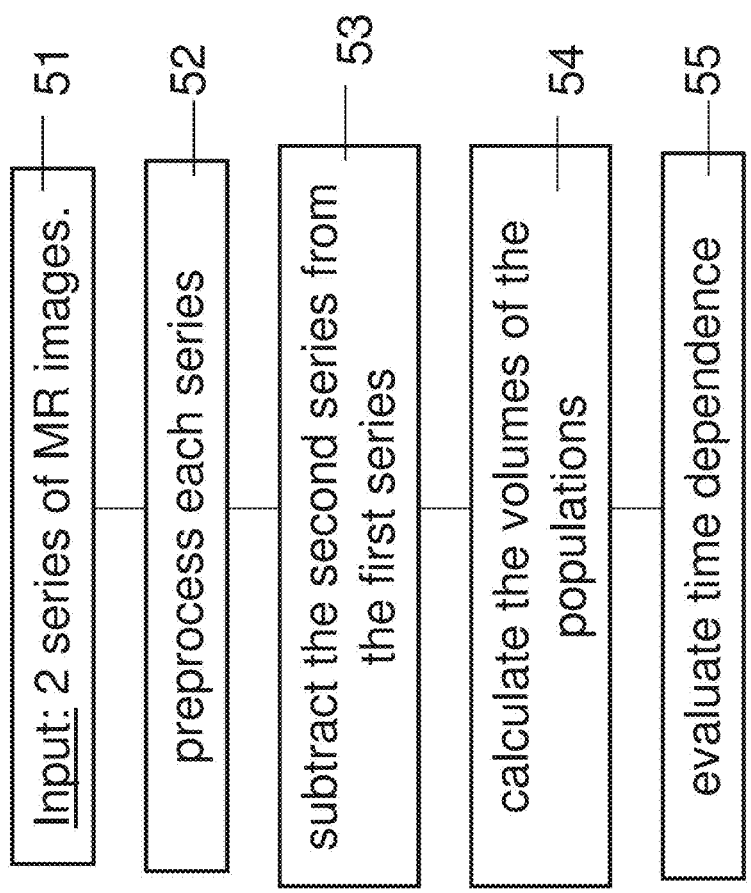
Figure 1E:
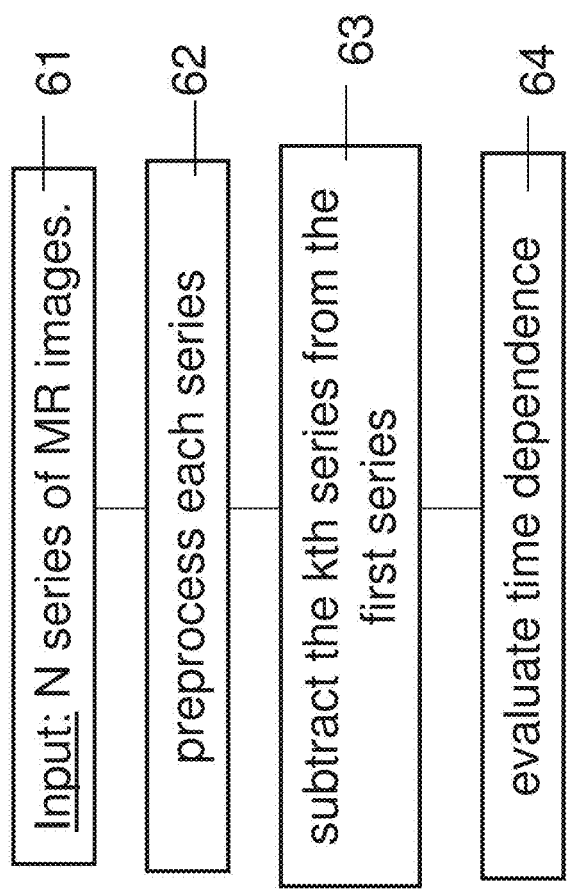

FIGS. 1D and 1E FIGS. 1D and 1E are flowchart diagram describing a procedure for constructing subtraction maps, according to some embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Referring to FIG. 1D, at 51, 2 series of MR images are obtained. A first series can be acquired soon after contrast administration and a second series can be acquired after a predetermined time period as further detailed hereinabove.

At 52, the two series are preprocessed, for example, by applying an intensity correction as further detailed hereinabove with respect to image corrector 42. At 53, the pre-processed second series is subtracted from the pre-processed first series. At 54, the volumes of the various populations (such as, but not limited to, the slow and fast populations) that appear in the maps are calculated.

Optionally and preferably the subtraction maps are used during a longitudinal follow-up of a patient. In these embodiments a time dependence is evaluated (55) throughout the follow-up of the patient. For example, parameter calculated from the maps at different follow-up time points of a patient can be used for predicting and/or monitoring the response of the patient for treatment. For example, the change in blue volume between the first 2 follow-up time points of a patient can be used for prediction of time-to-progression.

In some embodiments of the present invention more than 2 series of MR images are obtained. A representative example of these embodiments is illustrated in FIG. 1E. Thus, at 61 N series of MR images are obtained. The first series is preferably acquired soon after contrast administration, as further detailed hereinabove. The additional N−1 are preferably acquired at various time points thereafter. At 62 each series is preprocessed as further detailed hereinabove. At 63, the pre-processed kth series (k>1) is subtracted from the pre-processed first series. At 64, a time dependence can be evaluated. For example, the signal of each pixel (or some ROI) in the maps can be calculated as a function of time post administration. A mathematical fitting procedure can be applied so as to fit the time dependence to a mathematical model. The fit can then be used for extracting information from the temporal behavior signal. For example, the fit can be used to extract permeability of the blood vessel, tissue density, and the like.

An application of the present embodiments involves depiction of brain tumors after treatment with anti-angiogenic treatments and studying the mechanism of action and response patterns of anti-angiogenic drugs.

A further application involves depiction of brain disorders after treatment with radiation-based treatments, for differentiation between tumor progression and radiation necrosis.

A further application of delayed extravasation MRI allows for differentiation between progression of brain space occupying lesion (SOL) and treatment effects following radiosurgical treatment.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Patients and Treatment:

Twelve patients with histologically confirmed glioblastoma (World Health Organization [WHO] grade IV astrocytoma) were recruited. Eleven with newly diagnosed GBM and one patient with secondary GBM, two years after resection of an Anaplastic Astrocytoma (WHO grade III tumor). All patients received the standard radiotherapy of 60 Gy in thirty daily fractions, five days a week, with concomitant daily temozolomide of 75 mg/m$^2$ for forty two days. Chemoradiation was followed by six cycles of adjuvant temozolomide of 150-200 mg/m$^2$ daily for five days every twenty eight days. Three patients were recruited prior to surgery and nine after completion of the chemoradiation treatment. The mean age was 50.7±3.7 with a range of 27-71. Nine of the twelve patients were men.

Inclusion criteria included patients with WHO performance status of 2 or less and adequate hematologic, renal, and hepatic function. Exclusion criteria included contraindications to MRI and stable condition to undergo an MRI exam. Ten patients underwent gross tumor resection and two patients underwent stereotactic biopsy. Three patients were recruited and scanned prior to treatment. The patient with secondary GBM was recruited and scanned prior to resection. Three additional patients underwent a second resection six-eight months after treatment initiation. One of them died ten days post-surgery and the other two, following clinical deterioration, were treated with Bevacizumab.

MRI Schedule:

Patients were scanned by conventional and delayed extravasation MRI 3-4 weeks after chemoradiation and every 2 months thereafter. Patients recruited prior to surgery or prior to chemoradiation underwent an additional MRI exam. Patients with clinical deterioration underwent additional MRI exams at the discretion of the physician.

MRI Data Acquisition:

MR images were acquired using a clinical General Electric 3.0 T MRI machine (GE Medical Systems, Waukesha, Wis., USA) with the HD12 operating system, gradients intensity of up to 4.3 Gauss/cm and the standard GE phased array head-coil. MR sequences included T2* PWI, Fast spin-echo T2-weighted MRI, T2 FLAIR and echo-planar diffusion-weighted MRI (DWMRI). High resolution spin-echo T1-weighted MR images (T1-MRIs) were acquired before and at three time points after contrast injection: 2.6±0.1 min (immediately after the PWI sequence), 15.4±0.4 min and 75.3±0.7 on average. These times are referred to as the 2 min, 15 min and 75 min time points throughout the text. T1-MRI was acquired with TE/TR=22/240 ms, field of view 26×19.5 cm, 5/0.5 mm slice thickness and 512×512 pixels. A standard dose (0.2 ml/Kg) of Gd-DOTA (Dotarem, 0.5 mmol/mL, Guerbet, 95943 Roissy CdG Cedex, France) was injected intravenously using an automatic injection system six seconds after starting the PWI sequence.

MRI Data Analysis:

The overall goal of the analysis is to obtain subtraction maps, where the T1-MRIs of the 1$^{st}$ series post contrast are subtracted from the T1-MRIs of the later series. These maps depict spatial distribution of contrast accumulation/clearance in the tissue, blood vessels and CSF. In case of intact blood brain barrier, due to clearance of contrast agent from the blood system, there is no increase in contrast accumulation after the first series; therefore, the subtraction maps have negative values, shown as blue in the maps. The signal decay of the blood vessels is faster than that of the tissue, where the signal is averaged over the tissue and microvasculature, therefore, blood vessels have lower values than tissue. In case of blood brain barrier leakiness, regions where contrast clearance is slower than accumulation have positive values, shown as red in the maps.

In order to increase the sensitivity to small changes, image pre-processing was carried out, consisting of correction for intensity variations and whole body image registration.

Correcting for Intensity Variations:

Signal intensity homogeneity throughout the image and between slices depends on various parameters including the strength and homogeneity of the static magnetic field, the oscillating excitation field, the gradients, the sensitivity of the receiving coil and various parameters of the sampled tissue. An intensity correction was performed on each image separately by calculating an intensity variation map consisting of the large scale intensity variations and then subtracting it from the original image.

Rigid Body and Elastic/Local Registration:

Rigid body registration was performed using least squares approach and six parameter (rigid body) spatial transformation with the SPM5 (Statistical parametric mapping) MatLab routine (an academic software kit by "Wellcome Trust Centre for Neuroimaging"). Since head movements caused changes in the magnetic field inducing distortions in the MRIs, it was necessary to add local/elastic registration performed by dividing each slice to a grid of 20×20 mm volumes. Each square volume was allowed to move freely in x-y-z till the sum of the absolute values of the intensity difference between the two time points reached a minimum. The resulting three 3D translation matrices were smoothed using circular smearing and interpolated to obtain translation values per pixel. These high resolution matrices were then applied to register T1-MRIs of the second time point to the location of the first time point.

Subtraction Maps:

Following the pre-processing, subtraction maps are calculated by simply subtracting the processed images of the series acquired 2 min after the contrast injection from a series acquired later on, at least 20 minutes after contrast injection, and more preferably, after 70 minutes or 75 minutes or 90 minutes.

Enhancing Tumor Portion:

The enhancing tumor portion is calculated from the spin-echo contrast-enhanced T1-MRIs acquired 2 min after contrast injection. Regions of interest (ROIs) are defined over the entire enhancing region in each slice. A threshold, determined from intensity distribution histograms of the tumor and surrounding regions, may be applied to the ROIs to include only enhancing portions of the tumor. The number of pixels in the enhancing portions of the ROIs are counted and multiplied by the volume represented by a single pixel. The resulting volume is then used as the parameter for assessment of tumor response, in place of equivalent resulting volumes obtained by other methods known in the art.

All image analysis was performed using MatLab (version R2006b, The MathWorks, Inc. Natick, Mass., US).

Histology:

Histological analysis was performed with tissue samples obtained from four patients. Ten stereotactic biopsy locations, obtained from three patients (#1, #4 and #12), were determined prior to surgery using the calculated subtraction maps which were co-registered to the conventional T1-MRI. Eight additional samples were obtained from patient #3, chosen by the neurosurgeon during surgery as representative samples. All samples were marked by the neurosurgeon during resection and then fixed and stained by H&E according the routine hospital procedure. Histological interpretation was performed by the hospital neuro-pathologist.

Results

Blood Vessels Function Maps:

Vessel function maps were calculated using the data acquired 15 min (15 min maps) and 75 min (75 min maps) after contrast injection. Two primary vessel function populations were determined: the slow population (red in the calculated maps), in which contrast clearance from the tissue was slower than contrast accumulation, and the fast population (blue) in which clearance was faster than accumulation. Normal brain regions, due to the intensity variation correction, had an average value of zero, depicted in green in the maps. Examples of 15 and 75 min maps are shown in FIG. 2A. It can be seen that abnormal vessel function in the 75 min map is depicted more clearly and in larger regions than in the 15 min map. Examples of the signals intensities of the fast and slow populations as a function of time after contrast injection are shown in FIG. 2B, demonstrating the different rates of contrast accumulation and clearance of these vessel populations.

Histological Determination:

Ten stereotactic biopsy samples acquired from three GBM patients suspected to suffer of disease progression and undergoing surgery were compared with the pre-surgery calculated maps, which were co-registered with the conventional T1-MRI. The biopsies confirmed the discrimination between blue regions, determined by histology to consist of morphological active tumor: hyper cellularity, small cells, mitosis, high Ki67, pseudo-palicading necrosis, vascular proliferation; and red regions, determined to consist of non-tumoral tissues: radiation changes including large, widely spaced atypical astrocytes, blood vessels hyalinization, fibrinoid material in vessels, proliferating small vessels, tumor necrosis. A list of these stereotactic biopsies can be found in Table 1. Examples of 3 samples obtained from patient #1 are shown in FIG. 3.

Patient #3 underwent a second resection six months after chemoradiation due to clinical deterioration. The patient died 10 days post-surgery. The maps calculated from his last MRI series, showed that the blue component reached 71±3% of the enhancing portion of the tumor. Histological analysis was performed for eight samples taken from two main regions of the lesion. The temporal region samples showed tumor with a circular nodular shape apparent mainly in the central slices. The tumor was cellular with many mitoses and regions of "geographic necrosis". Some regions of the tumor showed proliferative blood vessels. Some regions surrounding the tumor depicted brain tissue infiltrated by a small number of tumor cells and abnormal proliferation of blood vessels and multiple histiocytes. The tumor load in this region was estimated to cover ~70% of the examined samples, in agreement with our calculated maps. The frontal region samples showed a mixture of tumor, fibrosis, necrosis and brain tissue with proliferating blood vessels. In one region, adjacent to connective tissue, it was possible to see a malignant tumor osteoid. Also depicted were small edema foci with small reparative foci. The tumor load in this region was also estimated to cover ~70% of the examined samples in agreement with our calculated maps.

Long Delay Versus Moderate Delay:

The volume and intensity of the blue population, calculated from the 15 min maps were found to correlate significantly with those calculated from the 75 min maps: $r^2=0.96$, $p<0.0001$ and $r^2=0.79$, $p<0.0001$, respectively. The correlation functions showed that the volumes and intensities of the blue population increased by a factor of 2.0±0.1 and 2.1±0.2 respectively when using the 75 min delay, suggesting increased sensitivity to tumor tissues at the longer delays.

Correlation with Other Calculated MR Parameters:

The volume of the blue population was found to correlate significantly with the enhancing portion of the tumor: $r^2=0.90$, $p<0.0001$. The correlation function showed that the enhancing portion of the tumor was 1.6±0.1 times larger than the volume occupied by the blue population, suggesting that on average 40% of the enhancing lesion on conventional MRI does not represent morphologically active tumor. An example is shown in FIG. 4. In this lesion the volume occupied by the blue component was 22.0±2.2% in the 15 min map and 32.2%±3.2 in the 75 min map.

Significant correlation was also determined between the intensity of the blue population and rCBV calculated from perfusion-weighted MRI (PWI, $r^2=0.54$, $p<0.0008$), suggesting that rCBV is a dominant characteristic of the blue population.

The feasibility of applying the calculated maps for prediction of response to therapy was studied by correlating parameters calculated from the first MRI, acquired 3 weeks after chemoradiation, with parameters calculated from MRIs acquired at 4 and 6 months post therapy. A subgroup of 7 patients who reached the 4 months follow-up MRI, showed significant correlation between initial values of the blue volume and later enhancing portion of the tumor: $r^2=0.84$, $p<0.004$. The correlation between initial values of the product blue volume×blue intensity with later enhancing portion of the tumor was significant as well, $r^2=0.93$, $p<0.0005$. The latter correlation suggests that the intensity of the blue component, reflecting the rate of contrast clearance, may also be associated with tumor growth. A similar correlation ($r^2=0.94$, $p<0.001$ for both) was found for a subgroup of 4 patients who reached the $4^{th}$ follow-up MRI, 6 months post treatment.

There was only one patient in this study who demonstrated no blue component in any of his images. This patient is currently progression free for one year after chemoradiation.

Vessel Function Patterns:

Various patterns of the blue component presentation and expansion were observed. For example, in five of the patients, the first MRI acquired three weeks post treatment revealed an intense blue rim surrounding a cystic region (FIG. 5). Two patients had rapid increase in tumor volume 5-7 months after treatment initiation (FIG. 6). Within 2 months the enhancing portions of the tumor increased by 3-4 fold while the volumes of the blue components increased by a factor of 2. In another patient the lesion volume did not change significantly throughout 6 months follow-up despite an increase of almost 80% in the blue component volume, accompanied by clinical deterioration (FIG. 7). In all eleven patients who showed a blue component in the first follow-up, a blue component was always observed throughout all remaining follow-ups. Decrease in the absolute volume of the blue component was observed in four patients up to four months post treatment initiation. No decrease was observed after this time point in any of the patients.

Discussion

Glioblastoma multiforme is the most common and most aggressive type of primary brain tumor in humans. The current standard of care for newly diagnosed GBM is surgical resection (when possible) followed by radiotherapy with concomitant and adjuvant temozolomide chemotherapy. Conventional MR imaging is currently unable to provide reliable distinction between tumor recurrence and pseudoprogression. Clinically, this question has important consequences, and a reliable distinction between the two conditions is, therefore, crucial.

Using high resolution T1-MRI acquired at long delays after contrast administration two main vessel function populations were identified based on their different rates of contrast accumulation and contrast clearance. These results are in agreement with an early study by Hazle et al (1997) who studied the enhancement curves of various brain tumors and found that radiation necrosis and tumor enhance at different rates, enabling significant differentiation between recurrent tumor and radiation necrosis.

Comparison with stereotactic biopsies confirmed that the fast population represents tumor while the slow population represents non-tumoral tissues. As mentioned in the introduction, high rCBV values have been shown to be associated with tumor recurrence while low values have been associated with pseudoprogression. The present results show that the blue component in the vessel function maps is significantly correlated with high rCBV values calculated from PWI, suggesting that rCBV may be a dominant characteristic of this population. Still, the correlation with PWI was lower than with other parameters presented in this work. This effect may be explained by the poor quality of the PW images in this population of post-surgery GBM patients. In most of these patients, the residual/recurrent tumor is located in the vicinity of surgical screws which induce significant image distortion when using the fast echo-planar MRI sequences for acquisition of PWI data. Distortion may also be induced by hemorrhages which are seen frequently in GBM.

On the other hand, the lower correlation with PWI may imply existence of other contributions to the fast component, such as increased vessel permeability. A study designed to fit accumulation and clearance functions to the time curves presented in FIG. 2 in order to determine the dominant factors contributing to the vessel functions populations is ongoing. Determination of additional subpopulations may lead the way to better understanding of tumor progression and tumor response to various treatment regimens. A study designed for better understanding of Bevacizumab (a humanized monoclonal antibody that inhibits vascular endothelial growth factor A) mechanism of action using our vessel function maps is currently ongoing.

In a previous study performed with thirty three ischemic stroke patients it was demonstrated that there was no blue component in any of the twenty one stroke patients who depicted significant volumes of blood brain barrier disruption in our calculated maps. These results are consistent with the determination of the red component as non-tumoral tissue. In the same study we also presented examples of two patients with multiple brain metastases of breast cancer and melanoma, demonstrating significant regions of the fast component. Another study designed to apply our maps for differentiating tumor progression from radiation necrosis in patients with brain metastases undergoing radiosurgery is ongoing.

A significant advantage of using the delayed enhancement and clearance rates instead of the commonly used early enhancement rates is the ability to apply sequences with lower temporal resolution, such as high resolution spin-echo T1-MRI sequences. These sequences nearly completely avoid susceptibility artifacts while providing high signal-to-noise ratios, high resolution and high sensitivity to contrast variations.

The search for clinically useful biomarkers for prediction of treatment response in malignant gliomas is an emerging field. Still, the current endpoint in most clinical studies is tumor size. Tumor size is traditionally estimated from cross-sectional area, which is calculated as the product of the longest diameter and its longest perpendicular diameter. It is typically computed by assuming the overall lesion can be described by an ellipsoid. However, as GBM lesions tend to be irregular in shape and often include cystic areas, it would stress the assumptions of the routine cross-sectional approach and be associated with the risk of error. The volumetric methods are thought to allow for better quantification of tumor volume because of the addition of the third dimension and no need to assume a shape. Therefore, in our study the standard tumor size was calculated as the enhancing portion of the tumor using a standard volumetric method and referred to as the state of the art mean for response assessment.

Since the patients in our study are excluded once clinical deterioration requires a change in the treatment regimen (resection or treatment with Bevacizumab in most cases), it was not possible to correlate our findings with overall survival. Therefore, feasibility of applying our maps for prediction of response to therapy was demonstrated by studying the correlation of our calculated parameters with later enhancing portions of the tumors. The significant correlation found between initial volumes of the blue component and later enhancing portions of the tumors suggests the initial volume of the blue component as a biomarker for response. Improved correlation was obtained using the product value of the blue volume and blue intensity, implying that the intensity of the blue component may also play a role in tumor aggressiveness. The above mentioned study, designed to fit accumulation and clearance functions to the time curves, may provide a better understanding of the physiological meaning of these parameters.

The distinction between tumor and non-tumoral tissue is of high value in differentiating tumor progression from pseudoprogression. As we demonstrate above, the volume of tumor tissue early after treatment may be used for prediction of later changes in the enhancing portion of the tumor. The ability to depict tumor regions with high resolution may also be used for better planning of therapeutic procedures including sampled biopsies, gross total resections, implantation of various systems for local therapies, local non-invasive therapies such as radiosurgery, focused ultrasound treatments and more.

During the performance of the study we notice various patterns of tumor presentation as demonstrated in the Results section. These observations suggest that the ability to depict the tumor component of enhancing lesions may lead the way to additional important applications such as quantification of residual tumor post-surgery and determination of progression and response patterns following treatment.

In summary, the high resolution vessel function maps of the present embodiments enable clear differentiation between tumor and non tumoral tissues. This information may provide appropriate patient management, whether in deciding to operate on a patient with radiologic deterioration, continue chemoradiation or change to a second line non-surgical treatment. In the case of surgery—the maps of the present embodiments may provide additional information for planning resection in the most efficient and safe manner. In addition, the function maps may be used for early prediction of later tumor volume, thus enabling selection of patients who are more likely to benefit from the treatment.

TABLE 1

List of stereotactic biopsies and their vessel function map characteristics

| Sample # | Patient # | vessel function population | Histological description |
|---|---|---|---|
| 1 | 1 | Mixed regions of blue, red and green populations | One cellular region consisted of small cells with no mitoses. Proliferation was seen in 5% of the cells by Ki67 staining, implying active tumor. Other regions showed post radiation changes. One region was of brain parenchyma with no obvious abnormalities |
| 2 | 1 | Cortical region of blue population and deeper white matter region of red population | Subcortical infiltrating zone of active tumor with rare mitosis and a deeper, white matter region of post radiation changes. Ki67 staining of the active tumor zone showed proliferation in 3-5% of the cells |
| 3 | 1 | Region of blue population | Active tumor consisting of a hypercellular area of small cells. Ki67 staining showed proliferation in 10-12% of the cells |
| 4 | 1 | Mixed regions of blue and red populations | Regions of active tumor consisting of a hypercellular area of small cells and regions of post radiation changes. Ki67 staining in the active tumor region showed proliferation in 10-12% of the cells |
| 1 | 12 | Region of blue population | Highly cellular tumor with small regions of tumor necrosis with and without pseudo palicading regions of proliferating blood cells. |
| 2 | 12 | Region of blue population | Highly cellular tumor |
| 3 | 12 | Region of blue population | Highly cellular tumor with small regions of necrosis with and without pseudo palicading regions of proliferating blood cells |
| 4 | 12 | Region of blue population | Highly cellular tumor with large proliferating vessels and small regions of tumor necrosis with palicading regions of proliferating blood cells |
| 1 | 4 | Region of red population | Radiation necrosis |
| 1 | 4 | Cortical region of blue population and white matter region of red population | Cortical region shows active tumor accumulating focally beneath the meninges. Focal proliferation of blood vassals and palicading necrosis are identified as well. Most of the deeper white matter region shows radiation necrosis |

Example 2

An application of the present embodiments comprises high resolution depiction of brain tumors after treatment with anti-angiogenic treatments and studying the mechanism of action and response patterns of such drugs.

Standard Treatment:

Glioblastoma multiforme (GBM) is the most common and most aggressive type of high grade glioma and is associated with a median survival of less than 15 months. In 2005, a randomized phase 3 trial demonstrated that the addition of temozolomide (TMZ) to adjuvant radiation therapy was associated with an improvement in the median survival of patients with newly diagnosed GBM from 12.1 months to 14.6 months [1]. This treatment regimen is currently the standard of therapy for newly diagnosed GBM, and is commonly referred to as the "Stupp protocol".

Anti-Angiogenic Treatments:

Nearly all GBM recur after initial therapy, and most patients do not survive beyond 1 year after the diagnosis of recurrent disease. Because re-operation and re-radiation are treatment options for only a subset of patients, the majority of patients are offered chemotherapy at the time of recurrence. Data from clinical trials have established an anti-angiogenic therapy-bevacizumab, a humanized monoclonal antibody that inhibits vascular endothelial growth factor A (VEGF-A), with or without cytotoxic chemotherapy as an active treatment option for patients with recurrent GBM who have failed previous TMZ therapy.

Glioblastoma is one of the most vascularized cancers and many preclinical studies use GBM as a tumor model of angiogenesis. VEGF is an important regulator of angiogenesis that is highly expressed within brain tumors. The degree of both vasculature density and VEGF expression is correlated with the malignancy and aggressiveness of these tumors as well as with outcomes, such as clinical recurrence and survival.

Bevacizumab:

Bevacizumab (Bevacizumab, Genentech Inc) is the best characterized antiangiogenic therapy and recently received FDA approval as a single agent for treatment of recurrent GBM. It has also been recently approved for coverage by the national health insurance in Israel for GBM patients who failed first line therapy. Two large phase III Bevacizumab studies are currently ongoing. The treatment is commonly combined with chemotherapy and results in dramatic radiological changes, prolongation of progression-free survival, and less need for corticosteroids. Still, an overall survival benefit has not been proven and only a small percentage of patients show long term benefit.

Adverse Effects:

Bevacizumab is generally well tolerated but common adverse effects include hypertension and proteinuria, whereas more serious adverse effects, such as thromboembolic disease and hemorrhage, occur infrequently.

Treatment Failure:

At least half of patients fail to respond and the response duration is variable. The molecular basis of bevacizumab failure is poorly understood. A major concern is the hypothesis that these treatments transform a proangiogenic into a promigratory phenotype, resulting in more diffusely infiltrating tumors and finally more neurologic morbidity after an initial phase of symptom relief. Multiple mechanisms are likely involved in treatment failure, including activation of other pro-angiogenesis pathways, mobilization of circulating endothelial cells towards the tumor, increase in tumor invasiveness independent of angiogenesis resulting in increased infiltrative tumor growth along the blood vessels, and increase in the recruitment of vascular progenitor cells from the bone marrow. Recently published clinical studies have thus far provided circumstantial evidence for the hypothesis that bevacizumab does increase tumor hypoxia in patients with glioma. Although oxygen deprivation may have negative short-term effects on cell growth, evasive/adaptive responses to hypoxia can enhance migration and induce resistance toward radiotherapy, chemotherapy, and targeted therapy.

Mechanisms of Action:

Several mechanisms of action have been suggested for the antiglioma effect of antiangiogenic agents, including:
improved vascular function or normalization
direct inhibition of tumor-associated neoangiogenesis
direct antiglial effect on VEGF receptor-expressing tumor cells
disruption of the tumor stem cell microvascular niche The proposed mechanism of action on tumor vasculature is twofold: inhibition of new-vessel formation and killing of immature tumor vessels; and transient normalization of the remaining vasculature by decrease in macromolecular permeability. Vascular normalization results in improvement of blood perfusion and reduction in the accumulation of fluid/edema within the tumor environment. Another effect of bevacizumab may be the direct killing of cancer cells in subsets of tumors in which the cells express VEGF receptors and which depend on VEGF for survival.

Studies have found a significant increase in cell apoptosis after bevacizumab treatment alone. However, the extent to which the increase in apoptosis was due to direct killing of cancer cells by bevacizumab or due to indirect killing by the reduction of blood vessels is still not known.

Convection Enhanced Delivery (CED) of Bevacizumab:

Convection-enhanced drug delivery (CED) is a novel approach to directly deliver drugs into brain tumors. It is based on delivering continuous infusion of drugs via intracranial catheters, enabling convective distribution of high drug concentrations over large volumes of tissue while avoiding systemic toxicity. Application of CED to brain pathology is an emerging field currently in advanced clinical trials.

Bevacizumab is designed to directly bind to VEGF extracellularly to prevent interaction with VEGF receptors on the surface of endothelial and glial cells, thereby inhibiting its biologic activity. When administrated IV, it is safe to assume bevacizumab concentration would be higher around endothelial cells, and penetration of the BLOOD BRAIN BARRIER into the tumor cells (if any) is minimal, therefore most of the effects of bevacizumab documented in GBM patients are most probably due to the effect on the tumor vasculature. Direct administration of bevacizumab by CED of Bevacizumab into tumor extracellular space may result in a high concentration of bevacizumab near the surface of the tumor cells.

An animal study designed to provide further understanding of the direct mechanism of action of Bevacizumab on tumor cells has been performed by the present Inventors. This animal study compares the average survival and tumor growth rate of human glioma bearing rats that are treated with an IV injection of Bevacizumab to those treated with intra-cranial CED of Bevacizumab.

The results of this study may help determine the main mechanism of actions involved in response to Bevacizumab, and may provide first evidence of direct effect of bevacizumab on tumor cells in glioma. If the direct effect of tumor cells (tumor glioma cells and tumor stem cells) are found to be significant, the local administration by CED of Bevacizumab may significantly enhance treatment effects and may decrease the effect of infiltrative tumor growth along the blood vessels as well as reduce treatment related adverse events.

Imaging of Bevacizumab Treatment Effects:

GBMs typically have extensive abnormal vasculature with a blood-brain barrier that is significantly more permeable than normal brain tissue. Because of the increased permeability, contrast material more freely leaks out of tumor capillaries, increasing enhancement on T1-weighted MR images. Traditionally, in the assessment of treatment response, gadolinium-based contrast enhanced MRI has been used to evaluate tumor size. Changes in enhancing tumor size based on bidimensional measurements are the basis for both the RANO (Response Assessment in Neuro-Oncology) criteria, the currently accepted standard criteria for assessing glioma response, and the previously used standard, the Macdonald criteria.

By targeting VEGF, an active permeability agent and promoter of angiogenesis, bevacizumab decreases the leak of contrast agent into the interstitium (vascular normalization), diminishing contrast enhancement. Therefore a unique challenge in using Bevacizumab as well as other angiogenic inhibitors for recurrent GBM, is determining radiographic response. At present, there is no consensus as to the most effective method for determination of response to Bevacizumab treatment.

To address the limitations in the conventional MRI assessment of gliomas, the RANO group has developed new guidelines for treatment response in brain tumors. In contrast to the Macdonald criteria, the RANO criteria include fluid-attenuated inversion recovery (FLAIR) or T2 hyperintensity as a surrogate for nonenhancing tumors in the determination of progression. Unfortunately, it does not quantify the amount of FLAIR or T2 change required for progression. Due to difficulties in differentiating nonenhancing tumor from other causes of increased FLAIR or T2 signal (eg, radiation effects, ischemic injury, and infection), the RANO group felt that an objective criterion for nonenhancing tumor progression was not currently feasible. Thus, it is clear that methods separating nonenhancing tumor from gliosis, and true tumor progression from pseudoprogression, could substantially improve the accuracy of response measures.

The search for clinically useful biomarkers for treatment response in malignant gliomas is challenging. Recently, attempts to assess gliomas using imaging have broadened in focus from strictly anatomic measurements to techniques that quantify changes in tumor physiology. Based on preliminary studies, several physiologic imaging techniques such as T2* weighted MRI, perfusion weighted MRI, diffusion weighted MRI and MR spectroscopy may have the ability to detect treatment response or resistance prior to changes in tumor size. Unfortunately, the clinical utility of these physiologic imaging techniques remains unproven and the methods unstandardized.

The use of magnetic resonance perfusion imaging as a biomarker of response to antiangiogenic drugs has generated significant interest. Most commonly, dynamic susceptibility MRI (DSC) and dynamic contrast enhanced MRI (DCE) are been used to generate maps of relative cerebral blood volume (rCBV) and relative cerebral blood flow (rCBF). The MR parameters calculated from these methods have been shown in a number of studies, to have prognostic value for standard chemoradiation treatment and predictive value for response to antiangiogenic therapy.

Diffusion-weighting imaging (DWI) is another MRI sequence under investigation in the assessment of gliomas. DWI is based on the movement of water molecules, and the measurable parameter is the apparent diffusion coefficient (ADC). Lower ADC values reflect lower (more restricted) diffusion. Several physiologic properties of tumors may influence ADC values. Water molecules are generally more restricted in their movement within cells and less restricted in the extracellular space. Because necrosis involves degradation of cellular integrity, it is thought that necrosis increases ADC. In a similar way, edema increases interstitial fluid, thereby increasing ADC. Conversely, increased cellular density lowers ADC by restricting diffusion. Because of these relationships, DWI has been studied as a means of evaluating the effects of therapy on malignant gliomas.

By examining voxel-wise change in ADC, the sensitivity of detecting subtle changes in tumor cell density is dramatically increased. This technique has primarily been applied as a tool to predict response to cytotoxic chemotherapy and radiotherapy within the contrast-enhancing tumor bed; however, recent studies have demonstrated its utility outside regions of contrast enhancement and as a tool for studying the effects of anti-VEGF therapy. Specifically, one group found a significant decrease in ADC immediately following treatment with Bevacizumab. The rate of change of tissue showing abnormally low ADC within regions of T2 signal abnormality was shown to be an early predictor of tumor progression, time to progression, and overall survival.

Because ADC is influenced by cellular density, necrosis, and edema, ADC values can potentially be used as a noninvasive surrogate for VEGF expression and thus susceptibility to Bevacizumab. ADC histogram analysis was evaluated as a predictive biomarker of response to Bevacizumab in patients with recurrent GBM. Tumors with low ADC values prior to initiation of Bevacizumab were more likely to progress by 6 months compared to those with high ADC values. This histogram analysis was 72.5% accurate in predicting 6-month progression-free survival. In the non-Bevacizumab-treated cohort, ADC values were not predictive of median survival.

The present inventors has developed a novel methodology, based on delayed contrast extravasation MRI for depicting high resolution maps of unique vessels characteristics with high resolution and high sensitivity to subtle blood brain barrier disruption. In a recent study performed with GBM patients undergoing standard chemoradiation, the inventors demonstrated the feasibility of applying these maps for differentiating tumoral regions from non tumoral regions and for providing early prediction of response to chemoradiation treatment.

Some embodiments of the present invention depict and quantify treatment effects of Bevacizumab on tumor vasculature function. In both animal and clinical studies, the components by which Bevacizumab is thought to work are separated, and then correlated with the baseline radiological characteristics of the tumor and the outcome of each individual patient (or animal). In the case of animals, the imaging results may also be compared with histological analysis. The results may further improve the understanding of the mechanism of action of Bevacizumab and of different response patterns to Bevacizumab in GBM patients.

Only a fraction of patients with malignant gliomas respond to antiangiogenic therapy, and the concept of response in this setting is not well defined in the absence of a consensus as to how to depict nonenhancing tumors. Despite accumulating clinical experience, several important questions regarding Bevacizumab in GBM treatment still remain unanswered, including the optimal therapeutic partner, dosage, treatment schedule and treatment duration in responding patients. These questions are almost impossible to answer while radiographic response criteria of Bevacizumab remain unknown.

Thus, it is advantageous to identify radiologic biomarkers that can depict nonenhancing tumors, predict treatment response and accurately measure response after the initiation of therapy, thereby improving decision making and ultimately increasing survival.

The results of the present study provides a further understanding of the mechanisms of action of Bevacizumab on GBMs, and their correlation with patient response/resistance, early detection of drug susceptibility or resistance prior to changes in tumor size, allowing for earlier treatment decisions and more individually tailored medicine, and better selection of patients, by identifying patients who will benefit from the treatment versus those who will suffer significant side effects, thus saving patients from the adverse effects of ineffective therapies while allowing them to try alternative therapies sooner, resulting in improved outcomes for GBM patients.

A study according to some embodiments of the present invention allows to increase the understanding regarding the mechanism of action of Bevacizumab, assessing the direct effect of Bevacizumab on tumor cells and increase treatment efficacy on tumor cells by applying convection enhanced delivery of Bevacizumab, to enable reliable depiction of tumor and non tumoral tissue after treatment with Bevacizumab, defining imaging markers for pre-treatment and/or early post treatment prediction of disease response or progression, and identifying subpopulations of patients that would benefit most from Bevacizumab therapy with minimal side effects.

A study according to some embodiments of the present invention differentiates between the radiological appearance of the different components of mechanism of action by MR imaging methods: differentiate effects on blood brain barrier normalization, damage to tissue and partial blood volume/flow; to differentiate between effect on tissue and effects on blood vessels by applying CED; carry out an imaging study with GBM patients to develop a model that will depict tumors in correlation with DWI and clinical status; for patients undergoing surgery due to clinical deterioration, a correlation with histological samples may be possible; provide an imaging study with human glioma bearing mice to test the validity of the method on animals by comparison with histology, and find correlation between pre-treatment calculated parameters and later response/or treatment failure. Assuming the effects on the tissue are found dominant—an animal study may study the feasibility of increasing treatment effects (and not side effects) by CED of Bevacizumab.

Additional Studies:

Animal Study:

human glioma (u87) bearing nude mice are scanned using various MR sequences before and after treatment of bevacizumab. These MR sequences include serial contrast enhanced T1 SE, perfusion and diffusion weighted images, as well as T2/FLAIR images. Various Parameters are calculated and their correlation with response or lack of response, determined by histological analysis and by changes in tumor growth assessed by MRI, are studied.

Clinical Imaging Study:

The radiological biomarkers determined from the animal study are further applied in a clinical imaging study involving 20 patients with recurrent glioblastoma who failed the standard first line therapy and are candidates for Bevacizumab therapy. The patients are scanned before initiation of Bevacizumab treatment and 1 week, 1 month, 3 months and 5 months thereafter. Calculated biomarkers are compared to treatment outcome and histology, when possible.

CED Animal Study:

is performed in a rat brain tumor model. Rats are divided into 4 groups: the first group is treated with CED of bevacizumab, the second is injected IV with bevacizumab and the control groups are treated with saline.

The rats are scanned by MRI, using T1 weighted MRI for assessment of CED efficacy immediately post treatment, T2-weighted and DWMRI for early cytotoxic response 24 hours post treatment and the mean survival of the rats in the different groups are compared Materials & Methods Animal and Clinical Imaging Studies:

Animal Model:

Nude mice (n=20), 4-6 weeks of age are used in this study. For intracranial implantation, $10^5$ human U87 cells suspended in 6 µL of sterile PBS are injected into the striata of all the animals stereotacticly.

Animal Systemic Treatment:

starting from the fifth day of tumor implantation, animals are injected IP with 5 mg/kg Bevacizumab every 2 weeks.

Patients:

20 patients, 18-70 years of age, with recurrent glioblastoma (World Health Organization [WHO] grade IV astrocytoma) who failed the standard first line therapy and are candidates for Bevacizumab therapy are selected. Eligible patients would have a WHO performance status of 3 or less and adequate hematologic, renal, and hepatic function. Patients with recent (6 months) cerebrovacular event, active bleeding or recent (6 weeks) major surgical procedure are excluded. Patients with uncontrolled hypertension or unbalanced anticoagulation therapy are excluded as well (contraindications for Bevacizumab administration).

Patients Treatment:

Bevacizumab is given as IV infusion, 10 mg/kg body weight every 2 weeks (standard Bevacizumab regimen for GBM patients).

MRI Acquisition:

MRI is performed using a 3.0T GE system with the standard 8 channel head coil for the clinical imaging study and using a 1.5T GE system with the standard wrist coil for the animal imaging study. MRI scans include T2-weighted, T2 FLAIR, perfusion-weighted MRI and diffusion-weighted MRI (DWMRI) as well as high resolution spin echo T1-weighted MRI (T1-MRI) acquired before and at 6 time points after contrast injection (approx 1, 12, 20, 23, 30, 70 min post contrast). T1-MRI is acquired with TE/TR=22/240 ms, field of view 26×19.5 cm, 5/0.5 mm slice thickness and 512×512 pixels.

Image Analysis:

Delayed Contrast Extravasation MRI:

Image analysis is performed using MatLab (version R2006b, The MathWorks, Inc. Natick, Mass., US). The overall goal is to obtain subtraction maps, where the T1-MRIs of the $1^{st}$ series post contrast is subtracted from the T1-MRIs of the later series.

The subtraction maps depict spatial distribution of contrast accumulation/clearance in the tissue, blood vessels and CSF. In case of an intact blood brain barrier, due to clearance of contrast agent from the blood system, there is no increase in contrast accumulation after the first series, therefore the subtraction maps have values ≤0, appearing blue in the final permeability maps. The signal decay of the blood vessels is faster than that of the tissue (the signal is averaged over the tissue and microvasculature), therefore blood vessels have lower values than tissue. In case of subtle blood brain barrier leakiness, there is movement of contrast from the vasculature into the tissue, causing a shift in T1 and a signal increase on T1-MRI, thus the values in these regions are higher than in normal tissue and the subtraction maps have values ≥0, appearing red in the final permeability maps.

In order to increase the sensitivity to small changes it may be necessary to perform image pre-processing consisting of correction for intensity variations and whole body registration.

Correcting for Intensity Variations:

The signal intensity homogeneity throughout the image and between slices depends on various parameters such as the strength/homogeneity of the static magnetic field, the oscillating excitation field, the gradients, the sensitivity of the receiving coil and various parameters of the sampled tissue. The intensity correction may be performed on each image separately. An intensity variation map consisting of the large scale intensity variations may be obtained by applying circular smearing to the original image and then subtracting from the original image.

Rigid Body and Elastic/Local Registration:

Rigid body registration may be performed using a least squares approach and a 6 parameter (rigid body) spatial transformation with the SPM5 (Statistical parametric mapping) MatLab routine (an academic software kit by "Wellcome Trust Centre for Neuroimaging"). Since head movements cause changes in the magnetic field inducing distortions in the MRIs, it may be necessary to add local/ elastic registration by dividing each slice into a grid of 20×20 mm volumes. Each square volume may be allowed to move freely in x-y-z until the sum of the absolute values of the intensity difference between the two time points reaches a minimum. The resulting three 3D translation matrices may be smoothed using circular smearing and interpolated to obtain translation values per pixel. These high resolution matrices may then be applied to register T1-MRIs of the second time point to the location of the first time point.

Patlak Plots:

In a much generalized matrix analysis of compartmental dynamics, Patlak et al. demonstrated that the blood to-tissue transfer or influx constant, Ki, could be obtained by graphical analysis of a timed series of tissue and arterial concentrations. The working equation is:

$$C_{tis}(t) = K_i \int_0^t C_{pa}(\tau) d\tau + C_{pa}(\tau) \cdot V_p \quad [\text{Eq. 1}]$$

Where: $C_{tis}(t)$ is the tissue concentration of indicator (per unit weight) at the end of the experimental period (t); $C_{pa}(\tau)$ is the arterial plasma concentration (per unit volume) at a series of times over the duration of the experiment and is used to calculate the arterial concentration-time integral; $K_i$ is the blood-to-brain transfer constant of the indicator; and $V_p$ is the tissue volume in which the blood-borne indicator mixes prior to crossing the rate-limiting barrier. This volume includes the plasma space in all instances and other intravascular and capillary wall compartments in special cases. In a graphical analysis based on Eq. [1], the ratio Ctis(t)/Cpa(t) forms the ordinate, while the quantity _0 t Cpa_d_/_Cpa_t_ forms the abscissa.

CED-Animal Study

Solutions containing combinations of saline, sucrose (for enhanced distribution efficacy) and Bevacizumab in different concentrations are mixed with Gd-DTPA (1:70) (for enabling real-time imaging of the drug distribution) and infused into the striatum of tumor bearing rats (males, 250-300 g). T1-weighted MRI are acquired immediately post-treatment to assess the extent of convection. Rats' weight and survival may be documented, and the mean survival of the rats in each group may be compared.

Convection-Enhanced Drug Delivery Procedure:

Under full anesthesia, a midline scalp incision is made to identify the bregma. A 1 mm burr hole is made in the right region of the skull, 3 mm anterior and 2 mm lateral to the bregma. A 30-gauge needle attached to a 1 mL syringe (Gastight, Hamilton, Reno, Nev.) may be placed stereotactically 5.5 mm deep into the striatum. The infusion uses a BASI syringe pump at a rate of 2 μL/min for a duration of 20 minutes.

Calculation of Convection-Enhanced Drug Delivery Extent:

The volume (in mm³) of infusate distribution may be calculated from the T1-weighted MRI acquired immediately post-CED treatment. Regions of interest are defined over the entire enhancing region in each slice (excluding the ventricles). The number of pixels in the regions of interest may be counted and multiplied by the volume of a single pixel.

Preliminary Results:

Two GBM patients who failed first line chemoradiation were given Bevacizumab as an IV infusion, 10 mg/kg body weight every 2 weeks (standard Bevacizumab regimen for GBM patients).

The patients were recruited before Bevacizumab treatment was initiated. They underwent the first MRI exam prior to treatment. Second and third MRI exams are performed 1 week and 1 month after the administration of the first Bevacizumab dose. Two more MRI exams are performed at 3 and 5 months post initiation of treatment.

Vessel function maps were calculated at 15 and 75 min after contrast injection. Examples of two patients with 3 GBM lesions with different presentations of response to Avastin, are shown below. The response pattern to Avastin and the physiological meaning of the observed changes in the maps, are being studied.

Reference is now made to FIG. 8, which shows a GBM lesion of patient #1 at baseline (top), 1 week after Avastin treatment (middle) and 1 month after treatment (bottom). It can be seen that the lesion became more prominently blue after the first week of treatment with minor changes in the 1 month follow-up. FIG. 9 is a zoomed view of FIG. 8.

FIG. 10 shows recurrent GBM lesion (post surgery and standard chemoradiation) of patient #1 of example 2 at baseline (top), 1 week after Avastin treatment (middle) and 1 month after treatment (bottom). It can be seen that in this lesion there was a decrease in the blue component in the first week post treatment and then an increase 1 month later.

FIG. 11 is a zoomed view of FIG. 10.

Reference is now made to FIG. 12, which relates to a patient #2 in example 2, who was recruited after failing standard chemoradiation and 1 month after undergoing a second resection. His tumor induced significant edema and pressure on adjacent brain as shown in the baseline MRI (top). 1 week after the first treatment with Avastin, it can be seen that the pressure on the brain is relieved, the edema is somewhat relieved as well, the red component of the lesion has significantly decreased but the blue component seems more concentrated, and has not decreased.

FIG. 13 is a zoomed view of FIG. 12.

Example 3

The present embodiments were used in high resolution depiction of brain metastases and other brain disorders after treatment with radiosurgery or other radiation-based treatments for differentiation between tumor progression and radiation necrosis, and in application of high resolution delayed extravasation MRI for differentiation between progression of brain Space occupying lesion (SOL) and treatment effects following radio-surgical treatment.

Patients and Treatment:

32 patients are used in the study, 15-75 years of age, post radio surgical treatment of 18-20 Gy targeting a brain SOL with follow up MRIs that may be related to tumor progress or treatment effects. The patients are divided into the following 4 groups:

(1) 6-8 patients with suspected SOLs (brain metastases, AVMs, primary brain tumors or meningiomas) progression.

(2) a control group of the same number (6-8) of patients with similar pathologies who underwent a radio surgical treatment within a similar time interval (±2 months) as the first group.

(3) 6-8 patients with suspected treatment effects.

(4) a control group of the same number (6-8) of patients with similar pathologies that had radio surgical treatment within a similar time interval (±2 months) as the third group.

All patients are recruited at least 3 months post stereotactic radiotherapy.

MR Imaging:

Patients undergo the 1$^{st}$ MRI immediately after recruitment. This exam is longer than the follow-up exam in an attempt to acquire data at long periods after the contrast injection, thus enabling sensitivity to the slow permeability population. Follow-up MRIs are performed every 3 months up to one year. The MRI exams are performed on a 1.5T or 3.0T GE MR system using the standard GE head coil. Pre- and post-contrast T1, T2, FLAIR and DWMRI are performed using a conventional dose of the contrast agent. In addition, serial post-contrast T1-MRI are acquired up to 30 min after contrast injection. At this time (only for the first MRI) the patient may be taken out of the MRI but is asked to return again after 45 min for a short acquisition of T1-MRI and FLAIR MRI. BBB functioning maps are calculated from the post contrast T1-MRIs. Gd leakage into the CSF are calculated from the FLAIR images. Diffusion characteristics are calculated from the DWMRIs. The outcome of the analysis may identify specific MRI-based parameters for differentiation between radiation related brain injury and progression.

The preliminary results in 8 patients with brain metastases are shown in FIG. 14. The figure demonstrates the ability of vessel function maps, calculated from images acquired 6 and 14 min on average after contrast injection, to depict various vessel populations within the tumor. All patients and all metastases presented a blue component, consistent with the assumption that the blue component represents tumor tissue. A1, B1, C1 are the conventional contrast-enhanced MRI. A2, B2, C2 are subtraction maps calculated from images acquired 6 min after contrast injection. A3, B3, C3 are subtraction maps calculated from images acquired 14 min after contrast. It can be seen that in the maps calculated from the later images, there are larger regions with slow (yellow/red) BBB disruption. Examples of regions showing increased slow permeability at the later time point are pointed to by arrows.

Three patients suspected for radiation necrosis have undergone surgery so far. In all three cases, regions appearing blue in our maps were correlated with morphologically active tumor while red regions correlated with non tumor tissues.

FIGS. 15-20 refer to a patient with brain metastases of adenoid cystic carcinoma. The patient experienced significant clinical deterioration and was suspect for radiation necrosis. FIGS. 15 and 16 show a carcinoma at 400 and 600 magnification respectively. Comparison of the maps of the present embodiments with stereotactic biopsies are shown in FIGS. 15 to 22.

FIG. 17A shows contrast-enhanced MRI of a Adenoid cystic carcinoma brain metastases.

FIG. 17B is the corresponding subtraction map calculated from the 2 min and the 75 min MR images showing part of the metastases in which approximately 60% is determined by the maps to consist of morphologically active tumor (blue), and approximately 40% is non-tumoral tissues consisting of tumor necrosis and treatment effects (red).

FIG. 17C shows a zoomed presentation of 17B.

FIGS. 18A to 18C are similar to FIGS. 17A to 17C but instead show the base or posterior part of the tumor;

FIG. 19 shows histology corresponding to the red region in map shown in FIGS. 17B and 17C.

FIG. 20 shows histology corresponding to the red region in the map shown in FIGS. 17B and 17C.

FIGS. 21A-21C show another slice of the same tumor.

In FIG. 21A tiny fragments of tumor within cauterized brain tissue, and blood vessels with thick lumens are seen. Radiation changes are also present. Central part: ~60% tumor, ~40% radiation necrosis. Significant cauterize artifacts.

FIG. 21B shows a medial superior anterior: Fragments of tumor (~15-20%) and brain tissue showing radiation necrosis. Significant cauterization artifacts can be seen.

FIG. 21C indicates a medial and posterior part: Fragments of tumor and (larger) regions of radiation necrosis and blood. Significant cauterize artifacts can be seen.

FIG. 22 shows histology corresponding to a blue region in FIGS. 21B-21C.

Example 4

In the present example, a methodology based on delayed contrast extravasation MRI is applied according to some embodiments of the present invention for calculating delayed enhancement subtraction maps. This depicts temporal enhancement characteristics with high resolution and high sensitivity to subtle BBB disruption [Israeli D, Tanne D, Daniels D, et al. The Application of MRI for Depiction of Subtle Blood Brain Barrier Disruption in Stroke. Int J Biol Sc. 2011; 7:1-8]. In order to confirm the application of the maps of the present embodiments for differentiating tumor tissues from non tumoral tissues, pre-surgical maps of patients with primary or metastatic brain tumors have been compared with histological assessment of resected tissue samples.

Materials and Methods

Patients and Treatment

The study was conducted after approval of the local ethics committee at Sheba Medical Center. Written informed consent was obtained from all patients.

Ten patients with primary brain tumors and 10 patients with brain metastases were recruited prior to surgery and scanned by conventional and delayed contrast extravasation MRI. In all 20 patients pre-surgical delayed enhancement subtraction maps were compared with histological findings. In addition, the application of the maps of the present embodiments for prediction of progression was studied in a small cohort of 13 newly diagnosed GBM patients undergoing standard chemoradiation and followed up to 19.7 months post therapy.

One group of patients included patients having primary brain tumor. The group consisted of 8 patients with histologically confirmed glioblastoma (World Health Organization [WHO] grade IV astrocytoma) of which 3 were newly diagnosed patients, 4 progressed following chemoradiation (60 Gy in 30 daily fractions, 5 days a week, with concomitant daily temozolomide of 75 mg/m$^2$ for 42 days. Chemoradiation was followed by adjuvant temozolomide of 150-200 mg/m$^2$ daily for 5 days every 28 days.) and one patient with secondary GBM was recruited 2 years after resection of an Anaplastic Astrocytoma (WHO grade III tumor) and chemoradiation. Two patients with newly diagnosed Anaplastic Oligodendrioma (WHO grade III tumor) were recruited as well.

The mean age of this group of patients was 58.6±3.6 with a range of 37-80. Nine of the 10 patients were men.

Another group of patients included patients with brain metastases. This group consisted of 4 patients with breast cancer metastases, 4 with non small cell lung cancer (NSCLC) metastases, 1 with malignant melanoma metastases and 1 patient with adenoid cystic carcinoma metastases. All patients were treated with a single dose of 18-20 Gy (to the 80% isodose line) LINAC based SRS 13.1±2.9 months prior to resection.

The mean age of this group of patients was 50.2±4.0 with a range of 30-67. Four of the 10 patients were men.

An additional group consisted of 13 newly diagnosed GBM patients. The patients in this group were scanned by conventional and delayed extravasation MRI 3-4 weeks after chemoradiation and every 2 months thereafter. Patients with clinical deterioration underwent additional MRI exams at the discretion of the physician. These patients were followed for 2-19.7 months. Eight of the later have progressed while 5 remained progression free.

The mean age of this group of patients was 54.3±4.1 with a range of 28-72. Eight of the 13 patients were men.

Inclusion criteria for all patients included WHO performance status of 2 or less and adequate hematologic, renal, and hepatic function. Exclusion criteria included contraindications to MRI and stable condition to undergo an MRI exam.

MRI Data Acquisition:

MR images were acquired using a clinical General Electric 3.0 T MRI machine (GE Medical Systems, Waukesha, Wis., USA) with the HD12 operating system, gradients intensity of up to 4.3 Gauss/cm and the standard GE phased array head-coil. MR sequences included T2* perfusion-weighted MRI (PWI), Fast spin-echo T2-weighted MRI, T2 FLAIR and echo-planar diffusion-weighted MRI (DWMRI). High resolution spin-echo T1-weighted MR images (T1-MRIs) were acquired before and at 3 time points after contrast injection: 2.6±0.1 min (immediately after the PWI sequence), 15.4±0.4 min and 75.3±0.7 min on average. These times are referred to below as the 2 min, 15 min and 75 min time points throughout. In order to minimize the burden on the patients, they were scanned up to 30 min after contrast injection, and were then asked to return for a short scan 75 min after contrast injection. T1-MRI was acquired with TE/TR=22/240 ms, field of view 26×19.5 cm, 5/0.5 mm slice thickness and 512×512 pixels. A standard single dose (0.2 ml/Kg) of Gd-DOTA (Dotarem, 0.5 mmol/mL, Guerbet, 95943 Roissy CdG Cedex, France) was injected intravenously using an automatic injection system 6 seconds after starting the PWI sequence.

MRI Data Analysis:

All image analysis was performed using MatLab (version R2006b, The MathWorks, Inc. Natick, Mass., US).

At least one goal of the analysis included obtaining delayed subtraction maps, where, according to some embodiments of the present invention, the T1-MRIs of the first series post contrast were subtracted from the T1-MRIs of later series. It was found by the present inventors that these maps depict spatial distribution of contrast accumulation/clearance in the tissue, blood vessels and CSF. For example, in case of normal blood vessels, due to clearance of contrast agent from the blood system, there is no increase in contrast accumulation in the late scans; therefore, the subtraction maps show negative values (blue in the maps). The signal decay of the blood vessels is faster than that of the tissue (where the signal is averaged over the tissue and microvasculature), therefore, blood vessels have lower values than tissue. In case of contrast accumulation, for example, regions where contrast clearance is slower than contrast accumulation, the maps show positive values (red in the maps).

The images were pre-processed by applying corrections for intensity variations and whole body image registration, as follows.

Correcting for Intensity Variations:

Signal intensity homogeneity throughout the image and between slices depends on various parameters including: strength and homogeneity of the static magnetic field, oscillating excitation field, gradients, sensitivity of the receiving coil and various parameters of the sampled tissue. An intensity correction was performed on each image separately by calculating an intensity variation map consisting of the large scale intensity variations. The later map was then subtracted from the original image.

Rigid Body and Elastic/Local Registration:

Rigid body registration was performed using least squares approach and 6 parameter (rigid body) spatial transformation with the SPM5 (Statistical parametric mapping) MatLab routine (an academic software kit by "Wellcome Trust Centre for Neuroimaging"). Since head movements affected the magnetic fields thus inducing distortions in the MRIs, it was advantageous to add local/elastic registration. The registration was performed by dividing each slice to a grid of 20×20 mm volumes. Each square volume was allowed to move freely in x-y-z until the sum of the absolute values of the intensity difference between the 2 time points reached a minimum. The resulting three 3D translation matrices were smoothed using circular smearing and interpolated to obtain translation values per pixel. These high resolution matrices were then applied to register T1-MRIs of the second time point to the location of the first time point.

Subtraction Maps:

Following the pre-processing, subtraction maps were calculated by subtracting the processed images of the series acquired 2 min after the contrast injection from a series acquired later on.

Enhancing Lesion Volume:

The enhancing portion of the lesions, depicted on conventional contrast-enhanced MRI, was calculated from the spin-echo contrast-enhanced T1-MRIs acquired 2 min after contrast injection. Regions of interest (ROIs) were defined over the entire enhancing region in each slice. A threshold, determined from intensity distribution histograms of the tumor and surrounding regions, was applied to the ROIs to include only enhancing portions of the tumor. The number of pixels in the enhancing portions of the ROIs were counted and multiplied by the volume of a single pixel. The resulting volume was referred to as the state of the art parameter for the assessment of tumor volume [Wen P Y, Macdonald D R, Reardon D A, et al. Updated response assessment criteria for high-grade gliomas: response assessment in neuro-oncology working group, J Clin Oncol. 2010; 28:1963-1972].

Histology:

A total of 32 stereotactic tissue samples and 8 resected lesions acquired from 10 patients with primary brain tumors and 10 patients with brain metastases patients were histologically examined and compared with the delayed enhancement subtraction maps of the present embodiments. Stereotactic locations for tissue samples were determined prior to surgery using the calculated subtraction maps which were co-registered to the conventional T1-MRIs, for 9 patients with primary brain tumors (20 tissue samples) and 4 patients with metastatic tumors (12 tissue samples) (Table 2). Existence/absence of morphologically active tumor in the histological analysis of 8 metastatic tumors acquired from 7 patients was compared with the pre-surgical maps as well (Table 3). Eight additional samples were obtained from one GBM patient, chosen by the neurosurgeon during surgery as representative samples (patient #3, Table 3).

All samples were marked by the neurosurgeon during resection and then fixed and stained by H&E according to the routine hospital procedure.

Histological interpretation was performed by a neuropathologist expert.

Morphologically Active Tumor:

"Morphologically active tumor" was defined as demonstrating one or more of the following characteristics: hyper cellularity, small cells, mitosis, high Ki67, pseudo-palisading necrosis and vascular proliferation.

Non-Tumoral Abnormal Tissue:

"Non-tumoral abnormal tissue" was defined as demonstrating one or more of the following characteristics: radiation changes including large, widely spaced atypical astrocytes, blood vessels hyalinization, fibrinoid material in vessels, proliferating small vessels and non palisading tumor necrosis.

Progression (GBM Patients Only):

Disease progression was diagnosed using standard MRI sequences. Each case was presented to the hospital tumor board, consisting of a neuro-oncologist, a neurosurgeon and a neuro-radiologist. The physicians were blinded to the delayed enhancement subtraction maps so that progression was diagnosed according to the RANO (revised Mcdonald's) criteria. When disease progression was determined, the patient's treatment was changed (surgery or Bevacizumab). The time from the first MRI follow-up to disease progression is listed for all patients in Table 4. In those patients with no disease progression, the time of the last follow-up was listed.

Time to Progression (TTP) (GBM Patients Only):

TTP was defined as the time from the end of chemoradiation till progression was determined.

Tumor Growth Rate (GBM Patients Only):

The feasibility of applying the delayed enhancement subtraction maps for prediction of TTP was demonstrated by studying the correlation between initial tumor growth rate and TTP. Initial tumor growth was calculated as (V−Vo)/Vo, where V was the tumor volume at the second follow-up and Vo was the tumor volume calculated from the first follow-up MRI (3 weeks after the end of treatment). Initial tumor growth rate was calculated by dividing the tumor growth by the time that passed between the first and second MRI follow-ups.

Statistical Methods:

Results for averaging over a group of values are presented below as average±standard error. Correlations were assessed by performing t-tests and calculating two-tailed p-values, unless otherwise stated. Prediction of TTP was assessed using the logrank test [Peto R, Peto J. Asymptotically efficient rank invariant test procedures. J Roy Stat Soc Series A. 1972; 135:195-206]. In view of the small number of patients involved, the p-values were calculated based on the permutation distribution [Moses L. Non-parametric statistics for psychological research. Psychol Bull 1952; 49:122-143]. In this method one calculates the logrank statistic for each possible allocation of the patients to the two predictor groups "high" and "low" preserving the number of patients in each group, and then calculates the p-value as the proportion of allocations that yield a logrank statistic equal to or higher than the one observed with the study data.

Results

FIG. 23 shows examples of enhancement subtraction maps. Examples of axial high resolution T1-weighted MR images acquired 2 min (A), 15 min (B) and 75 min (C) after contrast administration in a patient (#3) with newly diagnosed GBM undergoing standard chemoradiation are shown. Subtraction maps were calculated from the data acquired at 2 and 15 min (D) and 2 and 75 min (E) post contrast administration. Blue regions represent fast clearance of the contrast agent from the tumor while red regions represent slow accumulation of the contrast in the tissue. It can be seen that abnormal enhancement patterns in the 75 min map are depicted more clearly and over larger regions than in the 15 min map. The signal intensity of regions with different enhancement patterns as a function of time post contrast administration is shown in the plot. It can be seen that the red and blue components of the tumor enhance and decay at different rates.

FIG. 3 shows examples of histological determination of tumor and non-tumoral components—GBM. Examples of contrast-enhanced T1-weighted MRI (A-C), enhancement subtraction maps calculated from the 2 and 75 min data (D-F) and H&E stained histological samples of a rapidly growing lesion in patient #1 of this example with newly diagnosed GBM undergoing standard chemoradiation are shown. Data was acquired prior to surgery, 6 months after initiation of treatment. Samples were taken from a mixed blue and red region (A, D, arrows), a blue region (B, E, arrows) and a red region (C, F, arrows). Histological analysis reveals mixed regions of tumor and necrosis (G, magnification ×200), hypercellular tumor (H, magnification ×400) and radiation necrosis (J, magnification ×400), respectively.

FIG. 24 shows histological determination of tumor and non-tumoral components—brain metastases. Examples of contrast-enhanced T1-weighted MRI (A, E), enhancement subtraction maps calculated from the 2 and 75 min data (B, F) and H&E stained histological samples (C, D, G) of a cortical breast cancer brain metastasis. 24C and 24D show a necrotic region taken from the red region of the map shown in 24B (arrow). 24D shows tumoral tissue on the border of normal cortex, taken from a region of blue on the border of normal brain, pointed to by an arrow in image 24F. The arrows in FIGS. 24A and 24E correspond to the arrows in FIGS. 24B and 24F, respectively.

FIG. 25 shows examples of Histological determination of tumor and non-tumoral components—brain metastases. Examples of contrast-enhanced T1-weighted MRI (A), enhancement subtraction map calculated from the 2 and 75 min data (B), macro H&E stained histological sample (C, magnification ×20), tumor region from a peripheral region of the sample (D, magnification ×400) and radiation necrosis from the central region of the sample (E, magnification ×400) of a medial NSCLC brain metastasis of patient #23 of this example (metastasis #1), 1 year post radiosurgery, are shown. The metastasis was resected unblock and marked by the neurosurgeon to enable comparison with the MRI data. H&E staining shows a large central necrotic region surrounded by a rim of morphologically active tumoral tissue, in agreement with the subtraction map. It is also possible to see part of a necrotic blood vessel in the region of radiation necrosis (E) and scattered blood cells in the tissue.

FIG. 26 shows examples of vessel morphology. Examples of vessel morphology sampled from regions appearing blue in the maps of patients with primary brain tumors are shown in images A-F. Vessels from regions appearing red in the maps are shown in G-I. Samples D and G were taken from patient #4 of this example. Samples B, E, H and I were taken from patient #1 of this example. A and C were taken from patient #11 of this example and F was taken from patient #13 of this example.

It can be seen that the samples obtained from blue regions in the maps (A-F) present swollen endothelial cells, dilated lumen, peri-vascular dense fibrous tissue and glomeruloid lumen. Samples taken from red regions in the maps show different stages of vessel necrosis. The vessels shown in G show early necrosis, with scattered blood cells surrounding the necrotic vessels, while the vessels in H and I show later stages of vessel necrosis. The silhouette is reserved and there are residual red blood cells but the endothelial cells are necrotic.

FIG. 4 shows the enhancing of a portion of the lesion: Contrast-enhanced T1-weighted MRI without (A) and with (B) a mask selecting the enhancing portion of the lesion on conventional MRI. The enhancing portion of the lesion was calculated from the pixels marked pink in (B). Subtraction maps calculated at 15 min (C) and 75 min (D) demonstrate the contributions of the red/non-tumor and blue/tumor contributions to the enhancing portion of the tumor;

FIG. 27 shows examples of comparison with rCBV. Contrast-enhanced T1-weighted MRI (A, D, G), enhancement subtraction maps (B, E, H) and rCBV maps (C, F, I) of patients #6 (A-C), #3 (D-F) and #26 (G-I) are shown. Patient #6 of this example (GBM) shows a blue rim surrounding the surgery site, representing morphologically active tumor, in agreement with high rCBV values in the corresponding rCBV map. Patient #3 of this example (GBM) is a contradicting example, showing a massive lesion dominated by the blue population in the subtraction maps (confirmed by histology to consist of ~70% morphologically active tumor), in contrast to low rCBV values in the corresponding rCBV map. Patient #26 of this example (breast cancer brain metastases) shows a thin rim of the blue populations in our maps in agreement with a thin rim of increased rCBV values. The advantages of our vessel function maps over rCBV acquired using DSC in means of high resolution, high sensitivity to contrast and minimum sensitivity to susceptibility artifacts can be seen.

FIG. 28 demonstrates correlation with time to progression: The correlation between the late enhancement subtraction maps and time to progression was studied in a small cohort of 13 GBM patients post chemoradiation. Kaplan-Meier curves of time to progression in patients above and below the median of four predictors are shown: Initial fast volume (A), initial enhanced volume (B), initial fast growth rate (C) and initial enhanced growth rate (D). The curves are plotted for each predictor for patients above (black) and below (gray) the median. It can be seen that the initial fast growth rate predictor provides a near-significant difference between the two groups of patients, suggesting this predictor may be a candidate for prediction of time to progression.

FIG. 29 shows examples of progression and pseudoprogression in GBM patients post chemoradiation. Late enhancement subtraction maps of a patient (#6) with significant increase in the enhancing lesion due to increase in the red volume (A-C) representing pseudoprogression and a patient (#3) with significant increase in the blue component (D-F) with minor changes in the enhancing volume (representing progression) are shown. In the first example, the total enhancing volume has increased by 34% from 3 weeks (A) to 4.2 months (B) post chemoradiation, and then decreased to 33% below the initial volume (C) 9 months post treatment. The blue volume slightly increased by 6% in the first 4 months (A, B) and then significantly decreased to 47% below the initial volume at 9 months (C) while the red volume increased by 51% in the first 4.2 months (A, B) and decreased to 13% above the initial volume by 9 months (C). This patient progressed 11.6 months post treatment. In the second example, the total enhancing volume has increased by 16% from 3 weeks (D) to 2.5 months (E) and then remained 17% above the initial volume (F) 6.5 months post treatment. The blue volume slightly increased by 2% in the first 2.5 months (D,E) and then significantly increased to 57% above the initial volume at 6.5 months (F) while the red volume increased by 39% in the first 2.5 months (D, E) and decreased to 61% below the initial volume by 6.5 months (F). This patient progressed 6.5 months post treatment when he was referred to surgery.

Delayed Enhancement Subtraction Maps:

Enhancement subtraction maps were calculated using the data acquired 15 (15 min maps) and 75 min (75 min maps) after contrast injection. Two primary enhancement patterns were found in the maps: One characterized by slower contrast clearance than contrast accumulation at the delayed time point relative to the 2 min time point (positive signal, colored red in the maps) and the other by faster clearance than accumulation (negative signal, colored blue in the maps). Normal brain regions, due to the intensity variation correction, had an average value of zero (green). Examples of 15 and 75 min maps are shown in FIG. 23. As shown, the fast (blue) region in the 75 min map is depicted more clearly and over larger regions than in the 15 min map. Examples of the signals intensities of the fast and slow regions as a function of time after contrast injection are shown as well, demonstrating the different rates of contrast accumulation and clearance of these regions.

Histology, Tumor Versus Non Tumoral Tissues

Thirty two stereotactic samples acquired from 9 patients with primary brain tumors and 4 patients with brain metastases undergoing surgery were compared with our pre-surgery calculated maps. The samples were taken from fast (blue) regions according to the maps, slow (red) regions, and regions consisting of mixed fast and slow components. Histological evaluation confirmed for all samples the discrimination between fast regions, determined to consist of morphologically active tumor, and slow regions, consisting of non-tumoral tissues. Regions consisting of both fast and slow components in the maps consisted of tumor and non-tumoral tissues in the histological samples (FIGS. 3-25, Table 2).

Patient #3 (Table 3) with a newly diagnosed GBM underwent a second resection 6 months after chemoradiation due to clinical deterioration. The patient died 10 days post-surgery. The maps calculated from his last MRI scan, showed that the fast component reached 71±3% of the enhancing lesion volume. Histological analysis was performed for 8 samples taken from 2 main regions of the lesion. In both regions the tumor load was estimated by the neuro-pathologist to cover ~70% of the examined samples, in agreement with the maps calculated according to some embodiments of the present invention.

Eight additional metastases acquired from 7 patients, showed a fast component in the maps of the present embodiments and were confirmed by histology to consist of morphologically active tumor (FIGS. 24-25, Table 3).

Histology, Blood Vessels

The morphological appearance of blood vessels in the fast and slow regions of the maps of the present embodiments has been examined. Typical fast population vessel morphology consisted of proliferating endothelial cells, dilated lumen, peri vascular fibrosis and glomeruloid vessels. The outline of the vessels lumens in these regions seemed to be undamaged. Vessels in the slow regions, on the other hand, presented different stages of vessel necrosis with significantly damaged lumens. In most vessels a silhouette of the vessel wall could still be recognized, but only rarely residual endothelial cells could still be detected. In some cases scattered blood cells were seen in various distances from the necrotic vessel. Examples are shown in FIGS. 3-5.

Significance of Long Delays

The volumes and intensities of the fast population, calculated from the 75 min maps, were found to be significantly different then those calculated from the 15 min maps (data calculated from 30 MRI exams of the 30 recruited patients): r=0.91, p<0.0001 and r=0.79, p<0.0001, respectively (Wilcoxon matched-pairs signed-ranks test). The average ratio between the volumes of the fast population calculated from the 75 min maps and the volumes calculated from the 15 min maps was 2.0±0.3 and the average ratio between the intensities of the fast population at the two time points was 1.8±0.1, suggesting increased sensitivity to tumor tissues at the longer delays. There was no significant difference in this increased sensitivity between the primary brain tumor and the brain metastases groups.

Correlation with Conventional MRI:

The volume of the fast population was found to correlate significantly with the enhancing lesion volume (representing the conventional tumor volume): r=0.94, p<0.0001 (based on 30 acquired MRI exams). According to the maps of the present embodiments, in this cohort of patients 48.4±1.9% (on average) of the enhancing lesion on conventional MRI did not represent morphologically active tumor (FIG. 4). For example, the maps of the present embodiments shows that 55%, 38%, 39%, 56% and 83% of the enhancing lesions presented in FIGS. 23, 3, 4, 27A and 27D respectively, consisted of the fast population. There was no significant difference in the average percentage of the fast population between the primary brain tumor and the brain metastases groups.

Significant correlation was also found between fast population volume×intensity and rCBV calculated from PWI (r=0.69, p<0.005), suggesting that rCBV may be a dominant characteristic of the fast population. Examples are shown in FIG. 27.

Correlation with TTP (GBM Patients):

13 newly diagnosed patients were followed by conventional and delayed-contrast extravasation MRI. The follow-up periods of each patient are listed in Table 4. Four parameters were studied as possible predictors for progression: Initial fast volume, initial enhancing volume, initial fast growth rate and initial enhancing growth rate. Kaplan-Meier curves of TTP in patients above and below the median of each predictor are shown in FIG. 28. The p values were calculated with the log rank test using the permutation distribution. As shown, the initial fast growth rate provides a near-significant difference between the two groups of patients, unlike the other predictors, suggesting that this predictor may be a candidate for prediction of TTP.

Progression and Pseudo-Progression in GBM Patients Post Chemoradiation:

Within the cohort of GBM patients with follow-up, for 7 of the 8 progressing patients, progression was determined in the first MRI follow-up in which significant increase in the fast component volume was noticed. For one patient progression was determined 5 weeks after the increase in the fast component. While an increase in the fast component preceded progression in all patients, significant increase of the enhancing lesion volume was not necessarily followed by progression. An example of a patient who experienced significant increase in the enhancing lesion volume 4.2 months post treatment but remained progression free for an additional 7.4 months is shown in FIGS. 29A-C. An example of a patient who experienced significant increase in the fast volume 6.5 months post treatment (with no significant increase in the enhancing lesion volume) is shown in FIGS. 29D-F. This patient was determined to progress 6.5 months post treatment and underwent surgery.

Discussion

GBM is the most common and most aggressive type of primary brain tumor in humans. The current standard of care for newly diagnosed GBM is surgical resection (when possible) followed by radiotherapy with concomitant and adjuvant temozolomide chemotherapy. The rate of early treatment induced radiological changes which mimic tumor progression—pseudoprogression—increased significantly since the addition of chemotherapy to the treatment regimen. Due to the increasing occurrence of brain metastases and the expending use of radiosurgery to treat them, the rate of treatment-induced radiation necrosis is rising as well. Conventional MR imaging is currently unable to provide reliable distinction between tumor recurrence and treatment effects.

A significant advantage of the delayed enhancement and clearance rates according to some embodiments of the present invention is the ability to apply sequences with lower temporal resolution, such as high resolution spin-echo T1-MRI. This is unlike the commonly studied early rates (DCE and DSC).

The sequences of the present embodiments significantly reduce susceptibility artifacts while providing high signal-to-noise ratios, high resolution and high sensitivity to contrast variations. Without wishing to be bound to any particular theory, the present inventors believe that by measuring the clearance of the contrast agent from the tissue at these long delays the sensitivity to physiological parameters is increased, providing additional information unattainable when using short acquisition times. This assumption is supported by the two fold increase in sensitivity to tumoral (fast) tissue obtained by increasing the delay from 15 to 75 minutes. In this context it is noted that the patients were not held in the scanner for these long times. The patients are scanned for 30 min post contrast injection and then asked to return for an additional short scan of the 75 min point.

The results presented herein demonstrate significant correlation of the fast component with high rCBV values, suggesting that rCBV may be a dominant characteristic of this population. The low rCBV values in fast regions of the subtraction maps constructed for some patients may be explained by distortion of the PW images in this population of post-surgery patients due to close vicinity of the tumor to surgical screws. Distortion may also be induced by hemorrhages which are frequent in these tumor types. In some cases the low rCBV values may be explained by the low resolution of the PW images impeding the sensitivity to small tumoral regions in contrast to the high resolution/sensitivity of the maps. The present inventors also contemplate that other contributions to the fast component, such as increased vessel permeability, may exist.

The most pronounced effect depicted in the delayed enhancement subtraction maps of the present embodiments is the clear differentiation between fast and slow populations, where the terms "fast" and "slow" refer to the clearance rate of the contrast agent between the early time point (2 min) and the delayed time point (75 min). The common feature of vessels morphology in the fast regions was found to be the undamaged vessels lumens, while vessels in the slow regions presented significantly damaged lumens. Therefore, an explanation for the difference between the 2 populations may be that vessels in the fast regions provide efficient contrast clearance from the tissue, while the damaged lumens in the slow regions are unable to clear the accumulating contrast efficiently, resulting in contrast accumulation.

The association between the fast/slow components of the maps and tumor/non-tumoral tissues as determined by histological analysis is currently based on 32 biopsy samples obtained from 9 patients with primary brain tumors and 4 patients with brain metastases. Additional confirmation was obtained from 1 GBM patient and 8 metastases resected from 7 patients. These data suggest that the subtraction map, calculated according to some embodiments of the present invention from delayed contrast extravasation MRI, enable clear differentiation between tumor and non-tumoral tissues in various types of brain tumors.

The manner of which the maps of the present embodiments may be applied for differentiating progression from pseudo-progression in GBM patients post chemoradiation is demonstrated in FIG. 29.

In the maps of some embodiments of the present invention, progression is reflected by a significant increase in the fast component of the enhancing lesion while pseudoprogression is reflected by an increase in the slow component with no significant increase in the fast component. Thus, using the maps of the present embodiments in routine MRI follow-up may aid the physician in determining progression versus pseudoprogression in patients presenting an increase in the enhancing lesion on T1-MRI. An increase in the fast component volume, suggesting progression, implies that a change in the current therapy should be employed. No significant increase in the fast volume component, suggesting pseudoprogression, implies that the patient is responding to the current therapy and thus continuation is preferred, if possible.

The maps of the present embodiments may be applied in a similar manner to patients following SRS. For example, patients with growing volumes of the slow component can be recommended for follow-up, if possible, while patients with growing volumes of the fast component can be recommended for treatment such as surgery or repeated SRS.

The ability of the maps of the present embodiments to depict morphologically active tumor regions with high resolution can be applied for optimizing radiation treatment planning by localizing the treatment to the fast/blue regions in the maps. This methodology can optionally and preferably be applied in post surgery scenario to allow differentiation between post surgical changes and tumor remnants thus allowing depicting and treating residual tumor post surgery.

High resolution depiction of tumoral tissues can also be beneficial in the planning of surgical resections, especially in the case of close proximity to functionally eloquent brain regions. In these cases, determination of the exact extent of the tumor can be advantageous for the decision whether microsurgical tumor removal might be warranted.

The maps of the present embodiments may also be applied for guiding stereotactic biopsies for molecular classification of the tumor. In this case the maps may aid in preventing the acquisition of biopsies with a high amount of necrosis or out of the infiltration zone with 'contamination' of the specimen by normal brain tissue, both potentially leading to false-negative results.

Novel approaches for local drug delivery including injections, infusions, trans-nasal delivery, convection enhanced delivery, local BBB disruption and various types of polymeric implants may also benefit from the application of the maps of the present embodiments, for example, for the purpose of planning and monitoring the treatments.

Increased tumor vascularity has been shown to correlate with both shortened survival and higher grade of malignancy in gliomas. Consequently, anti-angiogenic agents such as Bevacizumab, a monoclonal antibody targeting vascular endothelial growth factor, are now commonly employed to treat progressive malignant gliomas. The wide-spread use of these agents has added a layer of complexity to the evaluation and characterization of malignant gliomas as these agents have been shown to rapidly and markedly decrease contrast enhancement on contrast-enhanced T1-MRI. Example 5 below describes a study in which the subtraction maps of the present embodiments are applied for to recurrent GBM patients treated by Bevacizumab.

The high sensitivity of the maps of the present embodiments can provide additional information for delineation of the tumor borders as well as for targeting stereotactic biopsies. The results presented herein demonstrate the applicability of the technique of the present embodiments in the daily clinical scenario. The ability to clearly differentiate tumor from non-tumoral tissues provides the physician with a clear understanding of the patient current situation thus enabling improved patient management.

TABLE 2

List of 32 biopsied samples, delayed enhancement subtraction map characteristics and histological evaluation of 9 patients with primary brain tumors and 4 patients with brain metastases

| Sample # | Patient # | delayed enhancement population | Histological description | Tumor type |
| --- | --- | --- | --- | --- |
| 1 | 1 | Mixed regions of red, blue and green populations | One cellular region consisted of small cells with no mitoses. Proliferation was seen in 5% of the cells by Ki67 staining, implying active tumor. Other regions showed post radiation changes. One region was of brain parenchyma with no obvious abnormalities | GBM post chemoradiation |
| 2 | 1 | Cortical region of blue | Subcortical infiltrating zone of | GBM post chemoradiation |

TABLE 2-continued

List of 32 biopsied samples, delayed enhancement subtraction map
characteristics and histological evaluation of 9 patients with primary
brain tumors and 4 patients with brain metastases

| Sample # | Patient # | delayed enhancement population | Histological description | Tumor type |
|---|---|---|---|---|
| | | population and deeper white matter region of red population | active tumor with rare mitosis and a deeper, white matter region of post radiation changes. Ki67 staining of the active tumor zone showed proliferation in 3-5% of the cells | |
| 3 | 1 | Region of blue population | Active tumor consisting of a hypercellular area of small cells. Ki67 staining showed proliferation in 10-12% of the cells | GBM post chemoradiation |
| 4 | 1 | Mixed regions of blue and red populations | Regions of active tumor consisting of a hypercellular area of small cells and regions of post radiation changes. Ki67 staining in the active tumor region showed proliferation in 10-12% of the cells | GBM post chemoradiation |
| 1 | 4 | Region of red population | Radiation necrosis | GBM post chemoradiation |
| 2 | 4 | Cortical region of blue population and white matter region of red population | Cortical region shows active tumor accumulating focally beneath the meninges. Focal proliferation of blood vassals and palisading necrosis are identified as well. Most of the deeper white matter region show radiation necrosis | GBM post chemoradiation |
| 1 | 11 | Region of blue population | Highly cellular tumor with small regions of tumor necrosis with and without pseudo palisading regions of proliferating blood cells | Secondary GBM post chemoradiation |
| 2 | 11 | Region of blue population | Highly cellular tumor | Secondary GBM post chemoradiation |
| 3 | 11 | Region of blue population | Highly cellular tumor with small regions of tumor necrosis with and without pseudo palisading regions of proliferating blood cells | Secondary GBM post chemoradiation |
| 4 | 11 | Region of blue population | Highly cellular tumor with large proliferating vessels and small regions of tumor | Secondary GBM post chemoradiation |

TABLE 2-continued

List of 32 biopsied samples, delayed enhancement subtraction map
characteristics and histological evaluation of 9 patients with primary
brain tumors and 4 patients with brain metastases

| Sample # | Patient # | delayed enhancement population | Histological description | Tumor type |
|---|---|---|---|---|
| | | | necrosis with palisading regions of proliferating blood cells | |
| 1 | 13 | Region of blue population | Tumor consisting of atypical cells, mitoses and proliferating vessels | Newly diagnosed GBM |
| 1 | 14 | Region of blue population | Tumor consisting of atypical cells and numerous mitoses | GBM post chemoradiation |
| 2 | 14 | Border between a red region and a blue region | A region of necrosis with scanty nuclear dust and a region of tumor with pleomorphism and small regions of palisading necrosis | GBM post chemoradiation |
| 1 | 16 | Border between a red region and a blue region | Necrotic region including necrotic blood vessels and nuclear dust and a cellular tumor region with atypical cells, mitoses and vascular proliferation | Newly diagnosed GBM |
| 2 | 16 | Region of blue population | Tumor region with small foci of palisading necrosis | Newly diagnosed GBM |
| 1 | 17 | Region of blue population | Highly cellular tumor with small necrotic foci | Newly diagnosed GBM |
| 1 | 19 | Region of blue population | Regions of high cellularity and of low cellularigy typical of oligodendroglioma tumors | Newly diagnosed analplastic oligodendroglioma |
| 1 | 20 | Region of red population on the border of a blue population | Mostly necrotic tissue including necrotic blood vessels. Small foci of tumor are present | Newly diagnosed analplastic oligodendroglioma |
| 2 | 20 | Region of blue population on the border of a red population | Most of the tissue is tumor. One small area of necrosis at the periphery of the section | Newly diagnosed analplastic oligodendroglioma |
| 3 | 20 | Region of blue population on the border of surrounding brain | Mostly tumor tissue bordered by brain tissue infiltrated by tumor | Newly diagnosed analplastic oligodendroglioma |
| 1 | 21 Metastasis #1 | Sample taken from a blue region bordered by a green region on one side and a red region on the other | A sample showing a region of morphological active tumor bordered by normal cerebellum tissue on one side and necrotic tissue on the other | Sample taken from NSCLC cerebellar brain metastasis |

TABLE 2-continued

List of 32 biopsied samples, delayed enhancement subtraction map characteristics and histological evaluation of 9 patients with primary brain tumors and 4 patients with brain metastases

| Sample # | Patient # | delayed enhancement population | Histological description | Tumor type |
|---|---|---|---|---|
| 2 | 21 Metastasis #1 | Sample taken from a red region bordered by a blue region | A sample showing a large necrotic region borders by tumor | Sample taken from NSCLC cerebellar brain metastasis |
| 1 | 27 | Mixed area of blue and red regions | A mixture of active tumor regions and necrotic regions | Sample taken from NSCLC cortical brain metastasis |
| 2 | 27 | Blue region with small red foci on the border of surrounding brain | Several small samples of active tumor, tumor necrosis and edematous brain | Sample taken from NSCLC cortical brain metastasis |
| 1 | 29 | Red region on the border of surrounding brain | Radiation induced gliotic brain tissue | Sample taken from breast cerebellar brain metastasis |
| 2 | 29 | Mixed blue and red region on the border of surrounding brain | cerebral tissue and mixed regions of tumor and radiation necrosis | Sample taken from breast cerebral brain metastasis |
| 3 | 29 | Mixed blue, green and red regions | tumor, cerebral tissue and radiation necrosis with ecstatic blood vessels | Sample taken from breast cerebral brain metastasis |
| 4 | 29 | A red region bordered by surrounding brain on one side and a blue region on the other | Gliotic brain and radiation necrosis with a small tumor mass | Sample taken from breast cerebral brain metastasis |
| 1 | 30 | Red region surrounded by a blue rim | small regions of tumor (~30% of the sample) within larger region of necorosis (~70% of the sample) | Sample taken from breast cortical brain metastasis |
| 2 | 30 | Blue region on the border of surrounding brain | small tumoral region on the border of normal cortex | Sample taken from breast cortical brain metastasis |
| 3 | 30 | Blue region on the border of surrounding brain | Highly cellular tumor adjacent to normal cortex | Sample taken from breast cortical brain metastasis |
| 4 | 30 | Red region bordered by small blue region on one side and surrounding brain on the other | mostly necrosis with small foci of tumor and adjacent normal brain | Sample taken from breast cortical brain metastasis |

TABLE 3

List of tumors with no stereotactic biopsies, delayed enhancement subtraction map characteristics and histological evaluation of 1 patient with primary brain tumor and 7 patients with brain metastases

| Patient # | delayed enhancement population | Histological description* | Tumor type |
|---|---|---|---|
| 3 | Overall enhancing lesion consists of 71% blue population and 22% red population | Cellular tumor with many mitoses and regions of "geographic necrosis". In some regions of the tumor it is also possible to see proliferative blood vessels. Some regions surrounding the tumor (not in all slices and not all around the tumor) depict brain tissue infiltrated by a small number of tumor cells. The main findings in these regions around the tumor are abnormal proliferation of blood vessels and many histiocytes | GBM post chemoradiation |
| 21 Metastasis #2 | lesion consisting of blue (58%) regions and red (31%) regions | Metastatic carcinoma showing squamoid features with extensive areas of tumor necrosis | NSCLC cortical brain metastasis |
| 22 | lesion consisting of blue (56%) regions and red (35%) regions | Several samples showing regions of tumor and regions of radiation necrosis. Significant cauterize artifacts are noticed as well | Adenoid Cystic Carcinoma Cortical brain metastasis |
| 23 Metastasis #1 | Metastasis consisting of a central red (42%) region surrounded by a thick blue rim (47%) | Central slice shows a large necrotic region surrounded by significant regions of morphologically active tumor | NSCLC mediall brain metastasis Pathology report addressing metastases resected unblock |
| 23 Metastasis #2 | lesion consisting of blue (56%) regions and red (33%) regions | Morphologically active tumor is present in the histological samples | NSCLC cortical brain metastasis |
| 24 | lesion consisting of a large blue (56%) region surrounded by a red rim (34%) | Active tumor was found | Melanoma midline brain metastasis |
| 25 | lesion consisting of a blue central region (61%) surrounded by a red (33%) region | Active tumor was found | Breast cortical brain metastasis |
| 26 | lesion consisting of thin blue rim | Large mass of radiation necrosis. Small foci of | Breast peri-ventricular brain metastasis |
| 28 | (40%) within a larger red (51%) mass lesion is mostly red (53%) with small elongated blue regions (27%) | active tumor were found after ki67 staining Mostly necrotic samples with small foci of active tumor | NSCLC medial brain metastasis |

*Pathology report is based on all samples obtain from the neurosurgeons unrelated to the pre-surgical maps

TABLE 4

List of newly diagnosed GBM patients with post chemoradiation treatment follow-up

| Patient # | 1$^{ST}$ Surgery | 2$^{nd}$ Surgery | Samples compared with histology | Time to progression [months] | Treatment at progression |
|---|---|---|---|---|---|
| 1 | GTR | STR | 4 | 7.5 | Surgery + Bevacizumab |
| 2 | GTR | — | — | Not reached (19.7) | — |
| 3 | GTR | GTR | 8 | 6.5 | surgery |
| 4 | GTR | GTR | 2 | 6.2 | Surgery + Bevacizumab |
| 5 | STR | — | — | 3.6 | Bevacizumab |
| 6 | GTR | GTR | — | 11.6 | Surgery + Bevacizumab |
| 7 | GTR | — | — | Not reached) 12.5 | — |
| 8 | STB | — | — | Died from unrelated disease (3) | — |
| 9 | STB | — | — | Not reached (5.2) | — |
| 10 | GTR | — | — | 5.0 | Bevacizumab |
| 12 | STB | — | — | 4.1 | Bevacizumab |
| 15 | GTR | — | — | 3.6 | Bevacizumab |
| 18 | GTR | — | — | Not reached (5.2) | — |

Column #2: Patients were diagnosed with GBM prior to initiation of chemoradiation by histological analysis of either gross tumor resection (GTR), sub-total resection (STR) or stereotactic biopsy samples (STB)
Column #4: Stereotactic samples were taken from locations determined using the late enhancement subtraction maps calculated from the pre-surgical MRIs
Column #5: In cases where progression was not reached, the duration of follow-up is listed in parenthesis Example 5

In the present example, the delayed enhancement subtraction maps of the present embodiments are used for analyzing brain MRI of subjects treated with bevacizumab.

Four patients were subjected to bevacizumab (Avastin®) treatment. High resolution T1-weighted MR images were acquired and subtraction maps were calculated from these images. Acquisition sessions were held before treatment and several times after treatment. The predetermined time interval between two subtracted images was 75 minutes. Histological analysis was performed with tissue samples obtained from the on of these patients which underwent surgery after treatment with Avastin.

FIGS. 30A-F show contrast-enhanced T1-weighted MRI (FIGS. 30A, 30C and 30E) and respective subtraction maps (FIGS. 30B, 30D, 30F) of a patient prior to (FIGS. 30A and 30B) and 1 month (FIGS. 30C and 30D) and 3 months (FIGS. 30E and 30F) after initiation of treatment. A significant decrease of the red component and increase of the blue component with time can be seen.

In the first month, the enhancing lesion volume (on T1-Gd) decreased by about 50%, the red volume decreased by about 50% and the blue volume was stable. At 3 months, the enhancing lesion decreased by about 57% of its original volume, the red volume decreased by about 40% and the blue volume increased by about 25%, suggesting progression. The patient died a few weeks after the last MRI.

Figures 31C, 31D:
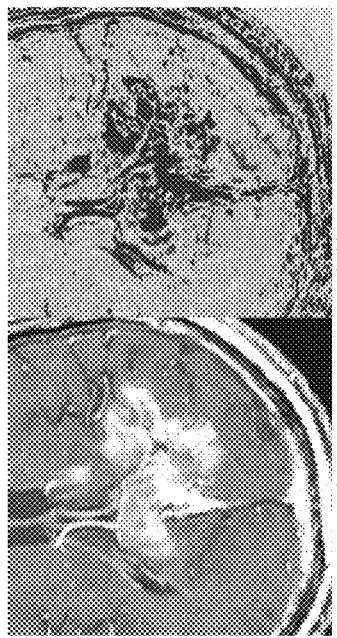
Figures 31E, 31F:
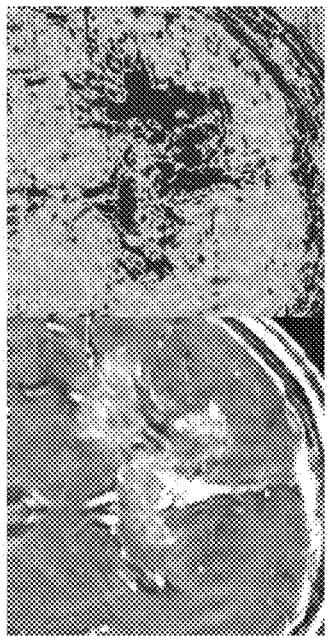
Figures 31A, 31B:
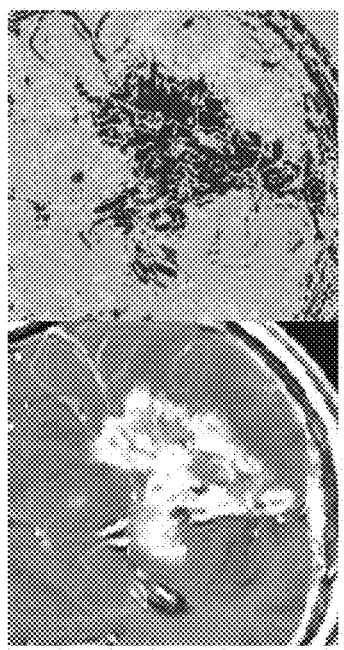
Figure 32A:
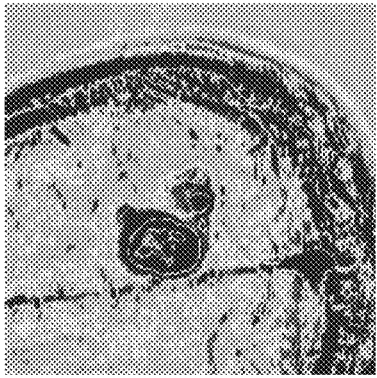
Figure 32B:
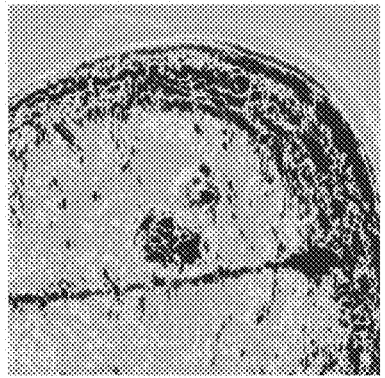
Figure 32C:
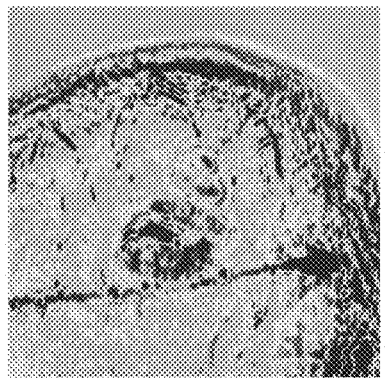
Figure 32D:
Figure 32E:
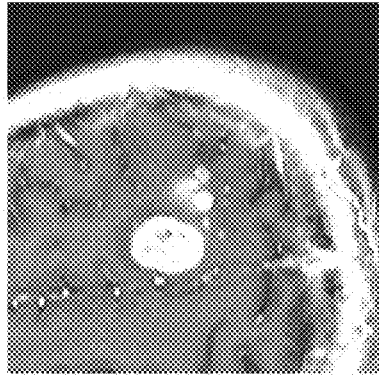
Figure 32F:
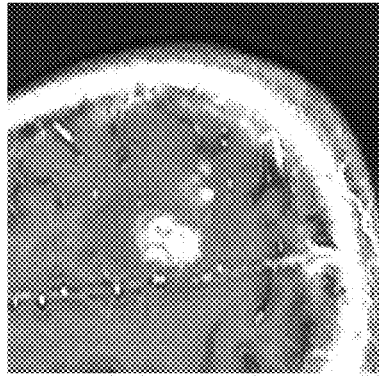
Figure 32G:
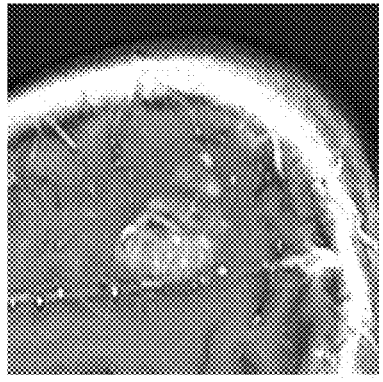
Figure 32H:
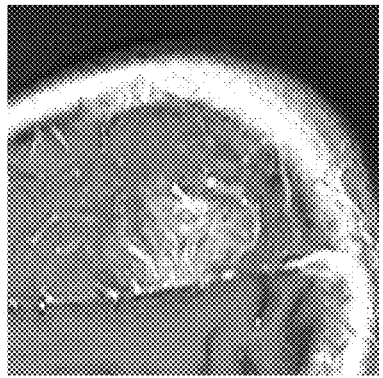

FIGS. 31A-F show contrast-enhanced T1-weighted MRI (FIGS. 31A, 31C and 31E) and respective subtraction maps (FIGS. 31B, 31D and 31F) of a patient prior to (FIGS. 31A and 31B) and 3 month (FIGS. 31C and 31D) and 5 months after initiation of treatment (FIGS. 31E and 31F).

As shown, in the first 3 months the maps of the present embodiments show progression (the blue volume increased significantly) although the lesion volume on T1-Gd was stable and edema decreased. At this point, due to clinical deterioration the patient was re-irradiated. Conventional MRI does not show improvement at the 5 months MRI but the maps of the present embodiments successfully show that most of the lesion turned red and the blue volume decreased significantly. The patient lived for another 5 months after the last MRI. FIGS. 31A-F demonstrate that the maps of the present embodiments can be used for assessing the responsiveness of the subject to bevacizumab treatment and to re-irradiation during bevacizumab treatment. The 5 months follow-up shows a significant response (red in the maps).

FIGS. 32A-H show T1-weighted MR images with Gd agent (FIGS. 32E-H) and respective subtraction maps (FIGS. 32A-D), of a patient prior to (FIGS. 32A and 32E), and 1 week (FIGS. 32B and 32F), 1 month (FIGS. 32C and 32G) and 3 months (FIGS. 32D and 32H) after initiation of treatment, showing continuous increase in the blue component accompanied by clinical deterioration.

In the first week, the enhancing lesion volume (on T1-Gd) was stable while the red volume increased by 30% and the blue decreased by 20%. At 1 month, the enhancing volume increased by 70%, the red decreased by about 50% and the blue increased by 200%. The patient was re-irradiated due to clinical deterioration. At 3 months all 3 volumes (enhancing lesion, red and blue) increased by over 500%. The patient died a few weeks following the last MRI.

FIGS. 33A, 33B, 33D and 33E show T1-weighted MR images (FIGS. 33A and 33D) and respective subtraction maps (FIGS. 33 B and 33E). FIG. 33C is histology sample of the blue volume in FIG. 33B (pointed by an arrow), FIGS. 33F and 33G is histology sample of the blue volume in FIG. 33E (pointed by an arrow). As shown the blue regions in the maps of the present embodiments are correlated with morphologically active tumor. The arrows in FIGS. 33A and 33D correspond to the arrows in FIGS. 33B and 33E, respectively.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of magnetic resonance imaging (MRI), comprising:
    administering contrast agent to a subject;
    acquiring a first MRI scan of a tissue, after said contrast administration;
    acquiring a second MRI scan of said tissue, at least 20 minutes after said acquisition of said first MRI scan;
    subtracting one of said MRI scans from another one of said MRI scans;
    based on said subtraction, distinguish between a slow population, in which contrast clearance from the tissue is slower than contrast accumulation, and a fast population in which contrast clearance is faster than contrast accumulation; and
    generating a displayed map identifying, in different colors, said fast population as an active tumor and said slow population as a tissue region other than an active tumor.

2. The method of claim 1, wherein said acquisition of said first MRI scan of said tissue is executed about 2 minutes after said contrast administration.

3. The method of claim 1, wherein said generating said displayed map comprises identifying said slow population as a non-tumoral tissue region.

4. The method of claim 3, wherein said non-tumoral tissue region is selected from a group consisting of (i) treatment effect, (ii) pseudo-progression, (iii) radiation-necrosis, (iv) inflammation, (v) post-surgical changes, (vi) tumor necrosis, and any combination thereof.

5. The method of claim 1, wherein said generating said displayed map comprises identifying said fast population as a tumor that is morphologically active.

6. The method of claim 1, wherein said generating said displayed map comprises identifying said fast population as a tumor characterized by at least one of: hyper cellularity, small cells, mitosis, high Ki67, pseudo-palicading necrosis and vascular proliferation.

7. The method of claim 1, comprising diagnosing said subject as having cancer, based on said displayed map.

8. The method of claim 7, comprising treating said subject for cancer.

9. The method of claim 1, comprising performing biopsy targeted to said fast population.

10. The method according to claim 1, comprising repeating the method in a follow-up session, identifying increment in a volume of said fast population, and determining tumor progression when said increment is above a predetermined threshold.

11. The method according to claim 1, comprising repeating the method in a follow-up session, identifying increment in a volume of said slow population but no increase or reduced increase in a volume of said fast population, and determining tumor pseudoprogression when said increment is above a predetermined threshold.

12. The method of claim 1, comprising constructing, for each MRI scan an intensity map, wherein the subtraction comprises subtracting said intensity maps.

13. The method of claim 1, comprising applying intensity variation correction to said MRI scans, prior to said subtraction.

14. The method of claim 1, comprising applying image registration to said MRI scans, prior to said subtraction.

15. The method of claim 14, wherein said image registration comprises whole body registration.

16. The method of claim 14, wherein said image registration comprises elastic registration.

17. The method of claim 1, comprising displaying at least one of said first and said second MRI scans, and enhancing a region corresponding to said tumor on said displayed MRI scans.

18. Apparatus for analyzing magnetic resonance images, comprising an image processor configured for receiving a first MRI scan of a tissue and a second MRI scan of said tissue, and for executing the method of claim 1.

19. The method of claim 1, comprising acquiring at least one additional MRI scan of the tissue, after said acquisition of said first MRI scan and before said acquisition of said second MRI scan, additionally subtracting said MRI first scan from each of said at least one additional MRI scan, and generating an additional displayed map also based on said additional subtraction.

20. Apparatus for analyzing magnetic resonance images, comprising an image processor configured for receiving a first MRI scan of a tissue and a second MRI scan of said tissue, and for executing the method of claim 19.

* * * * *